US008263140B1

(12) United States Patent
Dreher et al.

(10) Patent No.: US 8,263,140 B1
(45) Date of Patent: *Sep. 11, 2012

(54) POMEGRANATE BASED SKIN PROTECTANT AND TOPICAL APPLICATION

(75) Inventors: Mark Dreher, Wimberley, TX (US); Steve Anderson, Riverbank, CA (US)

(73) Assignee: Pom Wonderful, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/425,104

(22) Filed: Apr. 16, 2009

Related U.S. Application Data

(60) Provisional application No. 61/045,603, filed on Apr. 16, 2008.

(51) Int. Cl.
*A01N 65/00* (2009.01)
(52) U.S. Cl. ...................................................... 424/725
(58) Field of Classification Search ........................ None
See application file for complete search history.

(56) References Cited

U.S. PATENT DOCUMENTS

| | | | | |
|---|---|---|---|---|
| 3,069,370 | A * | 12/1962 | Jensen et al. ................. | 523/200 |
| 5,162,037 | A | 11/1992 | Whitson-Fischman | |
| 5,411,733 | A | 5/1995 | Hozumi et al. | |
| 5,624,698 | A | 4/1997 | Dake et al. | |
| 5,679,351 | A | 10/1997 | Walter et al. | |
| 5,830,887 | A | 11/1998 | Kelly | |
| 5,840,308 | A | 11/1998 | Jassim et al. | |
| 5,850,032 | A | 12/1998 | Wann | |
| 5,891,440 | A | 4/1999 | Lansky | |
| 6,030,622 | A | 2/2000 | Shehadeh | |
| 6,060,063 | A | 5/2000 | Lansky | |
| 7,943,185 | B1 * | 5/2011 | Anderson et al. ............ | 424/776 |
| 2002/0012710 | A1 | 1/2002 | Lansky | |
| 2002/0096579 | A1 * | 7/2002 | Sinders ........................ | 239/398 |
| 2002/0197341 | A1 * | 12/2002 | Lansky ........................ | 424/769 |
| 2005/0118312 | A1 | 6/2005 | Lansky | |
| 2007/0104730 | A1 | 5/2007 | Guo | |
| 2007/0280898 | A1 * | 12/2007 | Riddle ........................... | 424/74 |

FOREIGN PATENT DOCUMENTS

| | | |
|---|---|---|
| FR | 2178968 | 11/1973 |
| JP | 4124140 | 4/1992 |
| JP | 5310745 | 11/1993 |
| JP | 5320037 | 12/1993 |
| JP | 5329063 | 12/1993 |
| JP | 9110710 | 4/1997 |
| JP | 410298094 | 11/1998 |
| JP | 11243911 | 9/1999 |
| RU | 2088119 | 8/1997 |
| SU | 1251851 | 8/1986 |
| SU | 1442167 | 12/1988 |
| SU | 1733448 | 5/1992 |
| WO | WO 93/23069 | 11/1993 |
| WO | WO 95/22254 | 8/1995 |
| WO | WO 96/24327 | 8/1996 |
| WO | WO 98/29129 | 7/1998 |
| WO | WO 99/66941 | 12/1999 |

OTHER PUBLICATIONS

Seeram et al. "Bioavailability of ellagic acid in human plasma after consumption of ellagitannins from pornegrarote (*Punica granatum* L.) juice", Clinica Chirnica Acta 348 (2004) 63-68.

Seeram, et al., "Pomegranate Juice Ellagitannin Metabolites Are Present in Human Plasma and Some Persist in Urine for Up to 48 Hours", Journal of Nutrition, 2006, 2481-2485.

Seeram, et al. "Pomegranate Juice and Extracts Provide Similar Levels of Plasma and Urinary Ellagitannin Metabolites in Human Subjects" Journal of Medicinal Food, 11 (2) 2008, 390-394.

D. Syed, et al. "Photochemopreventive Effect of Pomegranate Fruit Extract on UVA-rnediated Activation of Cellular Pathways in Normal Human Epidermal Keratinocytes" Photochemistry and Photobiology, 2006, 82: 398-405.

Seeram, et al. "In vitro antiproliferative, apoptotic and antioxidant activities of punicalagin, ellagic acid and a total pomegranate tannin extract are enhanced in combination with other polyphenols as found in pomegranate juice" Journal of Nutritional Biochemistry, 16, 2005, 360-367.

Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006,54, 980-985.

V. Adhami, et al. "Polyphenols from green tea and pomegranate for prevention of prostate cancer" Free Radical Research, Oct. 2006: 40(10): 1095-1104.

S. Kasimsetty, et al. "Effects of Pomegranate Chemical Constituents/ Intestinal Microbial Metabolites on CYP1B1 in 22Rv1 Prostate Cancer Cells" Journal of Agriculture and Food Chemistry, 2009, 57, 10636-10644.

Sartippour, et al., "Ellagitannin-rich pomegranate extract inhibits angiogenesis in prostate cancer in vitro and in vivo" International Journal of Oncology, 2008, 32:475-480.

Rettig, et al. "Pomegranate extract inhibits androgen-independent prostate cancer growth through a nuclear factor-KB-dependent mechanism" Molecular Cancer Therapy, 2008; 7(9): 2662-71.

Seeram, et al. "Pomegranate Ellagitannin-Derived Metabolites Inhibit Prostate Cancer Growth and Localize to the Mouse Prostate Gland" Journal of Agricultural and Food Chemistry, 2007, 55, 7732-7737.

Hong, et al. "Pomegranate polyphenols down-regulate expression of androgen-synthesizing genes in human prostate cancer cells overexpressing the androgen receptor" Journal of Nutritional Biochemistry, 2008, 8 pages.

(Continued)

*Primary Examiner* — Michael Meller
(74) *Attorney, Agent, or Firm* — CotmanIP

(57) ABSTRACT

A cosmetic composition is provided having ingredients that may prevent signs or conditions of aging and/or damage in skin, improve the aesthetic appearance of skin, and promote recovery from environmental stresses. The composition includes natural ingredients, including pomegranate juice concentrate; pomegranate extract; pomegranate seed oil; and at least one pharmaceutically or cosmetically acceptable vehicle.

1 Claim, 28 Drawing Sheets

OTHER PUBLICATIONS

J. Khateeb, et al. "Paraoxonase 1 (PON1) expression in hepatocytes is upregulated by pomegranate polyphenols: A role for PPAR" Atherosclerosis, 2009, 7 pages.

M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.

O. Rozenberg, et al. Pomegranate juice sugar fraction reduces macrophage oxidative state, whereas white grape juice sugar fraction increases it Atherosclerosis, 188 (2006) 68-76.

Mattiello, et al."Effects of Pomegranate Juice and Extract Polyphenols on Platelet Function" Journal of Medicinal Food, 12 (2) 2009, 7 pages.

Sumner, et al. "Effects of Pomegranate Juice Consumption on Myocardial Perfusion in Patients With Coronary Heart Disease" American Journal of Cardiology. 2005, 5 pages.

M. Aviram, et al. "Pomegranate juice consumption inhibits serum angiotensin converting enzyme activity and reduces systolic blood pressure" Atherosclerosis, 158 (2001) 195-198.

M. Aviram, et al. "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins" Journal of Agricultural and Food Chemistry, 2008, 56, 1148-1157.

Shiner et al. "Macrophage paraoxonase 2 (PON2) expression is upregulated by pomegranate juice phenolic anti-oxidants via PPAR and AP-1 pathway activation" Atherosclerosis, 2007, 9 pages.

de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

de Nigris, et al. "Pomegranate juice reduces oxidized low-density lipoprotein downregulation of endothelial nitric oxide synthase in human coronary endothelial cells" Nitric oxide, 2006 15 259-263.

L. Ignarro, et al. "Pomegranate juice protects nitric oxide against oxidative destruction and enhances the biological actions of nitric oxide" Nitric oxide, 2006, 15, 93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13, 6 pages.

Resenblat, et al. "Pomegranate Byproduct Administration to Apolipoprotein E-Deficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006, 54, 1928-1935.

de Nigris, et al. "The influence of pomegranate fruit extract in comparison to regular pomegranate juice and seed oil on nitric oxide and arterial function in obese Zucker rats" Nitric Oxide. 2007 17, 50-54.

Fuhrman, et al. "Pomegranate juice inhibits oxidized LDL uptake and cholesterol biosynthesis in macrophages" Journal of Nutritional Biochemistry, 2005, 16, 570-576.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Aviram, et al. "Pomegranate juice consumption for 3 years by patients with carotid artery stenosis reduces common carotid intima-media thickness, blood pressure and LDL oxidation" Clinical Nutrition, 2004, 23,423-433.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Eliagitannins, Exhibit Potent Antioxidant Activity in a Cell-Based Assay" Journal of Agriculture and Food Chemistry, 2009, 57 10181-10186.

Y. Zhang, et al. "Absence of Pomegranate Ellagitannins in the Majority of Commerciai Pomegranate Extracts: Implications for Standardization and Quality Control" Journal of Agricultural and Food Chemistry, 2009, 57, 7395-7400.

Y. Zhang, et al. "International Multidimensional Authenticity Specification (IMAS) Algorithm for Detection of Commercial Pomegranate Juice Adulteration", Journal of Agricultural and Food Chernistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

K. Martin et al. "Development of a novel pomegranate standard and new method for the quantitative measurement of pomegranate polyphenols" Journal of Science of Food and Agriculture, 2009: 89:157-162.

N. Seeram, et al. "Comparison of Antioxidant Potency of Commonly Consumed Polyphenol-Rich Beverages in the United States" Journal of Agricultural and Food Chernistiy, 2008, 56, 1415-1422.

Gil et al. "Antioxidant Activity of Pomegranate Juice and Its Relationship with Phenolic Composition and Processing" Journal of Agricultural and Food Chemistry, 2000, 48, 4581-4589.

D. Bialonska, et al. "The Effect of Pomegranate (*Punica granatum* L.) Byproducts and Ellagitannins on the Growth of Human Gut Bacteria" Journal of Agricultural and Food Chemistry, 2009, 57, 8344-8349.

M. Haidari, et al. "Pomegranate(Punicagranatum) purified polyphenol extract inhibits influenza virus and has a synergistic effect with oseltamvir" Phytomedicine, 2009, 10 pages.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukia, et al. "Consumption of hydrolyzable tannins-rich pomegranate extract suppresses inflammation and joint damage in rheumatoid arthritis" Nutrition, 24, 2008, 733-743.

Z. Rasheed, et al. "Polyphenol-rich pomegranate fruit extract (POMx) suppresses PMACl-induced expression of pro-inflammatory cytokines by inhibiting the activation of MAP Kinases and NF-kB in human KU812 cells" Journal of Inflammation, 2009, 12 pgs.

Glycaemic Index Research Service "A Study to Measure the Glycaemic Index Value of Pomegranate Juice" The School of Molecular and Microbial Bio-sciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

K. Azadzoi, et al. "Oxidative Stress in Arteriogenic Erectile Dysfunction: Prophylactic Role of Antioxidants" Journal of Urology. 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Heath: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricuitural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVB-mediated damage in human reconstituted skin" Experimental Dermatology, 2009.

A. Pantuck, et al. "Phase II Study of Pomegranate Juice for Men with Rising Prostate-Specific Antigen following Surgery or Radiation for Prostate Cancer" Clinical Cancer Research; 12(13) Jul. 1, 2006, 4018-4026.

M. Aviram, et al. "Pomegranate juice consumption reduces oxidative stress, atherogenic modifications to LDL, and platelet aggregation: studies in humans and in atherosclerotic apolipoprotein E-deficient mice" American Journal of Clinical Nutrition, 2000: 71:1062-76.

D. Pérez. et al., Wine, Diet, Antioxidant Defenses and Oxidative Damage. Annals of the New York Academy of Sciences (2002),957: 136-145.

KJ Joshipura, et al., The Effect of Fruit and Vegetable Intake on Risk for Coronary Heart Disease. Annals of Internal Medicine (2001),134:1106-1114.

http://www.wonderfulpomegranateresearch.com/featured.

Katz SR, Newman RA, Lansky EP, "*Punica granatum*: heuristic treatment for diabetes mellitus" J Med Food, Jun. 2007, 10(2):213-7.

Lansky EP, Newman RA, "*Punica granatum* (pomegranate) and its potential for prevention and treatment of inflammation and cancer" J Ethnopharmacol, Jan. 19, 2007, 109(2):177-206.

Lansky EP "Beware of pomegranates bearing 40% ellagic acid" J Med Food, 2006 Spring, 9(1): 119-22.

Aslam MN, Lansky EP, Varani J "Pomegranate as a cosmeceutical source pomegranate fraction promote proliferation and . . . " J Ethnopharmacol, Feb. 20, 2006, 103(3):311-8.

Lansky EP, Harrison G, Froom P et al. "Pomegranate (*Punica granatum*) pure chemicals show possible synergistic inhibition of human . . ." Invest New Drugs, Mar. 2005, 23(2):121-2.

Mehta R, Lansky EP "Breast cancer chemopreventive properties of pomegranate (*Punica granatum*) fruit extracts in a mouse mammary . . . " Eur J Cancer Prev, Aug. 2004, 13(4).345-8.

Lansky EP, Jiang W, Mo H, et al. "Possible synergistic prostate cancer suppression by anatomically discrete pomegranate fractions" Invest New Drugs, Jan. 2005, 23(1):11-20.

Albrecht M, Jiang W, Kumi-Diaka J, et al. "Pomegranate extracts potently suppress proliferation, xenograft growth, and invasion of human . . . " J Med Food, 2004 Fall,7(3):274-83.

Kawaii S, Lansky EP "Differentiation-promoting activity of pomegranate (*Punica granatum*) fruit extracts in HL-60 human . . . "J Med Food, 2004 Spring, 7(1):13-8.

Toi M, Bando H, Ramachandran C, et al. "Preliminary studies on the anti-angiogenic potential of pomegranate fractions in vitro and in vivo" Angiogenesis, 2003, 6(2):121-8.

Van Elswijk DA, Schobel UP, Lansky EP, et al. "Rapid dereplication of estrogenic compounds in pomegranate (*Punica granatum*) . . . " Phytochemistry, Jan. 2004, 65(2)233-41.

Hora JJ, Maydew ER, Lansky EP, et al. "Chemopreventive effects of pomegranate seed oil on skin tumor development in CD1 mice" J Med Food, 2003 Fall, 6(3):157-61.

Kim ND, Mehta R, Yu W, et al. "Chemopreventive and adjuvant therapeutic potential of pomegranate (*Punica granatum*) for . . . " Breast Cancer Res Treat, Feb. 2002,71(3):203-17.

Schubert SY, Lansky EP, Neeman I "Antioxidant and eicosanoid enzyme inhibition properties of pomegranate seed oil and fermented . . . " J Ethnopharmacol, Jul. 1999, 66(1):11-7.

\* cited by examiner

POMEGRANATE BASED SKIN PROTECTANT AND TOPICAL APPLICATION

This application claims benefit of U.S. Provisional Patent Application Ser. No. 61/045,603 filed Apr. 16, 2008 the specification of which is hereby incorporated herein by reference.

BACKGROUND OF THE INVENTION

1. Field of the Invention

One or more embodiments of the invention described herein pertain to the field of skin care compositions and methods relating to the production of such products. More particularly, but not by way of limitation, one or more embodiments of the invention relate to a pomegranate based skin care composition particularly for topical applications related to counteracting skin aging, preventing risk of skin cancer, and improving overall skin health.

2. Description of the Related Art

Many personal care products currently available to consumers are directed primarily to improving the health and/or physical appearance of the skin. Among these skin care products, many are directed to delaying, minimizing or even eliminating skin wrinkling and other histological changes typically associated with the aging of skin or environmental damage to human skin. Numerous compounds are described in the art as being useful for regulating skin condition, including regulating fine lines, wrinkles and other forms of uneven or rough surface texture.

Skin aging is a complex phenomenon that occurs from interactions between many extrinsic and intrinsic factors. Extrinsic factors include ultraviolet (UV) radiation (e.g., from sun exposure), environmental pollution, wind, heat, low humidity, harsh surfactants, abrasives, and the like. Intrinsic factors include chronological aging and other biochemical changes (e.g., from genetically programmed process) from within the skin. Whether extrinsic or intrinsic, these factors result in visible signs of skin aging and environmental damage, such as wrinkling and other forms of roughness (including increased pore size, flaking and skin lines), loss of rigidity or elasticity, uneven pigmentation on the surface, and other histological changes associated with skin aging or damage. To many people, the visible signs of skin aging or damage are a reminder of the disappearance of youth. As a result, the elimination of visible signs of skin aging or damage is a booming business in youth-conscious societies. Treatments range from cosmetic creams and moisturizers to various forms of cosmetic surgery.

Ultraviolet (UV) radiation from the sun is one of extrinsic factors associated with skin disorders in human. UV radiation induces a number of harmful responses including erythema, edema, hyperpigmentation, hyperphasic responses, immunosuppression, photoaging and skin cancer. Both UVB and to a lesser extent UVA are causative factors for sun-light induced skin disorders diagnosed in humans. UVB radiation is the most damaging part of the solar radiation reaching the earth and acts mainly on the epidermal basal cell layer of skin. Exposure of skin to UV light initiates a photo-oxidative reaction which impairs the antioxidant status and increases cellular level of reactive oxygen species (ROS) accompanied by activation of many ROS-sensitive signaling pathways. This impairs the ability of skin to protect itself resulting in increased oxidative stress, with consequent damage to the cutaneous tissues, a process commonly known as "photoaging". Among all adverse effects of UV radiation, skin cancer is of greatest concern because the incidence of nonmelanoma skin cancer has been increasing at an alarming rate and is the leading cause of malignancy in the United States.

Primary prevention of skin cancer, which includes the use of sunscreens or wearing of protective clothing, is recommended for reducing the risk of skin cancer but for many reasons these primary prevention approaches have met with limited success. Sunscreens and other anti-aging actives are not effective in revitalizing skin that has already been damaged by sun, aging or other factors.

Improved identification of key botanical and/or chemical actives for the effects on skin aging are made possible by analyzing for levels of the various biomarkers implicated in various skin disorders. It has been shown that exposure of human skin to UVB radiation upregulates the synthesis of the matrix-degrading enzymes matrix metalloproteinases (MMP), such as MMP-1, -2, -3, -7, -8, -9, -11, and -12, which have been implicated in photoaging. UVB-mediated activation of biomarkers, mitogen-activated protein kinases (MAPK) and nuclear factor kappa B (NF-kB), plays an important role in inflammation, immunity, cell proliferation and skin carcinogenesis. As aforementioned, ROS have been implicated in many of the undesirable aspects of skin aging whether due to intrinsic cause or exposure to UV radiation.

Aquaporins (AQPs) are proteins that facilitate the transport of water across cell membranes. So far, thirteen different AQPs have been identified in mammals (AQP 0-12). The aquaglyceroporin AQP3 expression is related to the expressions of other epidermal proteins involved in water maintenance (i.e., CD44, claudin-1, and filaggrin). The expressions of AQP3 water channels are strongly affected by age and chronic sun exposure, and a defective osmotic equilibrium could occur in the epidermis, which would account for the skin dryness observed in older people and skin areas most exposed to sunlight.

Based on the foregoing, there is a continuing need to formulate skin care compositions with a viable shelf life containing actives that are effective in retarding the aging effects of sunlight, retarding the natural effects of aging on the skin, such as drying and loss of elasticity and improving the appearance of skin, moisturizing/re-hydrating and tightening and firming skin, while also having any combinations of potent free radical scavenging, antioxidant, antiflammatory, antimicrobial, antiproliferative and antitumoriogenic properties.

BRIEF SUMMARY OF THE INVENTION

One or more embodiments of the invention are directed to a skin care composition containing different bioactive compositions derived from a whole pomegranate fruit (e.g., peel, juice, and seeds). Topical applications of different pomegranate-derived bioactive compositions in combination with cosmetically or pharmaceutically acceptable carriers or vehicles synergistically regulates visible and/or tactile discontinuities in mammalian skin, including fine lines, wrinkles, enlarged pores, roughness, dryness, and other skin texture discontinuities, e.g., reduces or effaces the visibility of fine lines, wrinkles, and other forms of uneven or rough surface texture associated with aged or photodamaged skin. Also for example, topical applications of three different pomegranate-derived bioactive compositions in combination synergistically ameliorates conditions of erythema, edema, hyperpigmentation, hyperplastic responses, immunosuppression, and skin cancer in mammalian skin, including oxidative stress, histological changes in the extracellular matrix (reflecting an aged or photoaged skin with loss of rigidity, elasticity, skin appears rough, leathery with deep coarse wrinkles and uneven pigmentation on the surface), and pathological processes associated with aged or photodamaged skin such as, for example, arthritis, skin aging, tumor invasion, and metasasis. One or more embodiments of the invention provide skin care compositions that improve the appearance of skin and remediate the effects of aging. Another aspect of the invention provides skin care compositions having chemical and/or botanical actives derived from whole pomegranate fruits (peels, juice, seeds) and combined with pomegranate oil. The compositions may also contain additional skin care agents.

One or more embodiments of the invention are methods for stimulating wound healing in a subject in need thereof, comprising administering to a wound of the subject an amount of a composition effective for stimulating wound healing, wherein the composition comprises one or more bioactive composition derived from whole pomegranate fruits.

These and other aspects of the invention, and equivalents thereof, are achieved by skin care compositions having actives derived from pomegranate, and the use of such compositions for topical application to the skin. The cosmetic compositions described herein provide rejuvenation benefits to the skin and/or improving the aesthetic appearance of skin. More particularly, one or more embodiments of the invention relate to compositions that remediate the effects of aging as expressed in a product that is made to resolve the shelf life problem historically present in products containing pomegranate oil.

The composition made in accordance with one or more embodiments of the invention has an effective amount of pomegranate extract, pomegranate juice concentrate and/or pomegranate seed oil. In cases where the pomegranate seed oil is included it can be done so using a stable and deodorized form of the pomegranate seed oil or packaged in an airless pump using the general manufacturing methodology described herein. In one or more embodiments of the invention, the pomegranate extract, pomegranate juice concentrate and/or pomegranate seed oil are combined with cosmetically or pharmaceutically acceptable vehicles.

In one or more embodiments of the invention, the composition of the invention which enable dermal layer dispersion of pomegranate-derived compositions can include a carrier in a form of encapsulant incorporating the bioactive compositions of the pomegranate. The pomegranate oil may, for instance, be encapsulated to reduce the time by which the oil becomes subject to rancidity issues. Topically applying an effective amount of the pomegranate composition to the skin (epidermis) of a patient needing such treatment is generally used as the manner of treatment. In one variant of the invention the composition is a dispersion of lipid vesicles encapsulating an aqueous phase. The aqueous phase may contain water-soluble bioactive substances and the bimolecular layers of amphiphilic lipids may contain lipophilic bioactive substances. According to a second embodiment of this variant, the compositions according to the invention comprise an oil-in-water emulsion formed from vesicles with an oily core having an encapsulant coating, i.e. containing vesicles comprising a lipid membrane encapsulating an oily phase.

BRIEF DESCRIPTION OF THE DRAWINGS

The above and other aspects, features and advantages of one or more embodiments of the invention will be more apparent from the following more particular description thereof, presented in conjunction with the following drawings wherein.

DETAILED DESCRIPTION

Figure 1:
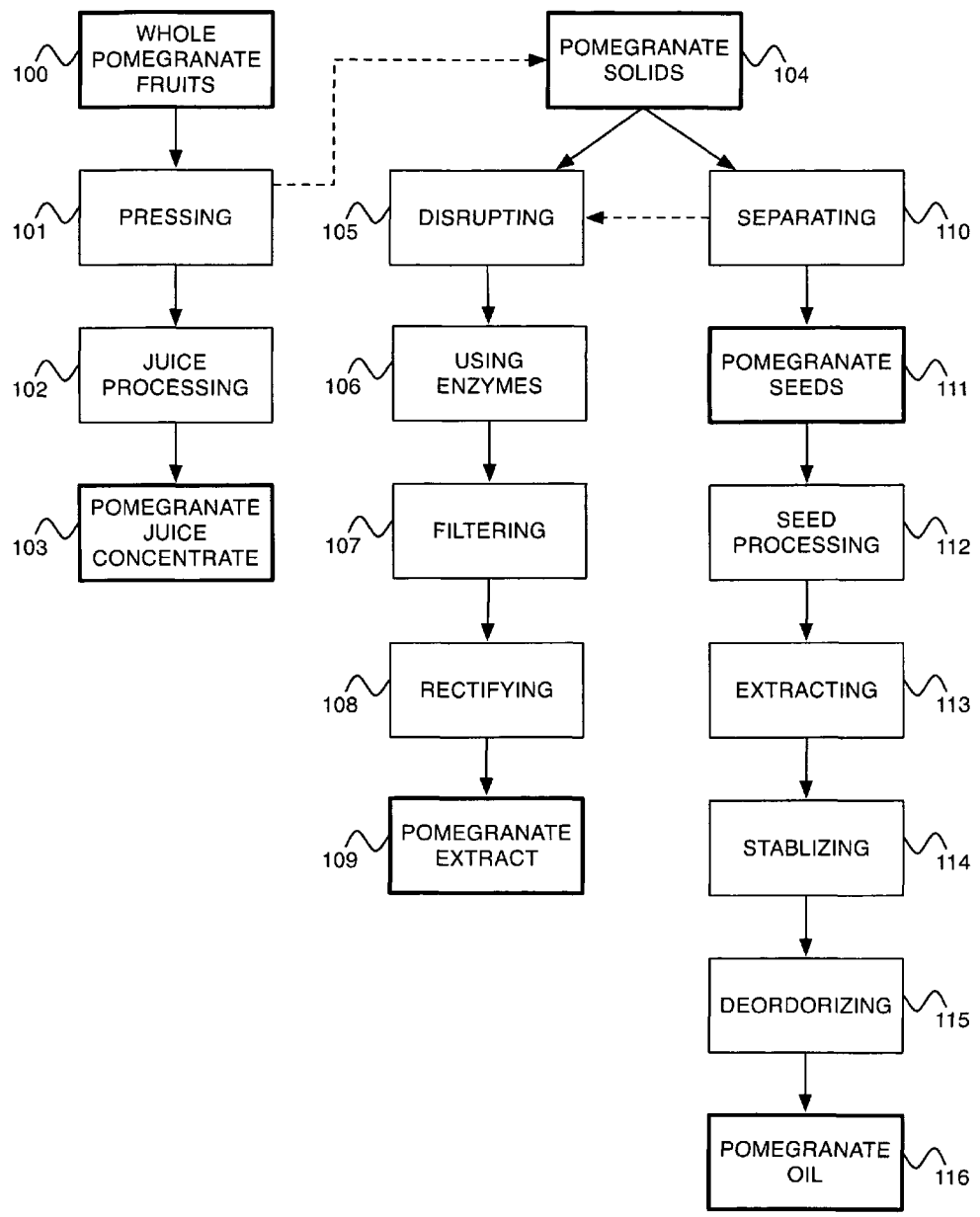
FIG. 1 illustrates an embodiment of the process of obtaining pomegranate juice concentrate (PJC), pomegranate extract (PE) and pomegranate seed oil (PSO).

A pomegranate based skin care composition and methods of making and using the same will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features well known to those of ordinary skill in the art have not been described in detail so as not to obscure the invention. Readers should note that although examples of the invention are set forth herein, the claims, and the full scope of any equivalents, are what define the metes and bounds of the invention.

DEFINITIONS

As used herein, the terms "administering", "administration", and like terms refer to any method which, in sound medical or cosmetic practice, delivers the composition to a subject in such a manner as to provide a desired effect on a dermatological disorder, condition, or appearance. The compositions are generally administered such that they cover area to be treated. "Direct administration" refers to any method which, in sound medical or cosmetic practice, delivers the composition to a subject without use of another composition, delivery agent, or device. "Indirect administration" refers to any method which, in sound medical or cosmetic practice, delivers the composition to a subject with use of at least another composition, delivery agent, or device.

As used herein, the phrases an "effective amount" or a "therapeutically effective amount" of a pharmaceutically active agent or ingredient, which are synonymous herein, refer to an amount of the pharmaceutically active agent sufficient enough to have a desired effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and other factors that might have an influence on general effectiveness.

As used herein, the phrase "wound" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, incisions, excoriations, those injuries sustained in automobile and other mechanical accidents, and those caused by bullets, knives and other weapons, ulcer such as pressure ulcer, plaster ulcer and decubitus ulcer, and post-surgical injuries, as well as chronic conditions such as pressure sores, bedsores, conditions related to diabetes and poor circulation, and all types of acne. In addition, said wound includes dermatitis such as impetigo, intertrigo, folliculitis and eczema.

As used herein, the phrase "skin protectant" refers to a composition or compositions that have the ability to provide some measurable level of protection to the skin's dermal layer from sun-induced damage and/or result in improvements in skin integrity.

As used herein, the phrase "skin care composition" refers to a composition which, upon administration, demonstrates a therapeutic affect upon a subject, more particularly mammals.

As used herein, the phrase "pomegranate-derived composition" refers to one or any combination of pomegranate juice concentrate (PJC), pomegranate extract (PE), and pomegranate seed oil (PSO) described herein.

Areas of the body which can be treated with the present invention include, but are not limited to, skin, muscle and internal organs. Hereinafter, the term "subject" refers to a human or lower animal on whom the present invention is practiced.

Other terms as used herein are meant to be defined by their well-known meanings in the art.

Pomegranate-Derived Compositions

According to one or more embodiments of the invention, topical skin care composition comprises a combination of at least two different pomegranate-derived compositions, each having different properties. The pomegranate-derived compositions are pomegranate juice concentrate (PJC) and pomegranate oil (PSO) or pomegranate extract (PE) and pomegranate seed oil (PSO). In one but not all embodiments of the invention the formulated composition may make use of PJC, PE and PSO but in other embodiments of the invention variations do not make use of all three compositions. Maintaining the shelf life of some of the pomegranate-derived compositions, for example the PSO may rely on the specific process described hereinafter. Both the PJC and PE contain ingredients from the whole pomegranate fruit.

Pomegranate juice concentrate (PJC) as used in one or more embodiments of the invention is substantially derived from whole fruits of pomegranate, including the arils, the pericarp, the inner membrane and the seeds. Pomegranate juice concentrate may be obtained by any conventional juice making process that yields about 65° Brix pomegranate juice concentrate.

Pomegranate extract (PE) as used in one or more embodiments of the invention is substantially derived from pomegranate solids, which are any one or more of the group consisting of the pericarp, inner membrane and seeds of the pomegranate. Pomegranate extract, as obtained from the pomegranate solids, have substantially higher total polyphenol content than is found in the juice from the pomegranate arils. This is particularly true with respect to the higher molecular weight polyphenols and in particular, punicalagin. In addition to puncalagin, other high molecular weight polyphenols, including ellagitannin and other hydrolysable tannins, have been characterized in the extract of pomegranate solids. An example of a process that yields pomegranate extract as used in one or more embodiments of the invention is described in the U.S. Application No. 20060269629, which is hereby incorporated by reference in its entirety. Pomegranate seed contains approximately 65% punicic acid, a conjugated linolenic acid (9Z,11E,13Z-octadeca-9,11,13-trienoic acid). Particularly for pomegranate seeds, using conventional processes for isolating oil from fruit seeds, including cold press techniques, yield an unstable and vulnerable product susceptible to decay and goes rancid without hesitation. The pomegranate seed oil product from using the conventional processes has unpleasant odor unsuitable for topical and cosmetic applications and also has a gel-like constituency that has a little practical use in various preparations for commercial products such as cosmetics, skin creams, dietary supplements and other medicinal applications.

Pomegranate seed oil as used in one or more embodiments of the invention are preferably stabilized and relatively odor free. An example of an extraction and stabilizing process that yields stabilized and deodorized form of pomegranate seed oil is described in the U.S. application Ser. No. 11/687,480, which is hereby incorporated by reference in its entirety. In embodiments of the invention where the pomegranate oil is not stabilized variations in manufacturing and packaging are made to enable distribution of a skin care composition that lacks rancidity issues.

OBTAINING. The obtaining step is shown in block 5 of FIG. 1 and in further detail in FIG. 5. Drawing forth of seed oil from flaked pomegranate seed is generally accomplished by applying external pressure [107, 503] and/or through the use of solvent extraction using iso-hexane [106, 501]. For example, 2-methyl pentane (isohexane) [502] generally serves as a reliable solvent for extracting the seed oil. The drawing forth of seed oil from flaked pomegranate seed may be carried out by solvent extraction using 2-methyl pentane (isohexane) with 50-1,000 ppm tocopherols or other natural antioxidants such as Rosemary or synthetic antioxidants such as BHA/BHT [502]. The solvent extraction may be carried out using an extractor (such as a Soxhlet) wherein pomegranate seed flakes can be loaded in to the screen sample holder and extracted for four hours to result in an extraction yield of greater than 95%. The solvent extraction may be carried out in 2-methyl pentane on a counter-current extractor (such as Crown) under effective operating conditions. The effective operating conditions for a counter-current extractor may be the following: Flake feed rate 65 Kg/h, Retention time of 60 minutes, Bed level setting at minimum, fresh solvent flow 150±5 Kg/h, Solvent temperature 52±4° C., RFE feed rate 21 µm, RFE steam pressure 13 psi, DT sparge steam off, DT top tray temperature 84±3° C., DT bottom tray temperature 100±2° C. The solvent extraction may contain the addition of mixed tocopherols to 2-methyl pentane to minimize oxidation of the oil. Mixing in tocopherols or other antioxidants may be added at a quantity of 50 to 1,000 ppm. The extraction may yield crude oil that has a PV of 0.69, FFA of 1.54%, and Lovibond color parameters (1 inch sample cell) 70.0Y and 2.9R.

Figure 6:
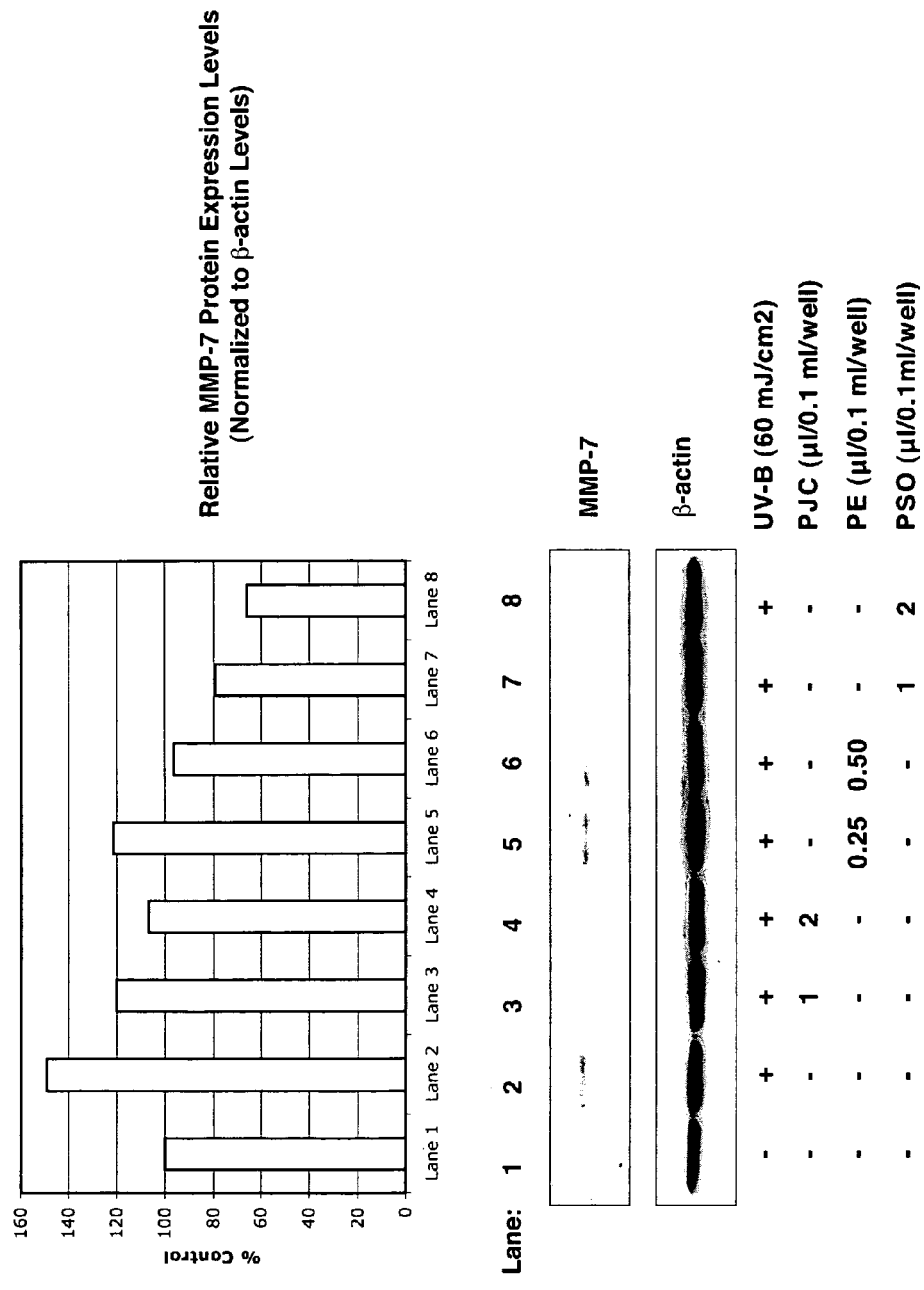
FIG. 6 is a digital composite image containing a bar graph of relative protein expression levels of MMP-7 (matrilysin) and depicting the effects of PJC, PE, and PSO on UVB-mediated induction of matrix metalloproteinases (MMPs) in skin tissue samples.

STABILIZING (refining). The stabilizing step is shown in FIG. 1 and in further detail in FIG. 6 and FIG. 7. Stabilizing has two major components refining, shown in FIG. 6, and bleaching, shown in FIG. 7. One or more embodiments of the invention are directed to a unique process for stabilizing isolated *Punica granatum* seed oil [108, 600, 700]. FIG. 6 depicts further detail of the refining step of the stabilizing process [600]. The general objective in refining is to free the extracted pomegranate seed oil from impurities and/or unwanted material [601]. The impurities may be caustic, black sediment, or otherwise undesirable material. The process for freeing the impurities is generally referred to as refining or caustic refining [602]. Stabilizing the *Punica granatum* seed oil may require caustic refining Crude oil extracted from pomegranate seed flakes may contain undesirable material. The stabilization may involve water washing [603] and require assessment of the need for refining the oil; Free fatty acid (FFA) values may indicate a need for caustic refinement of the oil. FFA values may be near 1.54% indicating a need for further refinement. Such refining is generally carried out by heating the crude pomegranate seed oil to 65° C. and adding 0.1% phosphoric acid. The mixture of crude pomegranate seed oil and phosphoric acid may then be mixed for 15 minutes and sodium hydroxide (18 Be) may be added at 1-4% of the starting oil weight [604]. The mixture may then be clarified [605] by heating to 40 to 50° C. and applying centrifugation [606] to remove undesirable black sediment and other impurities from the oil. After the clarifying 15% (w/w) may be added and mixed for 15 minutes at 75° C. [606]. Oil may be recovered from water wash by centrifugation [607]. This process may yield an FFA value of the caustic refined and water washed oil of less than 0.5%. The refining process may include a winterization step wherein refrigeration is applied to facilitate wax removal.

Figure 7:
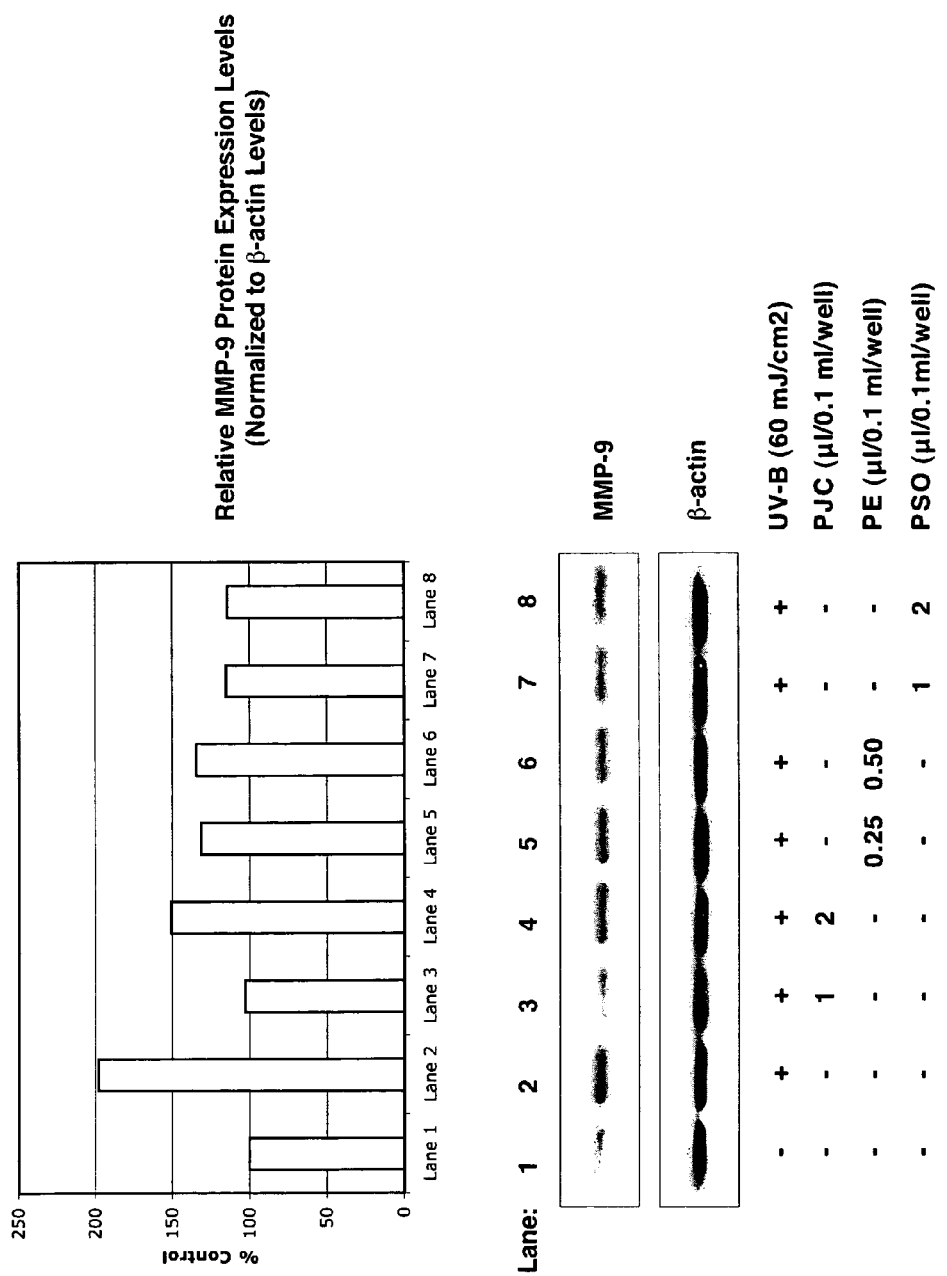
FIG. 7 is a digital composite image containing a bar graph of relative protein expression levels of MMP-9 (gelatinase B) and depicting the effects of PJC, PE, and PSO on UVB-mediated induction of matrix metalloproteinases (MMPs) in skin tissue samples.

STABILIZING (Bleaching). As previously stated stabilizing requires a two-fold process of refining and bleaching. FIG. 7 depicts further detail of the bleaching aspect of the stabilizing process [700] which generally lightens or removes color from the pomegranate seed oil [701]. This process of lightening or removal of color is generally referred to as bleaching [701]. The bleaching may be carried out using bleaching clay or activated carbon [702], applying heat and adding citric acid and mixing [703] and pre-heating oil to 65° C. [704]. Quantities of 0.2% citric acid are typically effective when mixing [705]. A filter aid (e.g. cellulose acetate) and mixing [706] is also beneficial. When adding clay 0.5-5% clay at 75-115° C. for 10-60 minutes in a reactor under full vacuum [707] is effective. Cooling the oil to 50 to 80° C. and filtering [708] also produces results. While any means for bleaching is acceptable, bleaching is generally carried out in a reactor (such as Parr) using various grades of bleaching clay and may undergo the following exemplary steps. Oil may be pre-heated to 65° C. and 0.2% citric acid may be added and mixed for 15 minutes. Trisyl 5615 filter aid (0.2% w/w) may be added and mixing continued for another 15 minutes. Bleaching clay (%3, w/w) may then be mixed into the oil and the reactor sealed. Bleaching may be performed at 95° C. for 30 minutes under full vacuum. The oil may then be cooled to 65° C. and filtered. The bleaching may be carried out using bleaching clay such as Tonsil Supreme 124FF and undergo the following steps: Oil can be heated to 65° and 0.2% citric acid added and mixed for 15 minutes. Trisyl S615 filter aid (0.2%, w/w) can be added and mixing continued for an additional 15 minutes. Bleaching clay (3%, w/w) may then be mixed into the oil and the reactor sealed. Bleaching may be performed at 95° C. for 30 minutes under full vacuum in a mini-RBD bleaching reactor. The oil may then be cooled to 65° C. and filtered. The above mentioned steps may effectively lighten the color of the oil to achieve Lovibond Y and R values of 2.0 and 0.2, respectively.

Figure 8:
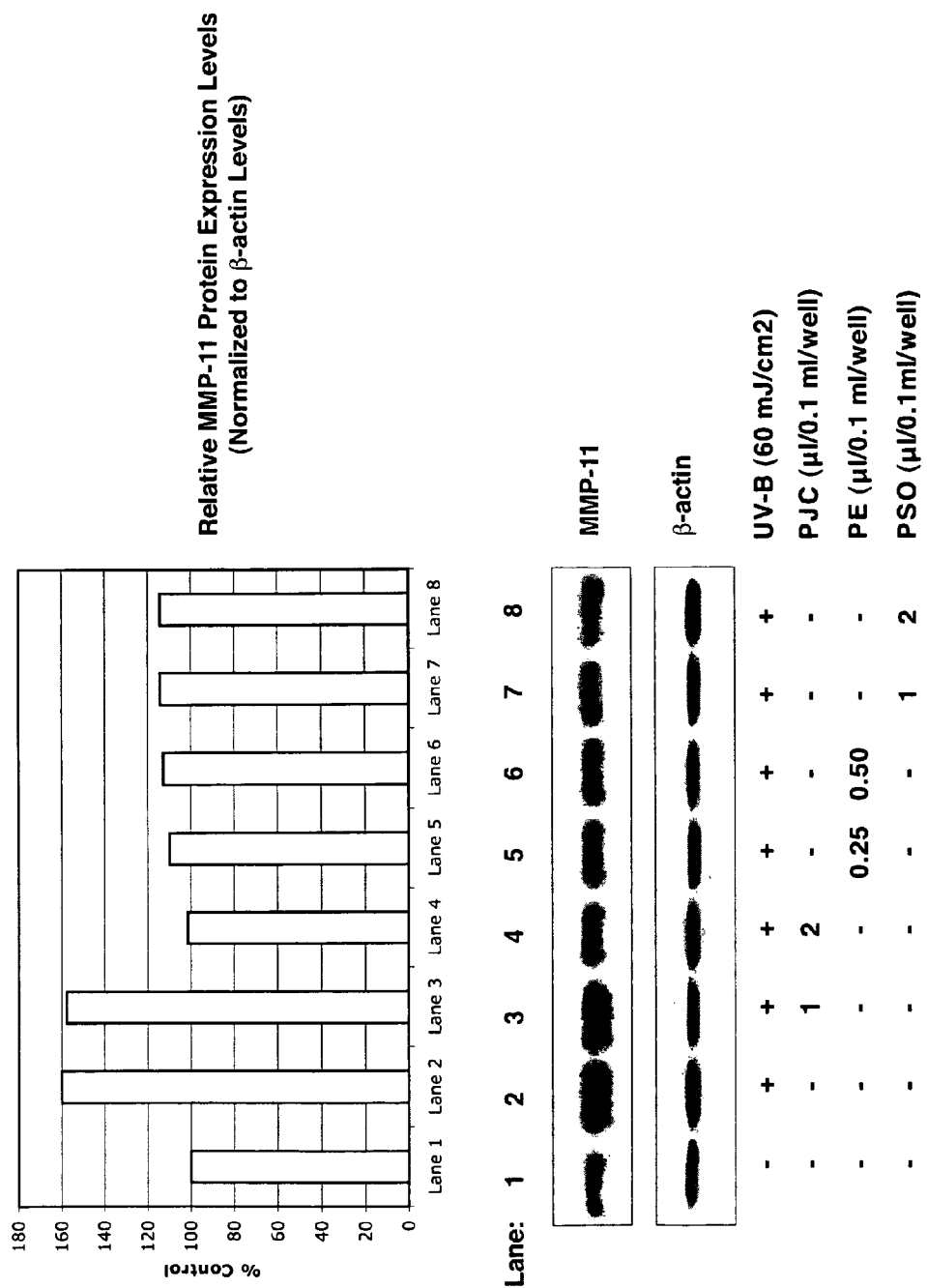
FIG. 8 is a digital composite image containing a bar graph of relative protein expression levels of MMP-11 (stromelysin-3) and depicting the effects of PJC, PE, and PSO on UVB-mediated induction of matrix metalloproteinases (MMPs) in skin tissue samples.

DEODORIZATION. Deodorization is shown in FIG. 1 and in FIG. 8 in further detail [800]. One or more embodiments of the invention make use of a deodorizing step to remove unpleasant qualities of pomegranate seed oil such as its offensive odor when extracted in raw form. The elimination or prevention of offensive odor of pomegranate seed oil is referred to as deodorizing. FIG. 8 depicts the process of deodorizing in detail [800]. Deodorizing is generally carried out by placing seed oil under vacuum pressure (e.g., 18-28 mm Hg [802]) and heating the seed oil to a set temperature (e.g., 180-210° C. [803]) for a set time [801] such as 30-120 minutes and sparging using steam or nitrogen gas [804, 805]. The deodorizing step also involves cooling the seed oil to 40-90° C. and coarse filtering [806, 807]. An antioxidant mixture such as tert-butylhydroxyquinone (TBHQ) at 50-200 ppm, tocopherols at 50-200 ppm and/or acrobyl palmitate at 50-200 ppm [808] is generally helpful. Other quantities of tocopherol, TBHQ and ascobyl palminate are however also within the scope and spirit of the invention. The elimination or prevention of offensive odor of pomegranate seed oil may be carried out by heating the oil using a heating apparatus and vacuum to a target temperature range below 210° C. The deodorization may occur by taking bleached pomegranate seed oil under vacuum pressure (28-30 mm Hg) and heating it to a temperature between 180-210° C. for 30 to 120 minutes. The preferred deodorization residence time range is 30 to 60 minutes.

The present invention provides a novel process that allows for the preparation of pomegranate seeds and the subsequent extraction, stabilization and deodorization of the polyphenol rich pomegranate seed oil.

The present method comprises a number of separate phases, which, taken together, produce the beneficial result. However, it will readily appreciated that the division of the method into separate phases is an artificial construct, primarily to aid in the clarity of presenting the invention, and that various aspects of any particular phase may be performed out of the described order, or combined with aspects ascribed to other phases, while still obtaining the benefits of the invention.

The method for making pomegranate seed oil includes the processing steps of separating, drying, air aspiration, flaking, obtaining seed oil, stabilizing which includes refining and bleaching and deodorization.

In summary, FIG. 1 illustrates an embodiment of the process of obtaining pomegranate juice concentrate (PJC), pomegranate extract (PE) and pomegranate seed oil (PSO). Pomegranate juice concentrate 103 is obtained from whole pomegranate fruits 100 that undergo pressing step 101 that extract juices by bearing an external pressure against the whole fruits in ways that such juice is expelled therefrom. The pressing step 101 may include any method of forcing juices out of the whole fruits, including crushing and grinding. Any insoluble residues left over from the pressing step 101 are pomegranate solids 104 which are used to make other pomegranate-derived compositions. The resulting pressed juice undergoes juice processing step 102 which filters out solid residues, pasteurizes and concentrates the pressed juice. In one or more embodiments of the invention this results in about 65° Brix pomegranate juice concentrate 103, but other concentrations remain within the scope and spirit of the invention.

Pomegranate solids 104 may be obtained from one or more steps of pressing 101 of whole pomegranate fruits. As used herein, the term "pomegranate solids" refers to any one or a combination of the pericarp, the inner membrane and seeds of a pomegranate. Pomegranate solids 104 may be dispersed in an aqueous solution. Pomegranate solids 104 undergo disrupting step 105 to create a rough grind of pomegranate solids. The disrupting step may use any method to produce rough grind or fine particles of pomegranate solids, include milling or crushing. The mixture of disrupted pomegranate solids dispersed in aqueous solution undergo using enzymes step 106 to liberate phytochemicals from the plant tissues and/or cells. Such enzymes include any one or a combination of pectinase, cellulase, hemicellulase, amylase, arabanase, and other hydrolyzing enzymes, to name a few. After enzymes have at least partially degraded the pomegranate solids, the residual insoluble materials are removed from the mixture through filtering step 107. Filtering step 107 may be accomplished by filtration, centrifugation, chromatographic techniques, and other techniques. The resulting filtered supernatant 108 from filtering step 107 undergo rectifying step 108 using any method to concentrate the liquid extract to about 70° Brix. The resultant 70° Brix liquid extract is pomegranate extract (PE) 109.

Pomegranate extract (PE) contains polyphenols, including hydrolysable tannins and flavonoids. Pomegranate extract of the varietal used in one or more embodiments of the invention (e.g., the Wonderful variety of *Punica Granatum*) comprises principally hydrolysable tannins, a lesser amount of flavonoids, and a much smaller amount of ellagic acid. As a group, the family of pomegranate polyphenol tannins found in pomegranate extract, while large and diverse, is comprised of a relatively small number of building blocks that vary in number of repeating units and combinations. These building blocks are based, in part, on glucose as a sugar and gallic acid as the simplest phenolic monomer (glycone). When gallic acid dimerizes, the two bound molecules form ellagic acid. When ellagic acid dimerizes, it forms gallagic acid, which is essentially four gallic acids. When glucose is incorporated into the structure, gallotannins and ellagitannins are formed. As the complexity or size of the molecule increases, a large combination of the simple building blocks form an array of polyphenol tannins such as ellagitannins (based on repeating units of ellagic acid) and gallotannins (based on repeating units of gallic acid). Collectively, the various combinations form oligomers, which are short polymers consisting of only a few monomer units (gallic acid or ellagic acid or a combination). Punicalin is a monomeric hydrolysable polyphenol containing gallagic acid and glucose. Punicalagin is a monomeric hydrolysable polyphenol containing gallagic acid, ellagic acid and glucose.

Figure 28:
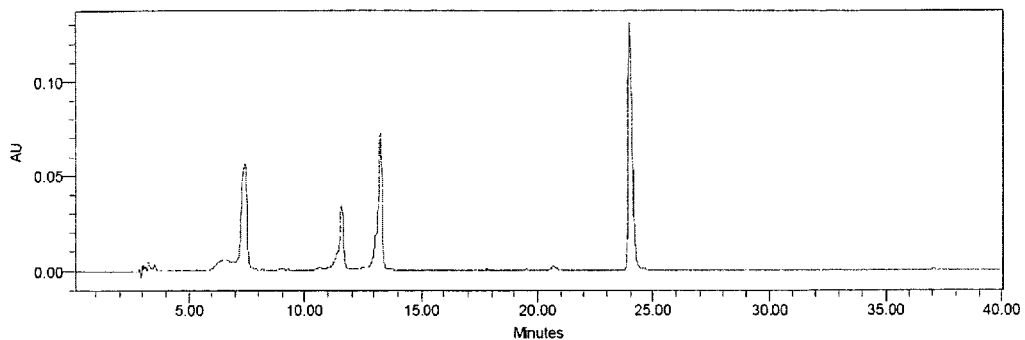
FIG. 28 illustrates a series of chromatograms showing a standard of punicalin, punicalagin A & B and Ellagic Acid, against the profile for the pomegranate extract POMx™ made using the pomegranate Wonderful variety.
Figure 28:
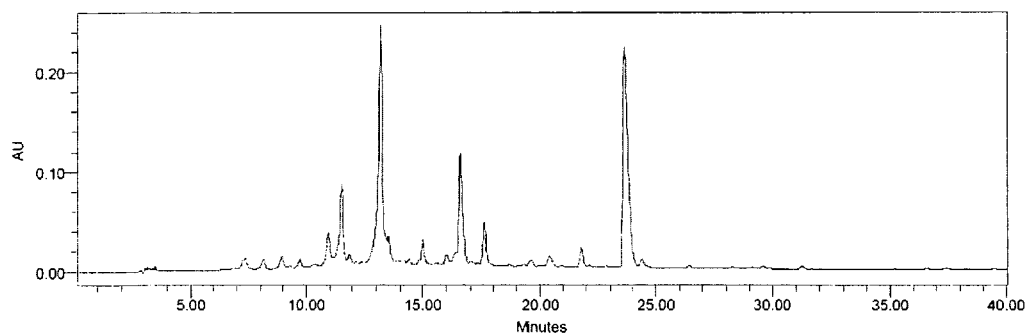
Figure 28:
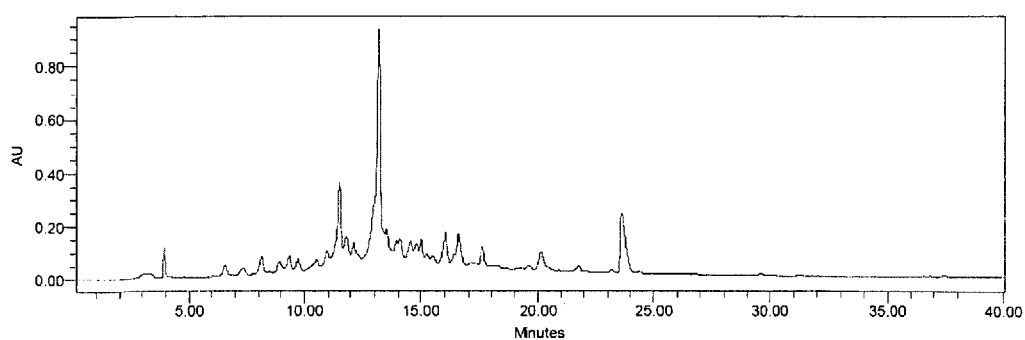

POMx™ is an extract made using the Wonderful variety of *Punica granatum* is a possible pomegranate extract to use in accordance with one or more embodiments of the invention. A series of chromatograms showing a standard of punicalin, punicalagin A & B and ellagic acid, against the profile for the pomegranate extract POMx™ made using the Wonderful variety is depicted at FIG. 28. The chromatograms were obtained from HPLC with a conventional C18 column with flow rate of 0.75 mL/min and mobile phase of a mixture of acetonitrile and 0.4% phosphate buffer in water.

For the process of obtaining pomegranate seed oil 116, pomegranate solids 104 undergo separating step 110 using any conventional method of separating pomegranate seeds 111 from pomegranate solids. Any resulting pomegranate solids after separating step 110 may go into disrupting step 105 for obtaining pomegranate extract 109. Pomegranate seed 111 undergo seed processing step 112 to clean, dry, and flake pomegranate seeds. In short, pomegranate seeds are cleaned of unwanted materials such as pulp and skin fragments, dried to contain 5-8% moisture content or less than 8% moisture content, and then flaked by any conventional method to convert pomegranate seeds into particles. Pomegranate particles undergo extracting step 113 to draw forth seed oil using solvent extraction process and/or applying an external pressure. Crude seed oil from step 113 undergoes stabilizing step 114 in a two-fold process of refining and bleaching. The refining process is to free the extracted pomegranate seed oil from impurities and/or unwanted material. The impurities may be caustic, black sediment, or otherwise undesirable material. The bleaching aspect of the stabilizing process which generally lightens or removes color from the pomegranate seed oil. Any suitable type of antioxidants may be optionally added to further stabilize pomegranate seed oil. Stabilized seed oil undergo deodorizing step 116 which remove unpleasant qualities of pomegranate seed oil such as its offensive odor when extracted in raw form. Deodorizing is generally carried out by placing seed oil under vacuum pressure (e.g., 18-28 mm Hg) and heating the seed oil to a set temperature (e.g., 180-210° C.) for a set time such as 30-120 minutes and sparging using steam or nitrogen gas. Stabilized seed oil after deodorizing step 115 results in a stable and deodorized form of pomegranate seed oil 116 suitable in embodiments of the invention. After the process of manufacture, pomegranate seed oil may be chilled and/or stored frozen.

In such case when antioxidants are not used to stabilize a composition and/or when it is desirable to prevent oxidation or rancidity, pomegranate seed oil or skin care composition containing pomegranate-derived compositions may be stored in an airless container or airless dispensing pump. Any type of airless dispensing system or container may be used to store the composition while at the same time minimizes contact with sources of contamination such as air. Such airless dispensing system includes any airless dispensers suitable for dispensing cosmetic or pharmaceutical products.

Skin Care Composition

Skin care compositions of one or more embodiments of the invention may be topically applied to enhance the general health, vitality and appearance of the skin.

The conditions of aging or adverse skin conditions may result from free radical damage, environmental agents, pollutants, diet, chronological aging, premature aging, hormonal aging, photoaging, or combinations thereof. Accordingly, the skin care compositions and methods selected for improved anti-aging characteristics or adverse skin conditions may employ topical application of pomegranate-derived compositions inhibiting enzymes or mediators that accelerate or facilitate aging, damage, formation of free radicals, or breakdown of skin elements, including, but not limited to metalloproteinases, collagenases, elastases, hyaluronidases, and proteases. The pomegranate-derived compositions may have anti-oxidant, free radical scavenging, anti-comedogenic, anti-microbial and/or anti-inflammatory activity and/or they may restore levels of or inhibit breakdown of aquaporins (AQPs), collagen, elastin, fibronectin, hyaluronic acid, glycosaminoglycans (GAG), other extracellular matrix elements or regulatory enzymes, or mediators of signal transduction pathways (e.g., NF-kB). The active agents may also inhibit other signal transduction pathways and/or cell proliferation pathways associated with aging, including the mediators and regulators associated with these pathways, or combinations thereof.

One or more embodiments of the invention provides a method for preventing, arresting, reversing, ameliorating, diminishing, reducing or improving a sign of aging, in which a composition of the one or more embodiments of invention is topically applied to skin in a cosmetically effective amount sufficient to prevent, arrest, reverse ameliorate, diminish, reduce or improve a sign of aging in skin. Exemplary signs of aging include, but are not limited to, facial lines, fine lines, wrinkles, crow's feet, dark eye circles, blemishes, age spots, stretch marks, or combinations thereof.

In one or more embodiment of the invention provide methods for preventing, arresting, reversing, ameliorating, diminishing, reducing or improving a sign of aging, in which a composition of the invention is topically applied to skin in a cosmetically effective amount sufficient to prevent, arrest, reverse ameliorate, diminish, reduce or improve a sign of aging in skin. Exemplary signs of aging include, but are not limited to, facial lines, fine lines, wrinkles, crow's feet, dark eye circles, blemishes, age spots, stretch marks, or combinations thereof.

In another embodiment, the present invention provides a method for improving the aesthetic appearance of skin, in which a composition of the present invention is topically applied to skin in a cosmetically effective amount sufficient to improve the aesthetic appearance of the skin. The improvements may relate to skin thickness, elasticity, resiliency, moisturization, tone, texture, radiance, luster, brightness, clarity, contour, firmness, tautness, suppleness, softness, sensitivity, pore size, or combinations thereof.

The improvements may further relate to improving adverse skin conditions affected by, resulting in or resulting from conditions such as psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

One or more embodiments of the invention also includes methods of treating wound by topically applying the cosmetic compositions. In use, a small quantity of the composition, for example from 1 to 100 ml, may be applied to exposed areas of the body, from a suitable container or applicator and, if necessary, it is then spread over and/or rubbed into the skin using the hand or fingers or a suitable device.

Pomegranate-derived compositions can be used as solutions, suspensions, dispersions, or pastes incorporated into a variety of formulations for systemic or topical administrations. The pomegranate-derived compositions are generally obtained without fermentation (oxidation) and excessive heat treatment. The skin care compositions of the invention may be formulated in any convenient form suitable for topical application to the skin. Such forms include aerosol, cream, emulsion, solid, liquid, dispersion, foam, gel, lotion, mousse, ointment, powder, patch, pomade, solution, pump spray, stick, or towelette. A typical cosmetic form is a cream that is an oil-in-water emulsion. Water-in-oil and water-in-silicone emulsions are also contemplated.

Optionally, the skin care composition may additionally include one or more anesthetics, anti-allergenics, anti-irritants, antifungals, anti-microbials, anti-inflammatory agents, antiseptics, chelating agents, colorants, depigmenting agents, emollients, emulsifiers, film formers, fragrances, humectants, insect repellents, lubricants, moisturizers, pharmaceutical agents, photostabilizing agents, preservatives, skin protectants, skin penetration enhancers, sunscreens, stabilizers, surfactants, thickeners, viscosity modifiers, or any combinations thereof.

Embodiment of the invention may be used in any cosmetically acceptable vehicle. Examples of cosmetically acceptable vehicles suitable of all embodiments of the invention include, but are not limited to, encapsulant, water, C1-C4 alcohols, fatty alcohols, fatty ethers, fatty esters, glycerin, glycols, vegetable oils, mineral oils, lecithin, hydrogenated lecithin, liposomes, laminar lipid materials, phospholipids, polyglycols, polyols, propyl alcohol, silicone oils, vegetable oil, or any combinations thereof.

The pharmaceutically or cosmetically acceptable vehicle in one or more embodiments of the invention may be in the form of a homogeneous phase formulation or in the form of an emulsion or microemulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semisolid (such as gel and stick); and aqueous based gel and mousse system.

The cosmetically acceptable vehicle will usually contain from about 5% to about 99.9% by weight of the total composition, desirably from about 50% to about 95%, and more desirably from about 80% to about 90% by weight of the composition, and may, in the absence of other cosmetic adjuncts, form the balance of the composition.

One or more embodiments of the invention also includes methods of treating skin by topically applying the cosmetic compositions. In use, a small quantity of the composition, for example from 1 to 100 ml, may be applied to exposed areas of the skin, from a suitable container or applicator and, if necessary, it is then spread over and/or rubbed into the skin using the hand or fingers or a suitable device.

The pharmaceutically or cosmetically acceptable vehicle in one or more embodiment of the invention include, as non-limiting examples, absorbing gums or polymers, or encapsulants. Examples of such encapsulants, for example, may comprise wall-forming and plasticizing materials, such as ethylene oxide and butylene oxide copolymers, mono-, di- or polyvinyl acetates, polyvinylalcohols, proteins or pectins, amphiphilic molecules or lipids, polymethyl methacrylates, or biopolymers such as algin, carrageenan, and chitosan. The encapsulation may be performed, for instance, using techniques such as shear-mixing, spray-drying, agglomeration or extrusion; or consist of coating encapsulation, including coacervation and complex coacervation techniques.

U.S. patent application Ser. No. 11/687,480 is hereby incorporated by reference.

One or more embodiment of invention provides compositions including lipid vesicles incorporating pomegranate-derived compositions (e.g., pomegranate seed oil). The vesicles containing pomegranate-derived composition are useful for administering the actives to a subject. Any lipid vesicles suitable for encapsulating pomegranate-derived compositions, and for administering to the skin of a mammalian subject may be used.

Pomegranate-derived compositions to be encapsulated within lipid vesicles or any encapsulant can be any suitable form, e.g., a preparation of pomegranate juice concentrate, pomegranate extract, pomegranate seed oil, or any combination thereof. Also, encapsulation can provide a means for stabilizing actives that otherwise are labile in certain environments, e.g., for actives that are susceptible to hydrolysis or degradation by interaction with other materials in the formulation.

Vesicles of the invention are vesicles having one or more lipid bilayer membranes surrounding a cavity. Lipid vesicles for use in the invention are typically in the range of about 50 to about 950 nm in size. The lipid vesicles of the invention can include non-phospholipid surfactants. They can also include a charge-producing agent and a targeting molecule. Thus, vesicles made of non-phospholipid "membrane mimetic" amphiphiles are useful in the invention. These are molecules that have a hydrophilic head group attached to a hydrophobic tail and include long-chain fatty acids, long-chain alcohols and derivatives, long-chain amino and glycerolipids. In the bilayers, the fatty acid tails point into the membrane's interior and the polar head groups point outward. The polar groups at one surface of the membrane point towards the vesicle's interior and those at the other surface point toward the external environment. As a vesicle forms during its manufacture, any water-soluble molecules that have been added to the water are incorporated into the aqueous spaces in the interior of the spheres, whereas any lipid-soluble molecules added during vesicle formation are incorporated into the core of the vesicles.

Paucilamellar vesicles that can be formed from many biocompatible, single-tailed amphiphiles are preferred for use in the invention. Such paucilamellar lipid vesicles include non-phospholipid vesicles having one or several lipid bilayer membranes surrounding a large amorphous core in which a chemical entity of interest (i.e., pomegranate-derived composition) is encapsulated.

Non-phospholipid paucilamellar lipid vesicles are sold under the trade name Novasome™ (IGI Inc., Buena, N.J.). Several Novasome™ formulations exist (e.g., Novasome™ A, Novasome™ D, Novasome™ Day Cream).

Novasome™ vesicles are useful for encapsulating chemical ingredients to aid in formulation, increase delivery to site of action and stabilize chemical ingredients in the formulation. These lipid vesicles are generally about 200-700 nanometers in size, depending upon a wide variety of membrane constituents individually chosen for each particular purpose. Their size distribution is uniform, and encapsulation efficiency can be nearly 100% for lipid cargo and 85% for aqueous materials. Finely divided insoluble particles (e.g., insoluble pharmaceuticals) can also be encapsulated.

Novasome™ vesicles are inherently stable, and can be tailored to be stable at pH levels ranging from 2-13 as well as temperature ranges as low as liquid nitrogen to above the boiling point of water. They can be stable to solvents including alcohols, ethers, esters, gasoline, diesel and other fuels. They can encapsulate fragrances and flavors which contain volatile and fragile ethers, esters, aldehydes, etc. These vesicles can release their cargo under varying physical and chemical circumstances including heat, light, pH changes, enzymatic degradation, drying transmembrane diffusion, etc.

Protocols for producing and administering Novasome™ formulations are described, for example, in U.S. Pat. Nos. 4,855,090; 4,911,928; 5,474,848; 5,628,936; 6,387,373; Hollick et al., British Journal of Dermatology 149:1365-2133, 2003; Gupta et al., Vaccine 14:219-225, 1996; and Wallach D F H and Philippot J., New Type of Lipid Vesicle: Novasome™ In: Liposome Technology, 2nd ed., Gregorriadis G., CRC Press, Boca Raton, Fla., 1982, pp. 141-151; Niemiec et al., Pharmaceutical Research 12:1184-1188, 1995; and Alfieri D R, Cosmetic Dermatology 10:42-52, 1997.

In one or more embodiments, the vesicles are those used in skin cream.

Methods for producing and using lipid vesicles are described, e.g., in U.S. Pat. Nos. 4,917,951 and 5,013,497; Walde P. and Ichikawa S., Biomol Eng., 18:143-177, 2001; Hunter D. G. and Frisken B. J., Biophys J., 74:2996-3002, 1998; and Cevc G. Adv Drug Deliv Rev., 56:675-711, 2004.

In certain embodiments of the subject invention, the lipid vesicles (e.g., non-phospholipid paucilamellar lipid vesicles) may also include targeting molecules, either hydrophilic or amphiphilic, which can be used to direct the vesicles to a particular target in order to allow release of at least one pomegranate-derived composition within the vesicle at a specified biological location. If hydrophilic targeting molecules are used, they can be coupled directly or via a spacer to an OH residue of the polyoxyethylene portion of the surfactant, or they can be coupled, using techniques in the art, to molecules such as palmitic acid, long chain amines, or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Typical amphiphilic targeting molecules may be neutral glycolipids, galactocerebrosides, or charged glycolipids such as gangliosides.

In one or more embodiments of the invention, charge-producing materials and steroids such as cholesterol or hydrocortisone or their analogues and derivatives are used in the formation of the lipid vesicles (e.g., paucilamellar lipid vesicles). Preferred charge-producing materials include negative charge-producing materials such as dicetyl phosphate, cetyl sulphate, phosphatidic acid, phosphatidyl serine, oleic acid, palmitic acid, or mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. Another example of a positive charge-producing material is hexadecyl trimethylammonium bromide, a potent disinfectant.

Lipid vesicles used according to the subject invention can be any of a large variety of lipid vesicles and can be made according to any of a large number of production methods. In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically agent materials is then added to the film. Large multilamellar vesicles are produced upon agitation. When smaller multilamellar vesicles are desired, the larger vesicles are subjected to sonication, sequential filtration through filters with decreasing pore size or reduced by other forms of mechanical shearing. Lipid vesicles can also take the form of unilamellar vesicles, which are prepared by more extensive sonication of multilamellar vesicles, and consist of a single spherical lipid bilayer surrounding an aqueous solution. A comprehensive review of all the aforementioned lipid vesicles and methods for their preparation are described in "Liposome Technology", ed. G. Gregoriadis, CRC Press Inc., Boca Raton, Fla., Vol. I, II & III (1984). For methods of preparing lipid vesicles, also see U.S. Pat. Nos. 4,485,054, 4,761,288, 5,013,497, 5,653,996, and 6,855,296.

To prepare non-phospholipid paucilamellar lipid vesicles formed of non-phospholipid surfactant material and containing an aqueous-based pomegranate-derived composition, any suitable method can be used. Methods of preparing non-phospholipid paucilamellar lipid vesicles typically involve first forming a lipophilic phase by combining several lipophilic components including surfactant material and then heating and blending this mixture. Examples of suitable surfactant materials include but are not limited to polyoxyethylene (2) cetyl ether, polyoxyethylene (4) lauryl ether, glyceryl monostearate, and poly oxyethylene (9) glyceryl stearate. The resultant lipophilic phase is then blended with an aqueous phase having an aqueous buffer and an aqueous soluble collagen formulation, under shear mixing conditions, to form the paucilamellar lipid vesicles. In this method, the temperature of the lipophilic phase is elevated in order to make it flowable followed by carrying out the shear mixing between the lipophilic phase and the aqueous phase at a temperature such that both phases are liquids. While it is often desirable to use the same temperature for both phases, this is not always necessary. Any other methods can also be used. Typical methods for making the paucilamellar lipid vesicles of the invention are described in U.S. Pat. No. 4,911,928.

To encapsulate oil-based pomegranate-derived composition within paucilamellar lipid vesicles, for example, the pomegranate seed oil formulation is dispersed in an oil or wax forming an oily phase. The oil or wax is a water immiscible oily solution selected from a group consisting of oils, waxes, natural and synthetic triglycerides, acyl esters, and petroleum derivatives, and their analogues and derivatives. The oily phase containing the oil-dispersible material is mixed with the lipid phase and the combined oil-lipid phase is blended under shear mixing conditions with the aqueous phase. Surfactants useful in the encapsulation process are the same as those used to make paucilamellar lipid vesicles with an aqueous core.

Paucilamellar lipid vesicles can be made by a variety of devices which provide sufficiently high shear for shear mixing. Many such devices are available on the market including a Microfluidizer™ such as is made by MicroFluidics Corp. (Newton, Mass.), a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the pomegranate-derived composition-containing paucilamellar lipid vesicles of the present invention.

A device which is particularly useful for making the paucilamellar lipid vesicles of the present invention has been developed by Micro Vesicular Systems, Inc., (Vineland, N.J.) and is further described in U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core paucilamellar lipid vesicles are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. Typically, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. In most circumstances, turbulent flow is selected to provide adequate mixing.

No matter what device is used to form the paucilamellar lipid vesicles, if proper shear mixing is achieved they have a structure involving a large, unstructured amorphous center surrounded by a plurality of lipid bilayers having aqueous layers interspersed there between. About four lipid bilayers is standard with 2-8 possible. The amorphous center may be entirely filled with an aqueous material, e.g., a buffer and any aqueous material to be encapsulated, or may be partially or totally filled with an oily material, forming lipid-core paucilamellar lipid vesicles. If an aqueous center is used, the paucilamellar lipid vesicles will normally range in diameter from about 0.5-2 µm while if an oily center is used, the size may increase to up to about 15-20 µm depending upon the amount of oil used.

The following non-limiting examples further illustrate embodiments of the invention.

EXAMPLE 1

Preparation of PJC

The following procedure was used to produce pomegranate juice concentrate (PJC).

Pomegranates were picked by hand, washed, chilled to 32° F., and stored in tanks. Then the fruit was crushed, squeezed, and enzymatically treated with pectinase to yield the pomegranate juice and the pomegranate solids byproducts, which include the pericarp, the inner membrane and the seeds. Pectinase hydrolyzes alpha-1.4 galacturonide bonds in pectin and, thus, it improves extraction and filtration, and prevents formation of pectin gels. The juice was filtered, pasteurized, concentrated, and stored at −18° C.

Alternatively, pomegranates were picked by hand, washed, and stored in tanks. Then, the fruits were crushed and squeezed. The juice was filtered, pasteurized, concentrated, and stored as PJC at −18° C.

The PJC may be diluted 1:5 (v:v) with water in order to obtain a single strength pomegranate juice.

EXAMPLE 2

Preparation of PE

The following procedure was used to produce pomegranate extract (PE).

The starting material for the production of the extract is the pomegranate solids, which generally comprise the pericarp, the inner membrane and the seeds of the pomegranate. The pomegranate solids were obtained and collected after the primary juice from the arils had been substantially expelled or otherwise removed from the pomegranate by pressing, crushing, or any other methods for extracting pomegranate juice.

The pomegranate solids were then transferred to three Reitz Mills with ⅜-inch screens. The material was milled to a fine puree and heated to approximately 125° F. This step, coupled with the following enzyme addition, assisted in breaking down the colloidal structure of the remaining pomegranate solids, thereby releasing the remaining soluble solids.

The mixture was heated to a temperature of about 125° F. for two hours. Three enzymes were added to the mixture: pectinase (Rohapect™ DA6L), cellulase/pectinase (Rohapect™ CL), and hemi-cellulase/pectinase (Rohapect™ B1L). These enzymes were used to liberate the remaining pomegranate soluble solids, such as sugars, minerals, anthocyanins, and remaining polyphenols.

The mixture was then pumped from the extraction plant to the primary processing plant where it was held in the mash treatment tanks for approximately one hour. After one hour, 50-100 pounds of bentonite in a 125 gallon water slurry, per 8,000 gallons of the mixture, was added for protein removal. The treated mixture was then passed through a Westphalia 755 Decanter for removal of solids. The residual insoluble material was discharged as waste.

The remaining liquid extract was processed in a Schmidt evaporator. In this step, the extract was stripped and rectified. In addition, the liquid extract was pre-concentrated and then pasteurized to 205° F. for 45 seconds. The liquid extract then exited the evaporator and was filtered on Koch Micro-Filtration membranes at a 4,500 Da molecular weight cut-off for liquid extract soluble solids.

The liquid extract then re-entered the evaporator for final concentration. Initial heat on this step was about 185-195° F. At about 70° Brix, the liquid extract was cooled to less than about 45° F. and pumped to the concentrate batching room where it was blended and standardized at 70° Brix which results the pomegranate extract (PE) used in embodiments of the inventions.

EXAMPLE 3

Preparation of PSO

The following procedure was used to produce pomegranate seed oil (PSO).

Pomegranate seeds are separated from a mash of pomegranate fruit after the pressing step (crushing and squeezing) in the Example 1. Pomegranate seeds are processed in a forced air dryer for purposes of removing moisture from the pomegranate seeds from which the seed oil is to be extracted. The set temperature range of 80-110° C. is generally acceptable for achieving the proper level of drying when drying is done for a duration of 3 to 9 hours to yield seeds with 5-8% or less than 8% moisture content Dried pomegranate seeds can contain dried pulp and skin fragments. It is generally beneficial to further process dried pomegranate seeds to remove these unwanted materials from the pomegranate seeds. Removal of unwanted dried material is carried out by placing pomegranate seeds onto a shaker deck. An air aspirator is also helpful when seeking to remove these unwanted materials. When using an air aspirator application is typically performed under a vacuum of 1.2" of water to yield cleaned dried seed free of pulp and skin fragments. The removal of unwanted material before solvent oil extraction can yield oil that is lighter in color requiring a less rigorous bleaching regimen.

The conversion of pomegranate seed into particles may be referred to as flaking. The conversion into particles may occur prior to solvent extraction with pomegranate seeds tempered to 12-16% moisture content by using steam and adjusting temperature to 70° C. The flaking may produce ~0.5 mm flakes. Flaking is carried out in accordance with one or more embodiments of the invention by heating the pomegranate seed to a temperature between 47-53° C. Pre-heating the pomegranate seed to 50±3° C. in the cooker section of a cooker pre-press is generally advisable followed by flaking immediately thereafter using a roller gap width setting of 0.2 mm or other setting acceptable to accomplish the goal of flaking. In the case that seed flaking results in excessive production of fines the moisture content may be adjusted by applying steam and changing the temperature to 70° C. For instance, ideal flaking conditions may produce large consistent flakes, 0.50±0.5 mm in thickness and 13.0±0.5% moisture content. From a 325 kg batch of tempered seed a yield of 310.9 kg of flaked pomegranate seed may be produced.

Extraction of seed oil from flaked pomegranate seed is generally accomplished by applying external pressure and/or through the use of solvent extraction using iso-hexane. For example, 2-methylpentane(isohexane) generally serves as a reliable solvent for extracting the seed oil. The drawing forth of seed oil from flaked pomegranate seed may be carried out by solvent extraction using 2-methylpentane(isohexane) with 50-1,000 ppm tocopherols or other natural antioxidants such as Rosemary or synthetic antioxidants such as BHA/BHT. The solvent extraction may be carried out using an extractor (such as a Soxhlet) wherein pomegranate seed flakes can be loaded in to the screen sample holder and extracted for four hours to result in an extraction yield of greater than 95%. The solvent extraction may be carried out in 1-methyl pentane on a counter-current extractor (such as Crown) under effective operating conditions. The effective operating conditions for a counter-current extractor may be the following: Flake feed rate 65 Kg/h, Retention time of 60 minutes, Bed level setting at minimum, fresh solvent flow 150±5 Kg/h, Solvent temperature 52±4° C., RFE feed rate 21 μm, RFE steam pressure 13 psi, DT sparge steam off, DT top tray temperature 84±3° C., DT bottom tray temperature 100±2° C. The solvent extraction may contain the addition of mixed tocopherols to 1-methyl pentane to minimize oxidation of the oil. Mixing in tocopherols or other antioxidants may be added at a quantity of 50 to 1,000 ppm. The extraction may yield crude oil that has a PV of 0.69, FFA of 1.54%, and Lovibond color parameters (1 inch sample cell) 70.0Y and 2.9R.

Stabilizing pomegranate seed oil requires a two-fold process of refining and bleaching the crude pomegranate seed oil. The general objective in refining is to free the extracted pomegranate seed oil from impurities and/or unwanted material. The impurities may be caustic, black sediment, or otherwise undesirable material. Stabilizing the crude pomegranate seed oil may require caustic refining. The stabilization may involve water washing and require assessment of the need for refining the oil; Free fatty acid (FFA) values may indicate a need for caustic refinement of the oil. FFA values may be near 1.54% indicating a need for further refinement. Such refining is generally carried out by heating the crude pomegranate seed oil to 65° C. and adding 0.1% phosphoric acid. The mixture of crude pomegranate seed oil and phosphoric acid may then be mixed for 15 minutes and sodium hydroxide (18 Be) may be added at 1-4% of the starting oil weight. Refining is carried out by heating the crude pomegranate seed oil to 65° C. and adding 0.1% phosphoric acid. The mixture of crude pomegranate seed oil and phosphoric acid may then be mixed for 15 minutes and sodium hydroxide (18 Be) may be added at 1-4% of the starting oil weight. The mixture may then be clarified by heating to 40 to 50° C. and applying centrifugation to remove undesirable black sediment and other impurities from the oil. After the clarifying 15% water (w/w) may be added and mixed for 15 minutes at 75° C. Oil may be recovered from water wash by centrifugation. This process may yield an FFA value of the caustic refined and water washed oil of less than 0.5%. The refining process may include a winterization step wherein refrigeration is applied to facilitate wax removal.

The bleaching aspect of the stabilizing process generally lightens or removes color from the pomegranate seed oil. This process of lightening or removal of color is generally referred to as bleaching. The bleaching may be carried out using bleaching clay or activated carbon, applying heat and adding citric acid and mixing and pre-heating oil to 65° C. Quantities of 0.2% citric acid are typically effective when mixing. A filter aid (e.g. cellulose acetate) and mixing is also beneficial. When adding clay 0.5-5% clay at 75-115° C. for 10-60 minutes in a reactor under full vacuum is effective. Cooling the oil to 50 to 80° C. and filtering also produces results. While any means for bleaching is acceptable, bleaching is generally carried out in a reactor (such as Parr) using various grades of bleaching clay and may undergo the following exemplary steps. Oil may be pre-heated to 65° C. and 0.2% citric acid may be added and mixed for 15 minutes. Trisyl S615 filter aid (0.2% w/w) may be added and mixing continued for another 15 minutes. Bleaching clay (%3, w/w) may then be mixed into the oil and the reactor sealed. Bleaching may be performed at 95° C. for 30 minutes under full vacuum. The oil may then be cooled to 65° C. and filtered. The bleaching may be carried out using bleaching clay such as Tonsil Supreme 124FF and undergo the following steps: Oil can be heated to 65° and 0.2% citric acid added and mixed for 15 minutes. Trisyl S615 filter aid (0.2%, w/w) can be added and mixing continued for an additional 15 minutes. Bleaching clay (3%, w/w) may then be mixed into the oil and the reactor sealed. Bleaching may be performed at 95° C. for 30 minutes under full vacuum in a mini-RBD bleaching reactor. The oil may then be cooled to 65° C. and filtered. The above mentioned steps may effectively lighten the color of the oil to achieve Lovibond Y and R values of 2.0 and 0.2, respectively.

The stabilized pomegranate seed oil goes through a deodorizing step to remove unpleasant qualities of pomegranate seed oil such as its offensive odor when extracted in raw form. The elimination or prevention of offensive odor of pomegranate seed oil is referred to as deodorizing. Deodorizing is generally carried out by placing seed oil under vacuum pressure (e.g., 18-28 mm Hg) and heating the seed oil to a set temperature (e.g., 180-210° C.) for a set time such as 30-120 minutes and sparging using steam or nitrogen gas. The deodorizing step also involves cooling the seed oil to 40-90° C. and coarse filtering. An antioxidant mixture such as tert-butylhydroxyquinone (TBHQ) at 50-200 ppm, tocopherols at 50-200 ppm and/or ascorbyl palmitate at 50-200 ppm is generally helpful. Other quantities of tocopherol, TBHQ and ascobyl palminate are however also within the scope and spirit of making the PSO. The elimination or prevention of offensive odor of pomegranate seed oil may be carried out by heating the oil using a heating apparatus and vacuum to a target temperature range below 210° C. The deodorization may occur by taking bleached pomegranate seed oil under vacuum pressure (28-30 mm Hg) and heating it to a temperature between 180-210° C. for 30 to 120 minutes. The preferred deodorization residence time range is 30 to 60 minutes.

The stabilized pomegranate seed oil after the deodorizing step yields the pomegranate seed oil (PSO) used in embodiments of the invention.

EXAMPLE 4

Preparation of a Pomegranate-Derived Skin Care Composition

This example illustrates an oil-in-water emulsion according to one embodiment of the invention. Skin cream can also be prepared using some or all of the pomegranate-derived compositions of Examples 1, 2, and 3. To make 100 g of pomegranate-based oil-in-water emulsion:

56.7 g of deionized water is added to a main vessel. 10.0 g of sclerotium gum (e.g., Tinocare® GL (Ciba Specialty Chemicals, Tarrytown, N.Y.)), a thickening and gelling agent, is homogenized in water until uniform. The mixture in the main vessel was then heated to 75°-80° C.

2.0 g of Incroquat Behenyl TMS-50 (CRODA, Edison, N.J.), 1.0 g of Cosmowax P (CRODA, Edison, N.J.), 10.0 g of dimethicone (e.g., Masil SFR 2,000 (Lubrizol, Wickliffe, Ohio), Dow Corning 200 (Dow Corning, Midland, Mich.), Chemsil DM6 (Shin Etsu Silicones of America, Akron, Ohio)) were combined together to make an emulsifying system agent. 13.0 g of the emulsifying system agent and 3.0 g cetyl alcohol (e.g., Alfol 16 Alcohol (Sasol, Houston, Tex.)), an emollient agent, was added to the 75°-80° C. mixture and mixed for about ten minutes until all solids were melted. The mixture is then cooled to 50°-55° C. 7.0 g of PSO from the Example 3 is added to the 50°-55° C. mixture and mixed until uniform.

2.0 g of Hydrovance (National Starch and Chemical, Bridgewater, N.J.) and 5.0 g of Hydrolite-5 (Symrise, Teterboro, N.J.) moisturizing agents were added to the mixture and mixed until uniform. The mixture is then cooled to 40° C.

3.0 g of PJC from the Example 1 and 0.3 g of PE from the Example 2 were combined together, then added to the 40° C. mixture and mixed until uniform. The resulting oil-in-water emulsion is then cooled to 30° C. while mixing.

EXAMPLE 5

Effects of PJC, PE, and PSO on UVB-Induced Aging and Damage in EpiDermFT™ Cells

The effects of PJC of Example 1, PE of Example 2, and PSO of Example 3 were assessed on UVB-irradiated cells. UVB irradiation induced the formation of sunburn cells. For stimulation of skin cells under UVB irridation, EpiDermFT™ (Matek Corp., Ashland, Mass.) was chosen for this study. EpiDermFT™ consists of normal, human-derived epidermal keratinocytes (NHEK) and normal, human-derived dermal fibroblasts (NHFB) which have been cultured to form a multilayered, highly differentiated model of the human dermis and epidermis.

Materials and Methods

EpiDermFT™ tissue samples were transferred onto a six-well plate containing 5 ml of EFT-200-ASY/MM medium (Matek Corp., Ashland, Mass.) overnight under standard cell culture conditions at 37° C. incubator and 5% $CO_2$ in a humid environment. The six-well plate containing tissue samples were topically treated for one hour prior to UVB irradiation in duplicate via gentle pipetting 100 µl of fresh EFT-200-ASY/MM medium containing either PJC (1 or 2 µl/0.1% DMSO/well), PE (0.25 or 0.5 µl/0.1% DMSO/well) or PO (1 or 2 µl/0.1% DMSO/well). After topical treatment, samples were carefully rinsed with PBS, via gentle pipetting of the apical tissue surface to remove any non-absorbed PJC, PE and PSO before UVB irradiation at 60 mJ/cm$^2$ using a custom designed Research Irradiation Unit (Daavlin, Bryan, Ohio) that consists of a fixture mounted on fixed legs. Mounted within the exposure unit are four UVB lamps and the exposure system is controlled by Daavlin Flex Control Integrating Dosimeter.

Tissue samples were harvested 12 hours post-UVB and fixed in 10% neutral buffered formalin for paraffin embedding. 5 mm serial sections of paraffin-embedded tissue sample were mounted on poly-1-lysine coated glass slides (Sigma Chemicals, St Louis, Mo.) for hematoxylin-eosin staining and immunohistochemical evaluation.

For western blot analysis, tissue sample lysate was prepared by keeping the cell in 0.3 ml of lysis buffer (10 mM Tris-HCl, pH 7.4, 150 mM NaCl, 1% Triton X-100, 1 mM EDTA, and 1 mM EGTA) containing 0.2 mM sodium vanadate, 2 mM PMSF, 0.5% NP-40, and 0.2 U/ml aprotinin with freshly added protease inhibitor cocktail at 4° C. for 15 minutes. The cells were scrapped and collected in a microfuge tube and then passed through a 22½-G needle to break up the cell aggregates. The lysates were centrifuged at 13,000×g for 25 min at 4° C. to remove cell debris. Supernatant were collected, and protein estimation was done by BCA method. Equal amount (30-40 µg) of protein was resolved electrophoretically over 12% tris glycine gel, and transferred to a nitrocellulose membrane. The blot containing transferred protein was blocked in blocking buffer (5% nonfat dry milk in 20 mM Tris-buffered saline, pH 7.6 containing 1% Tween20-TBST) for 1 hour at room temperature followed by incubation with appropriate primary antibody in blocking buffer for 2 hours to overnight at 4° C. This was followed by incubation with specific anti-mouse or anti-rabbit secondary antibody conjugated with horseradish peroxidase for 2 hours at room temperature and then washed 3 times, 15 min each in TBST and detected by enhanced chemiluminescence and autoradiography using Blue Lite Autorad film (ISC Bioexpress, Kaysville, Utah).

The bands in western blots were quantitated using densitometry and the results are expressed as relative intensity versus the intensity of normalized untreated and non-UVB-irradiated EpiDermFT™ control tissue sample in the blot.

UVB-Mediated Sunburn Cell Formation

Figure 2:
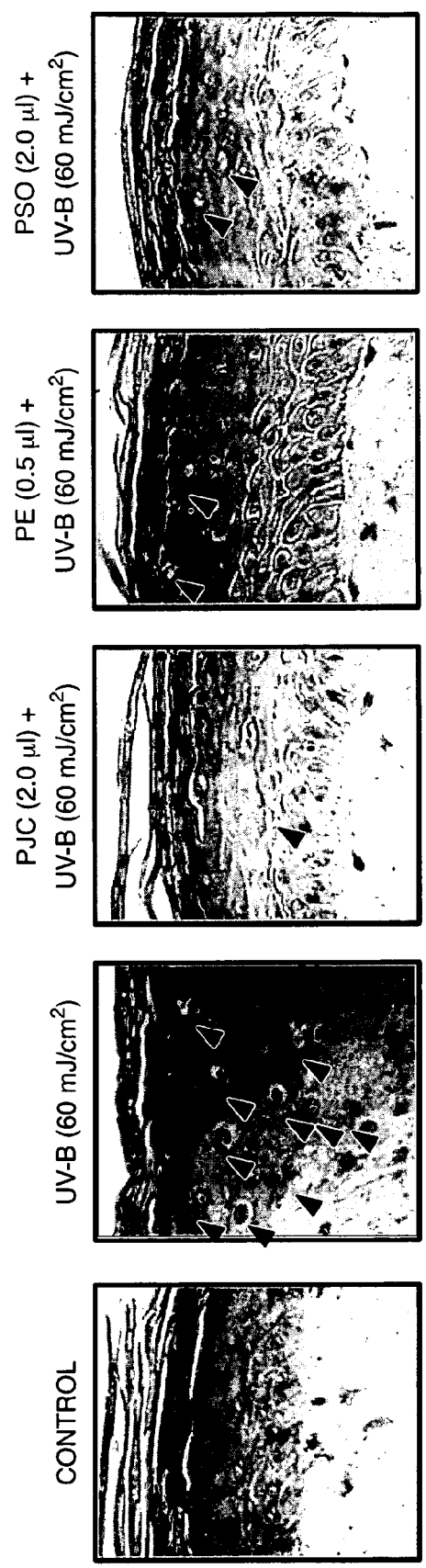
FIG. 2 depicts cross-sections of UVB irradiated skin tissue samples with hematoxylin-eosin staining and pre-treated either with PJC, PE, or PSO. Arrows indicate sunburn cells.

FIG. 2 illustrates the effects of PJC, PE, and PSO on UVB-mediated formation of sunburned cells in EpiDermFT™ tissue samples. Arrows in FIG. 2 indicate sunburn cells. Sunburn cells are morphologically distinct due to cell shrinkage and nuclear condensation, which attributes to their small, dense nuclei and eosinophilic cytoplasm that becomes darker with hematoxylin-eosin stain. Tissue sample exposed to UVB (60 mJ/cm$^2$) alone showed higher number of sunburn cells than tissue sample treated either with PJC, PE, or PSO. For PJC-treated tissue sample, the presence of a sunburn cell is found at the innermost layer of epidermis, adjacent to dermis. For PE-treated tissue sample, sunburn cells are found at near the outermost layer of epidermis, adjacent to stratum corneum. For PSO-treated tissue sample, sunburn cells are generally found at the stratum spinosum layer of epidermis. The PJC, PE, and PSO have a similar effect on inhibiting UVB-mediated formation of sunburn cells. However, the different distribution of sunburn cells in PJC-, PE-, and PSO-treated tissue samples exposed to UVB may indicate different modes of action or differential effects of pomegranate-derived compositions on layers of epidermis.

UVB-Mediated Induction of Matrix Metalloproteinases

Exposure to UVB light to human skin induces oxidative damage and expression of matrix metalloproteinases (MMPs), which have been implicated in the process of photoaging. Photoaged skin is biochemically characterized by an overgrowth of abnormal elastic fibers in the dermis and by a dramatic decrease of distinct collagen types. Matrix metalloproteinases degrade collagens and macromolecules of the extracellular matrix, a hallmark in carcinogenesis and aging. The exposure of human skins to UVB radiation upregulates the synthesis of matrix-degrading enzymes matrix metalloproteinases, such as MMP-1, -2, -3, -7, -8, -9, -11, and -12.

Figure 3:
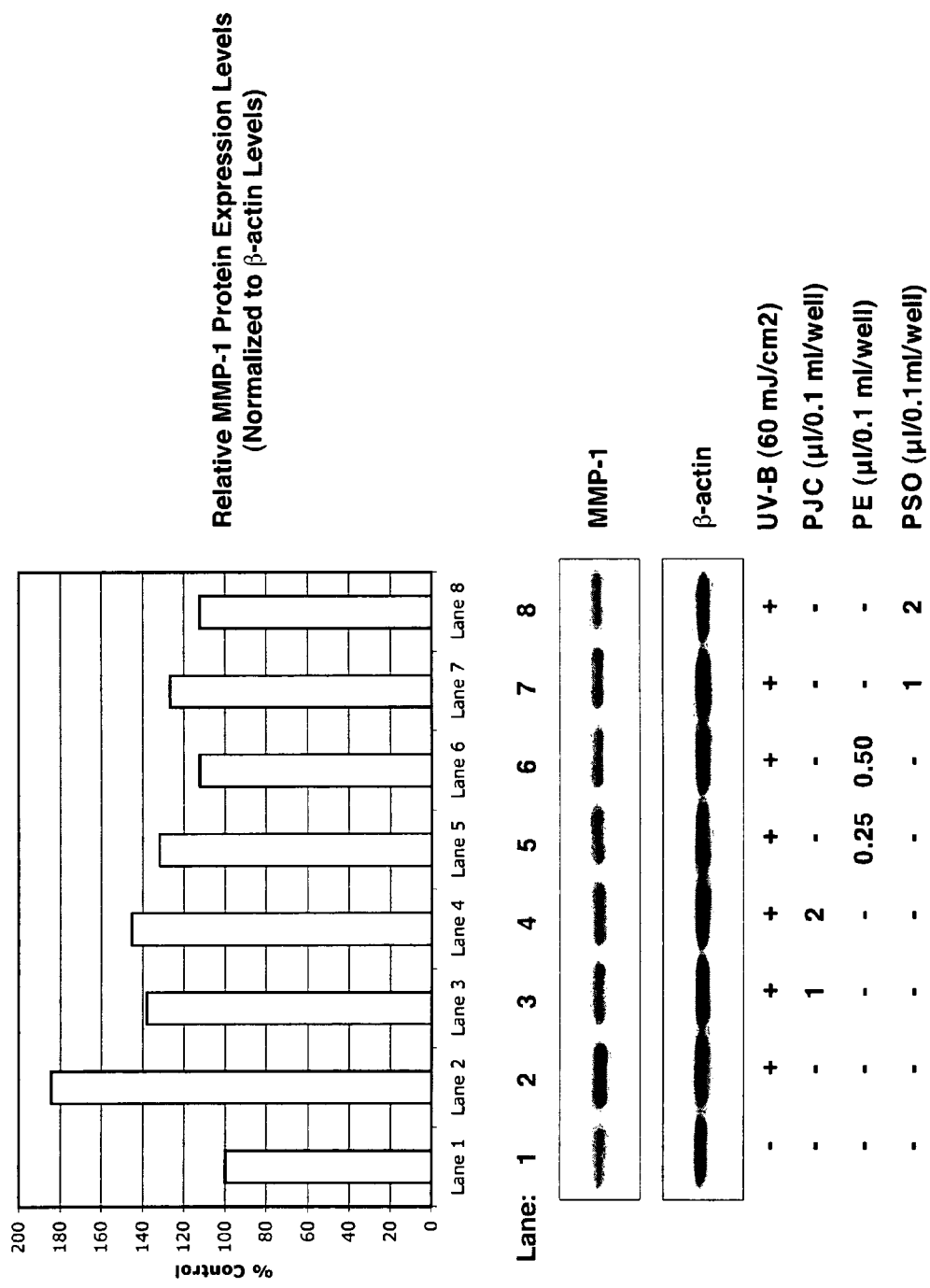
FIG. 3 is a digital composite image containing a bar graph of relative protein expression levels of MMP-1 (interstitial collagenase) and depicting the effects of PJC, PE, and PSO on UVB-mediated induction of matrix metalloproteinases (MMPs) in skin tissue samples.

FIG. 3 illustrates the effects of pomegranate-derived compositions on UVB-mediated induction of MMP-1 protein expression in EpiDermFT™ tissue samples. All UVB-irradiated tissue samples treated with different pomegranate-derived composition showed a similar level of inhibition of MMP-1 protein expression compared to untreated tissue sample.

Figure 4:
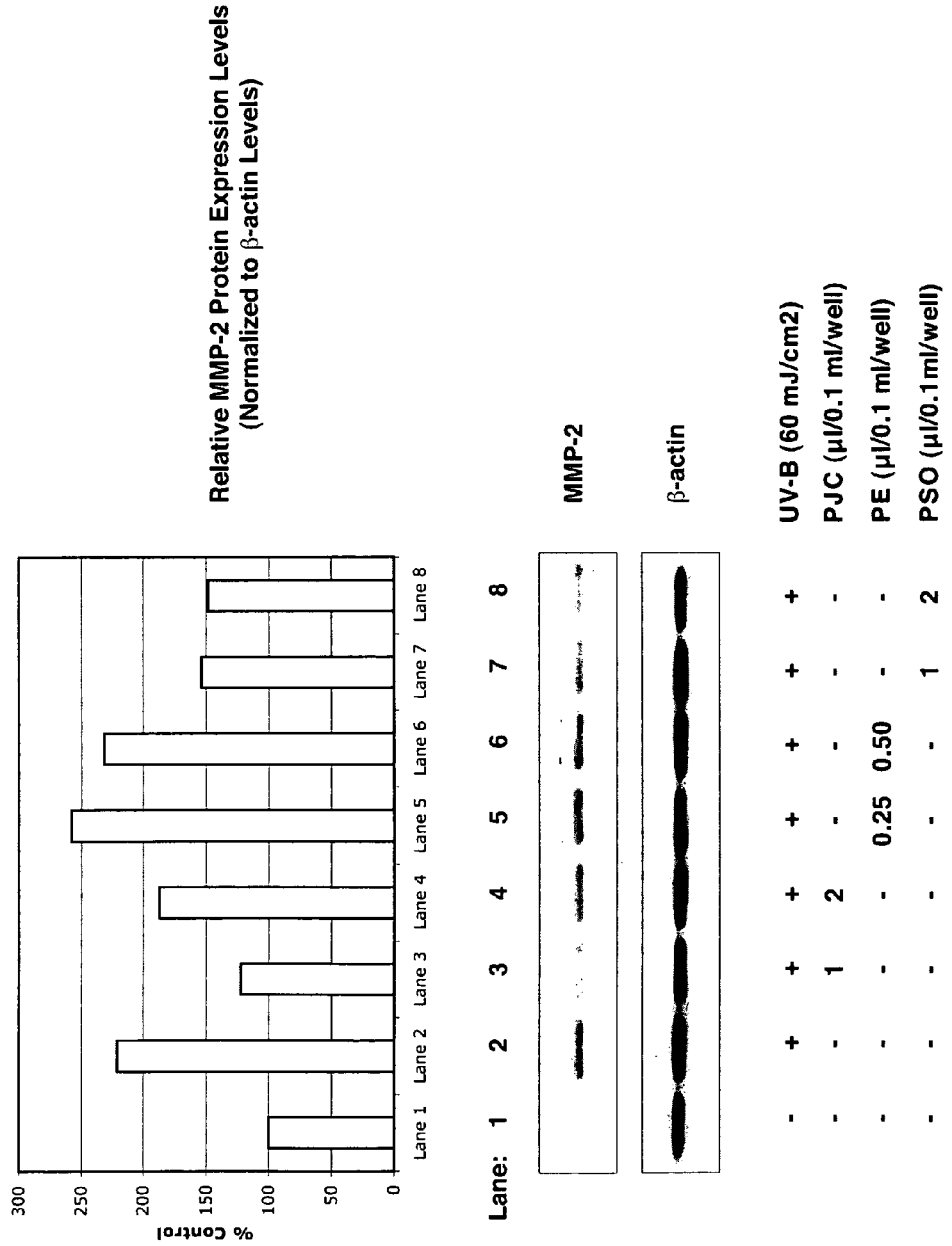
FIG. 4 is a digital composite image containing a bar graph of relative protein expression levels of MMP-2 (gelatinase A) and depicting the effects of PJC, PE, and PSO on UVB-mediated induction of matrix metalloproteinases (MMPs) in skin tissue samples.

FIG. 4 illustrates the effect of pomegranate-derived compositions on UVB-mediated induction of MMP-2 protein expression in EpiDermFT™ tissue samples. UVB-irradiated tissue sample treated with PE appears to have no effect on inhibiting MMP-2 protein expression compared to untreated UVB-irradiated tissue sample whereas PJC- and PSO-treated tissue samples showed a similar inhibitory effect. This is another example of different effects from each of three pomegranate-derived compositions.

Figure 5:
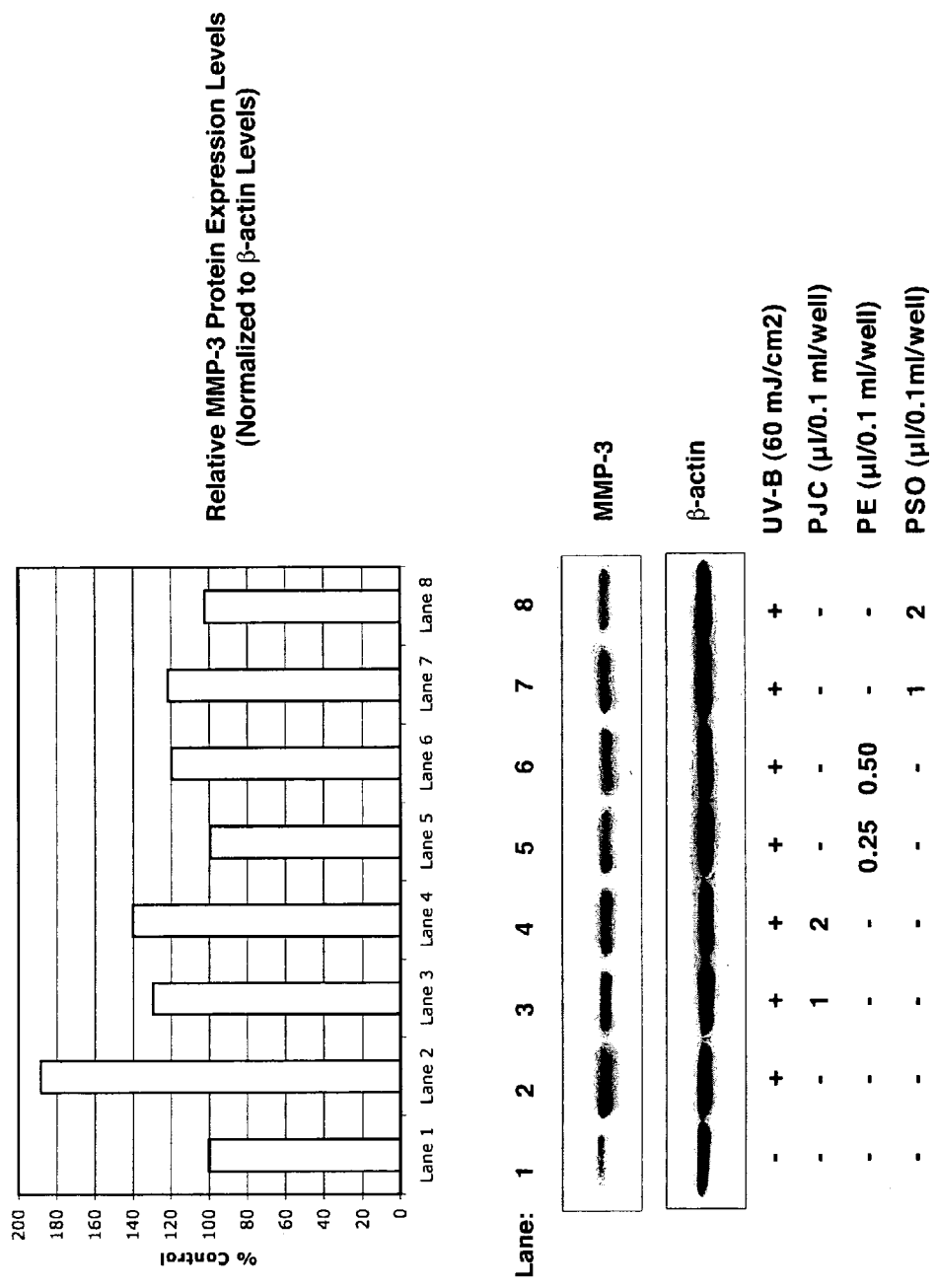
FIG. 5 is a digital composite image containing a bar graph of relative protein expression levels of MMP-3 (stromelysin-1) and depicting the effects of PJC, PE, and PSO on UVB-mediated induction of matrix metalloproteinases (MMPs) in skin tissue samples.

FIG. 5 illustrates the effects of pomegranate-derived compositions on UVB-mediated induction of MMP-1 protein expression in EpiDermFT™ tissue samples. All UVB-irradiated tissue samples treated with different pomegranate-derived composition showed a similar level of inhibition of MMP-1 protein expression compared to untreated UVB-irradiated tissue sample.

FIG. 6 illustrates the effects of pomegranate-derived compositions on UVB-mediated induction of MMP-7 protein expression in EpiDermFT™ tissue samples. All UVB-irradiated tissue samples treated with different pomegranate-derived composition showed inhibition of MMP-7 protein expression compared to untreated UVB-irradiated tissue sample. In this case, PSO has the strongest inhibitory effect on MMP-7 compared to PJC and PE.

FIG. 7 illustrates the effects of pomegranate-derived compositions on UVB-mediated induction of MMP-9 protein expression in EpiDermFT™ tissue samples. All UVB-irradiated tissue samples treated with different pomegranate-derived composition showed a similar level of inhibition of MMP-9 protein expression compared to untreated UVB-irradiated tissue sample.

Figure 9:
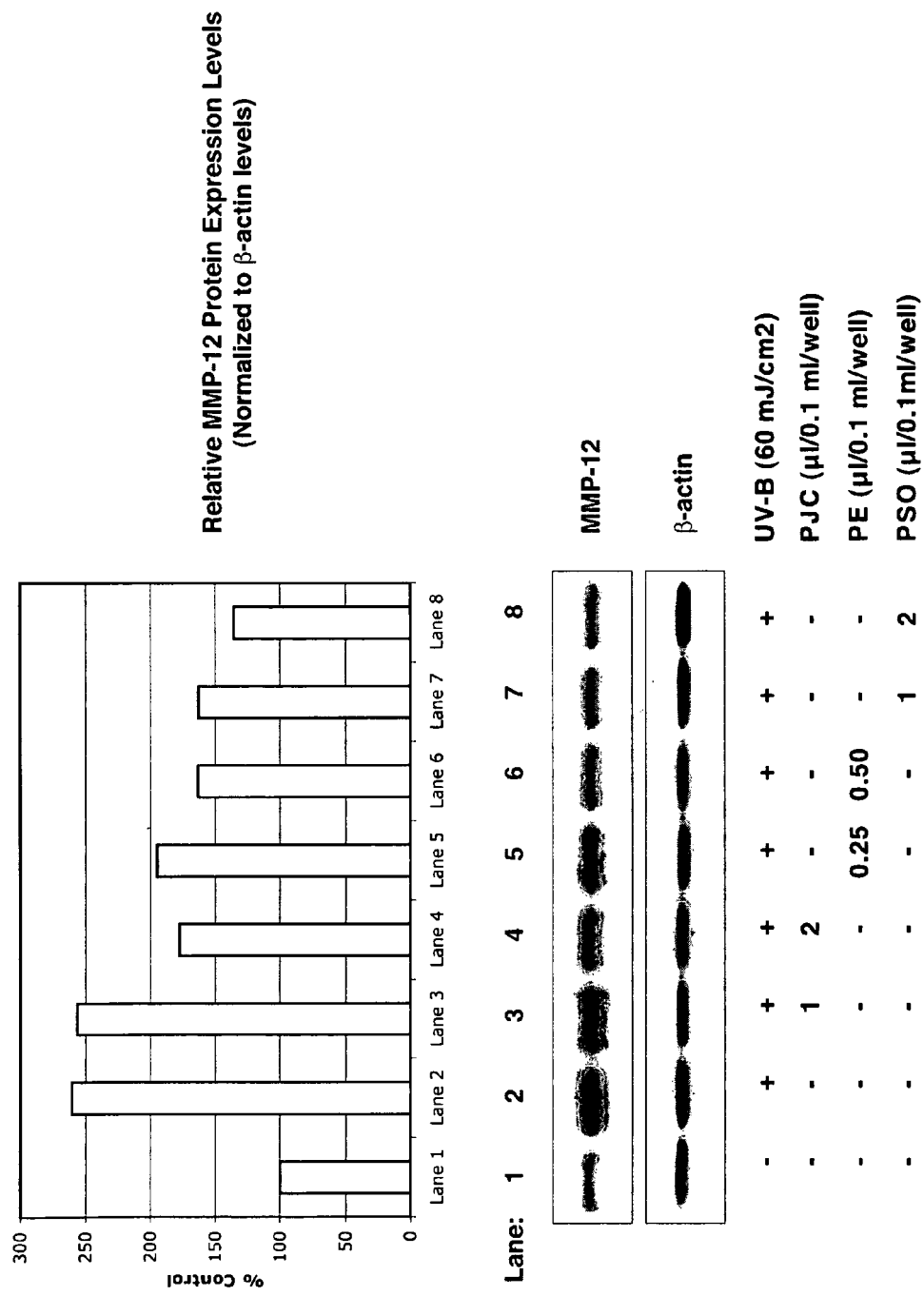
FIG. 9 is a digital composite image containing a bar graph of relative protein expression levels of MMP-12 (macrophage metalloelastase) and depicting the effects of PJC, PE, and PSO on UVB-mediated induction of matrix metalloproteinases (MMPs) in skin tissue samples.

FIGS. 8 and 9 illustrate the effects of pomegranate-derived compositions on UVB-mediated induction of MMP-11 and MPP-12 protein expression respectively in EpiDermFT™ tissue samples. All UVB-irradiated tissue samples treated with pomegranate-derived composition (except for 1 µl PJC-treated tissue samples) showed a similar level of inhibition of MMP-11 and MMP-12 protein expressions compared to untreated UVB-irradiated tissue samples. The differences in the inhibitory effect on MMP-11/MMP-12 protein expressions between 1 µl PJC- and 2 µl PJC-treated UVB-irradiated tissue samples may indicate dose dependent responses.

Figure 10:
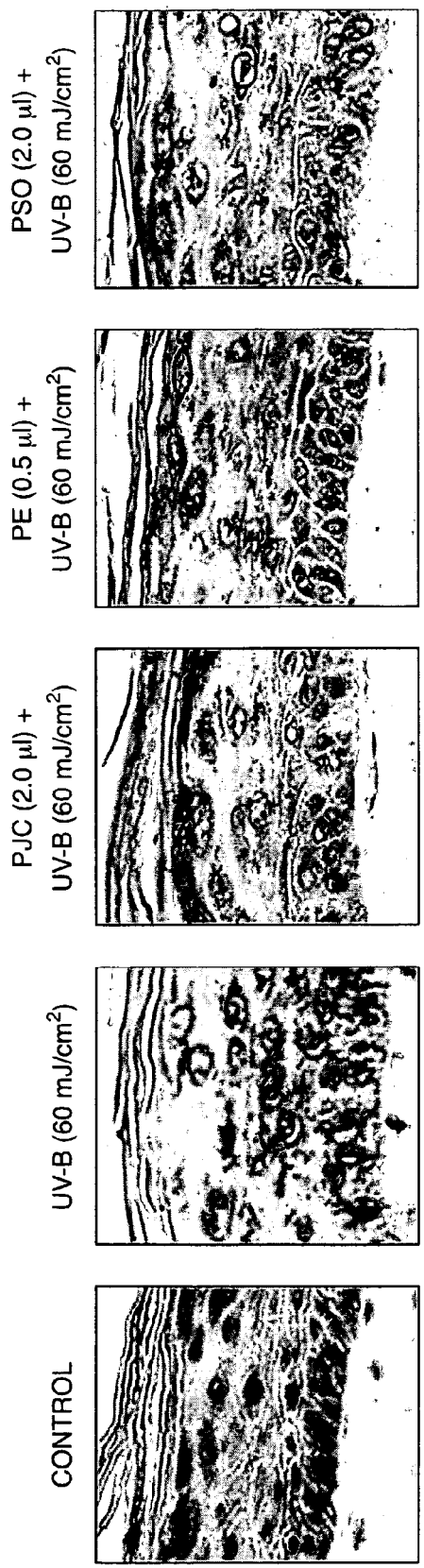
FIG. 10 depicts cross-sections of UVB irradiated skin tissue samples with immunohistochemical staining for MMP-2 and pre-treated either with PJC, PE, or PSO.

FIG. 10 illustrates immunohistochemical staining for MMP-2 in EpiDermTF™ tissue samples depicting the effects of PJC, PE, and PSO on UVB-mediated formation of MMP-2. The UVB-irradiated and untreated tissue sample shows denser immunohistochemical stain for MMP-2. UVB-irradiated tissue samples treated either with PJC (2.0 µl) or PSO (2.0 µl) indicate relatively less dense immunohistochemical stain for MMP-2 compared to PE (0.5 µl)-treated UVB-irradiated tissue sample, which collaborates with the result of western blot analysis of FIG. 4.

Figure 11:
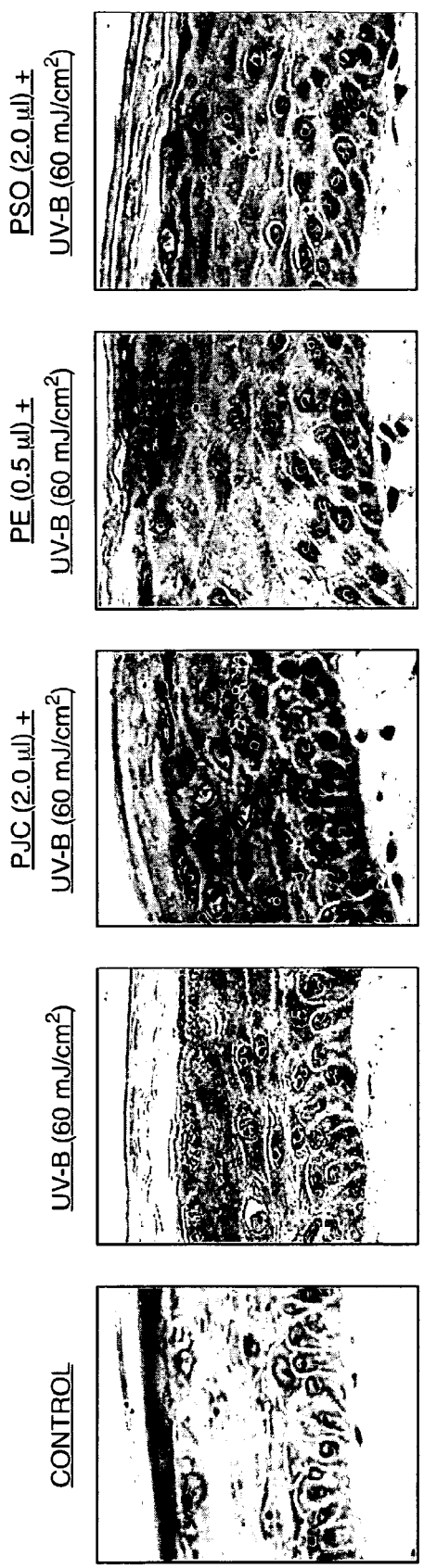
FIG. 11 depicts cross-sections of UVB irradiated skin tissue samples with immunohistochemical staining for MMP-12 and pre-treated either with PJC, PE, or PSO.

FIG. 11 illustrates immunohistochemical staining for MMP-12 in EpiDermTF™ tissue samples depicting the effects of PJC, PE, and PSO on UVB-mediated formation of MMP-12. The untreated UVB-irradiated tissue sample shows denser immunohistochemical stain for MMP-12. UVB-irradiated tissue samples treated either with PJC (2.0 µl), PE (0.5 µl) or PSO (2.0 µl) indicate relatively less dense immunohistochemical stain for MMP-12 compared to the untreated UVB-irradiated tissue sample.

Figure 12:
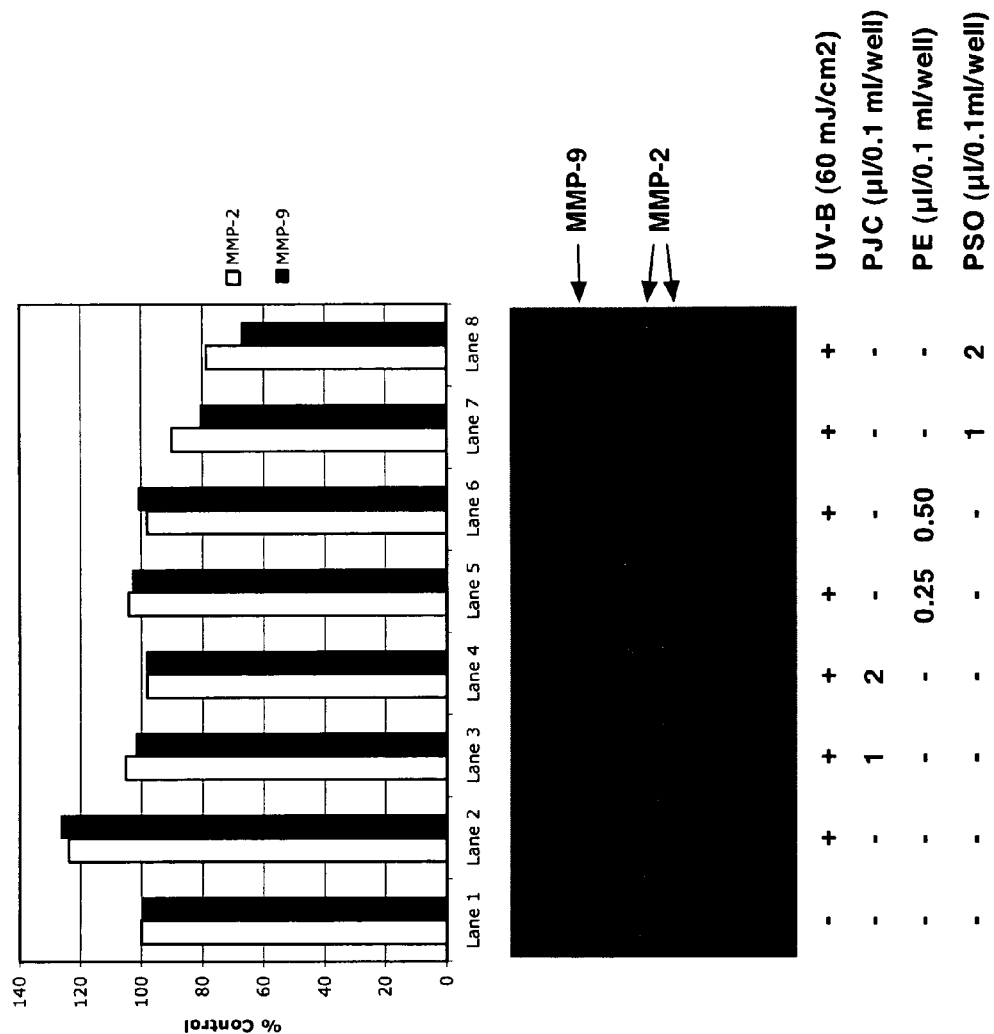
FIG. 12 is a digital composite image illustrating gelatin zymographic analysis of the effects of PJC, PE, and PSO on UVB-mediated induction of MMP-2 and MMP-9 activities in skin tissue samples.

FIG. 12 illustrates the effects of PJC, PE, and PSO on UVB-mediated induction in MMP-2 and MMP-9 activities in EpiDermFt™. The tissue samples (10 µg) were resolved by nonreducing 10% SDS-PAGE through gels containing 1 mg/mL gelatin. The gels were washed with 2.5% Triton X-100 to remove the SDS, and then were incubated overnight at 37° C. in 50 mmol/L Tris-HCl, pH 8.5, 5 mmol/L CaCl2, and 0.5 mmol/L ZnCl2. The zones of lysis were visualized after staining the gels with 0.5% Coomassie blue R-250. A densitometric analysis indicates inhibition of UVB-induced MMP-2 and MMP-9 activities of UVB-irradiated tissue sample treated with different pomegranate-derived composition compared to UVB-irradiated and untreated tissue sample. PSO-treated tissue samples showed strongest inhibitory effects on UVB induced MMP-2 and MMP-9 activities compared to PJC- and PE-treated tissue samples.

UVB-Mediated Increase in Tropoelastin Protein Expression

Acute and chronic UVB irradiation are known to increase tropoelastin mRNA and protein expression in the epidermis of human skin in vivo, which may contribute to increased elastin production in photodamaged skin and the accumulation of elastotic materials which its phenomenon is known as solar elastosis.

Figure 13:
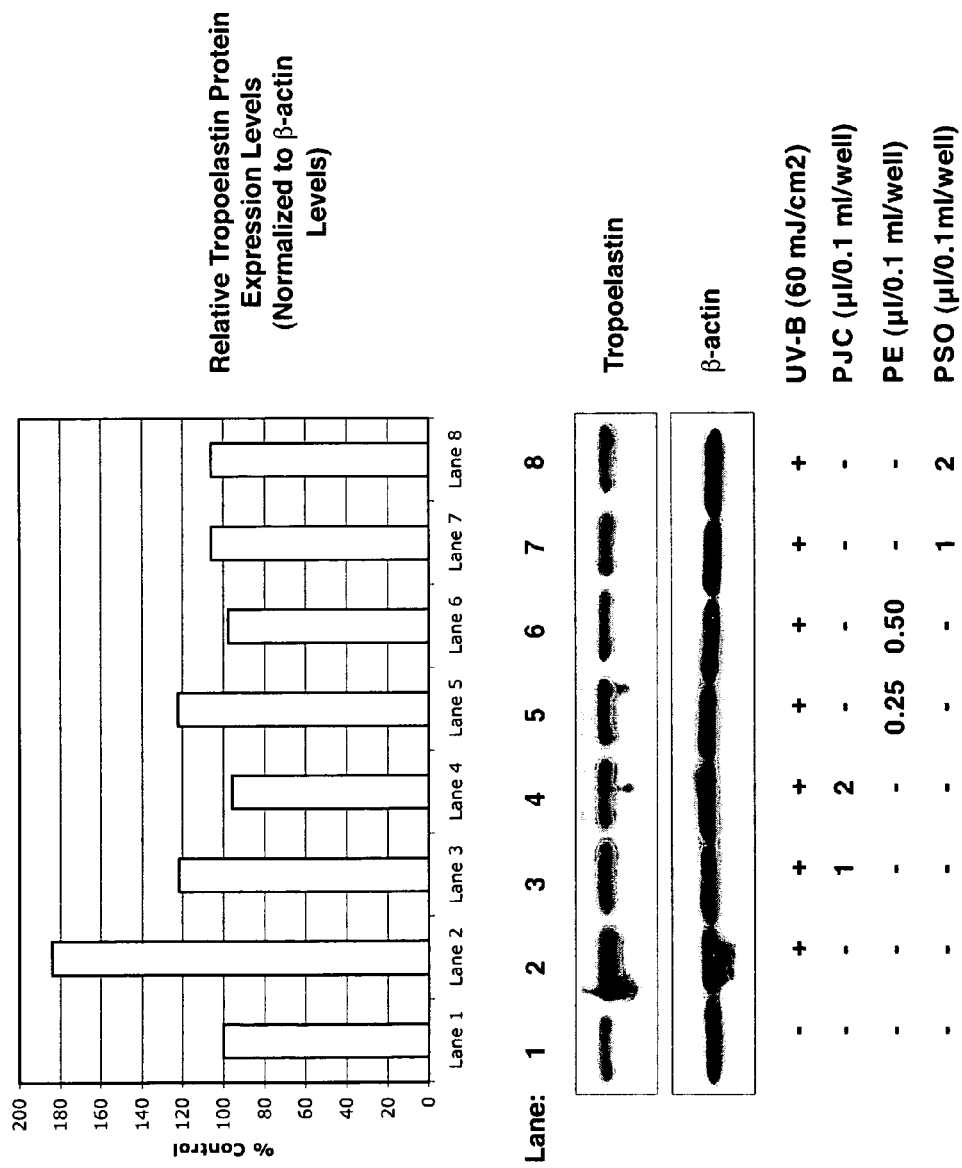
FIG. 13 is a digital composite image containing a bar graph of relative protein expression levels of tropoelastin and depicting the effects of PJC, PE, and PSO on UVB-mediated induction of tropoelastin in skin tissue samples.

FIG. 13 illustrates the effects of pomegranate-derived compositions on UVB-mediated induction of tropoelastin protein expression in EpiDermFT™ tissue samples. All UVB-irradiated tissue samples treated with different pomegranate-derived composition show a similar level of inhibition of tropoleastin protein expression compared to untreated UVB-irradiated tissue sample.

Figure 14:
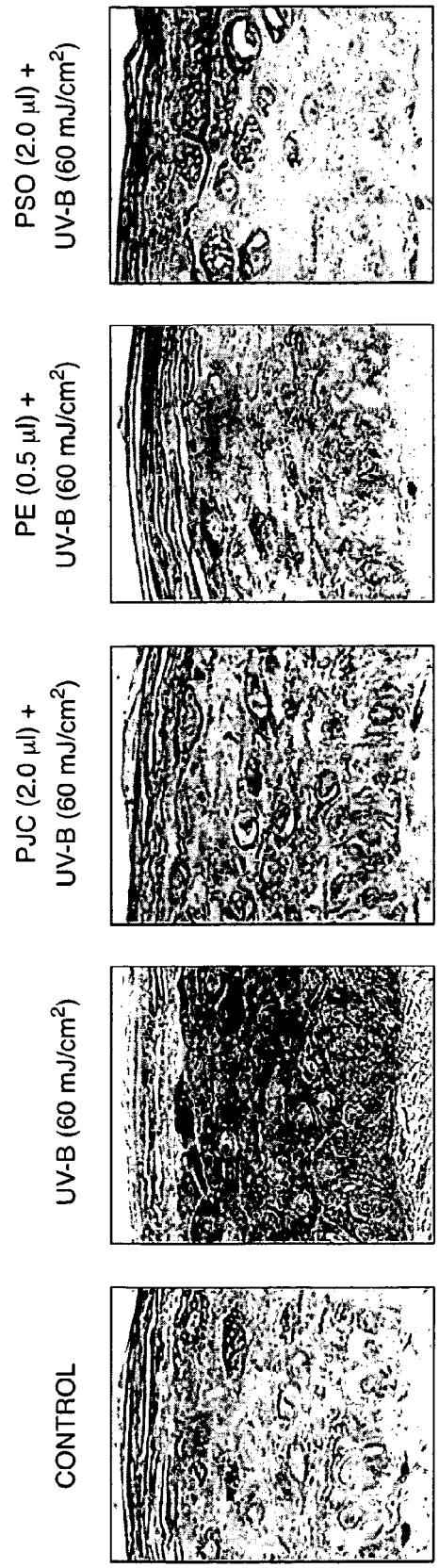
FIG. 14 depicts cross-sections of UVB irradiated skin tissue samples with immunohistochemical staining for tropoelastin and pre-treated either with PJC, PE, or PSO.

FIG. 14 illustrates immunohistochemical staining for MMP-12 in EpiDermTF™ tissue samples depicting the different modes of action on epidermis layers for pomegranate-derived compositions on UVB-mediated induction of tropoelastin protein expression. The untreated UVB-irradiated tissue sample shows denser immunohistochemical staining for tropoelastin in all layers of epidermis compared to the three pomegranate-derived composition-treated tissue samples. PJC- and PE-treated tissue samples show a similar less dense tropoelastin immunohistochemical stain distribution for all layers of epidermis. PSO-treated tissue sample indicates that UVB-mediated tropoelastin expression is confined mainly on the upper layers of epidermis including stratum corneum and that the lower layers of epidermis for PSO-treated tissue sample are comparable to the control tissue sample.

UVB-Mediated DNA Damage

DNA damage induced by UV radiation is the most common cause of skin cancer in humans. Cyclobutane pyrimidine dimers (CPDs) and 8-hydroxy-2'-deoxyguanosine (8-OHdG) are formed in epidermal DNA after UVB irradiation and are considered as important biomarkers of DNA damage.

Figure 15:
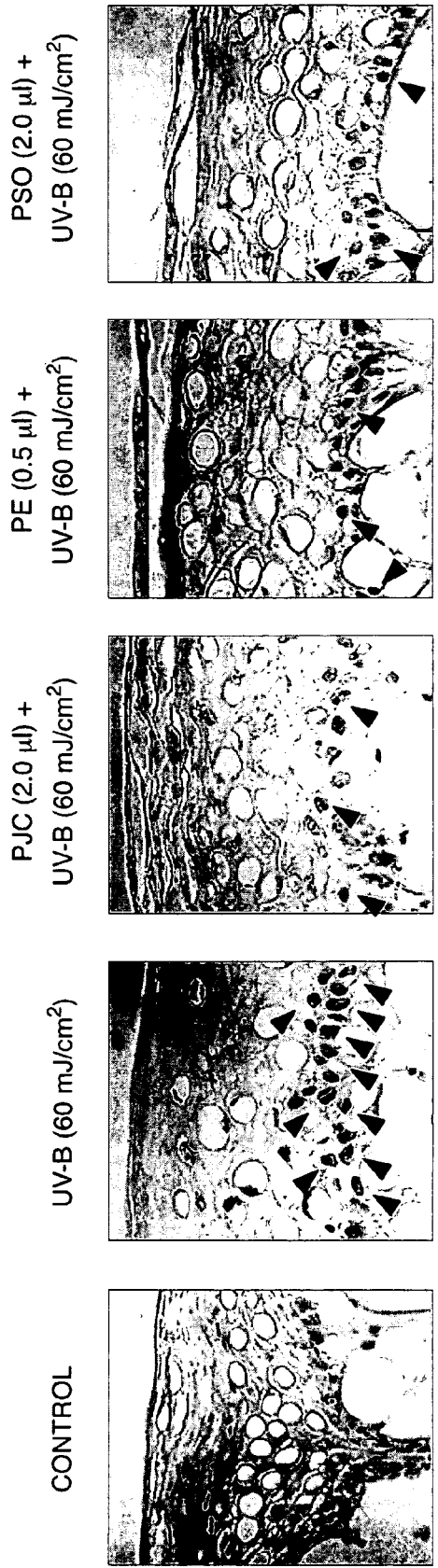
FIG. 15 depicts cross-sections of UVB irradiated skin tissue samples with immunohistochemical staining for cyclobutane pyrimidine dimers and pre-treated either with PJC, PE, or PSO. Arrows indicate positively stained cells.

FIG. 15 illustrates immunohistochemical staining for cyclobutane pyrimidine dimers in EpiDermTF™ tissue samples depicting the effects of PJC, PE, and PSO on UVB-mediated formation of CPDs. Arrows in FIG. 15 indicate positively stained cells. Untreated tissue sample exposed to UVB (60 mJ/cm$^2$) alone showed much higher number of cells positive for the presence of CPDs than UVB-irradiated tissue sample treated either with PJC, PE, or PSO. The cells positive for the presence of CPDs are found mostly at the stratum basale layer.

Figure 16:
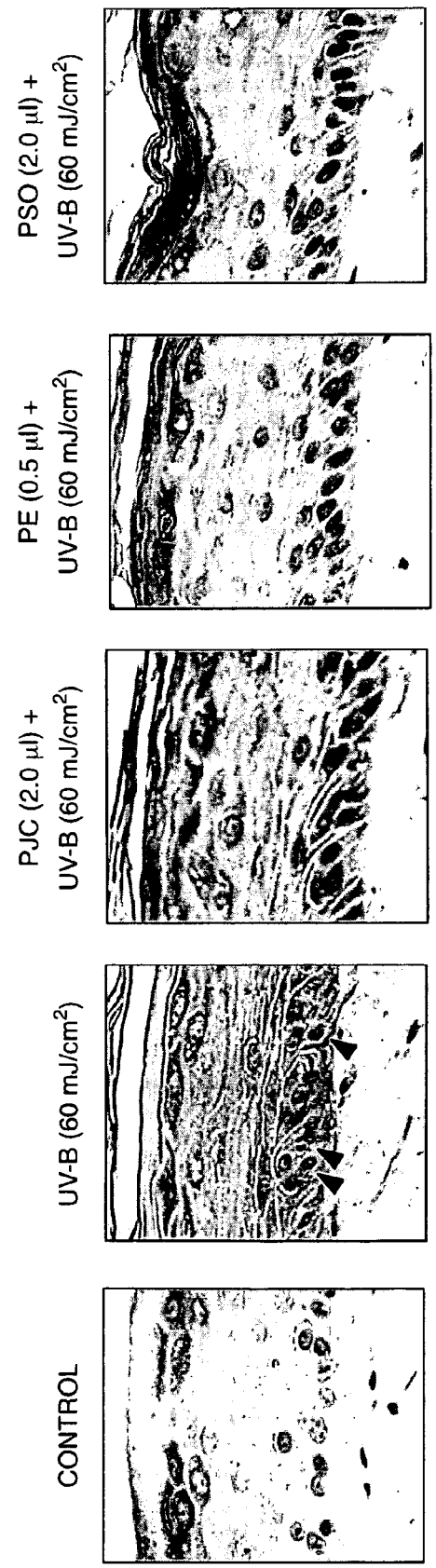
FIG. 16 depicts cross-sections of UVB irradiated skin tissue samples with immunohistochemical staining for 8-hydroxy-2'-deoxygranosine (8-OHdG) and pre-treated either with PJC, PE, or PSO. Arrows indicate positively stained cells.

FIG. 16 illustrates immunohistochemical staining for 8-hydroxy-2'-deoxyguanosine in EpiDermTF™ tissue samples depicting the effects of PJC, PE, and PSO on UVB-mediated formation of 8-OHdG. Arrows in FIG. 16. Indicate positively stained cell. The positively stained cells indicating the presence of 8-OHdG were detected only in untreated UVB-irradiated tissue sample.

Both results in FIGS. 15 and 16 indicate that the pomegranate-derived compositions inhibited UVB-induced formation of CPDs and 8-OHdG respectively, which suggest that administration of the pomegranate-derived compositions may be effective in preventing DNA damage leading to carcinogenesis and skin cancer.

Effects of PJC, PE, and PO on UVB-Mediated Protein Oxidation

Acute and chronic UV exposure is associated with protein oxidation in human skin and results in photoaging. Proteins are known to be important targets for oxidative modifications through multiple mechanisms, including the generation of reactive oxygen species upon UV exposure. Oxidatively modified proteins have been shown to increase as a function of age.

Figure 17:
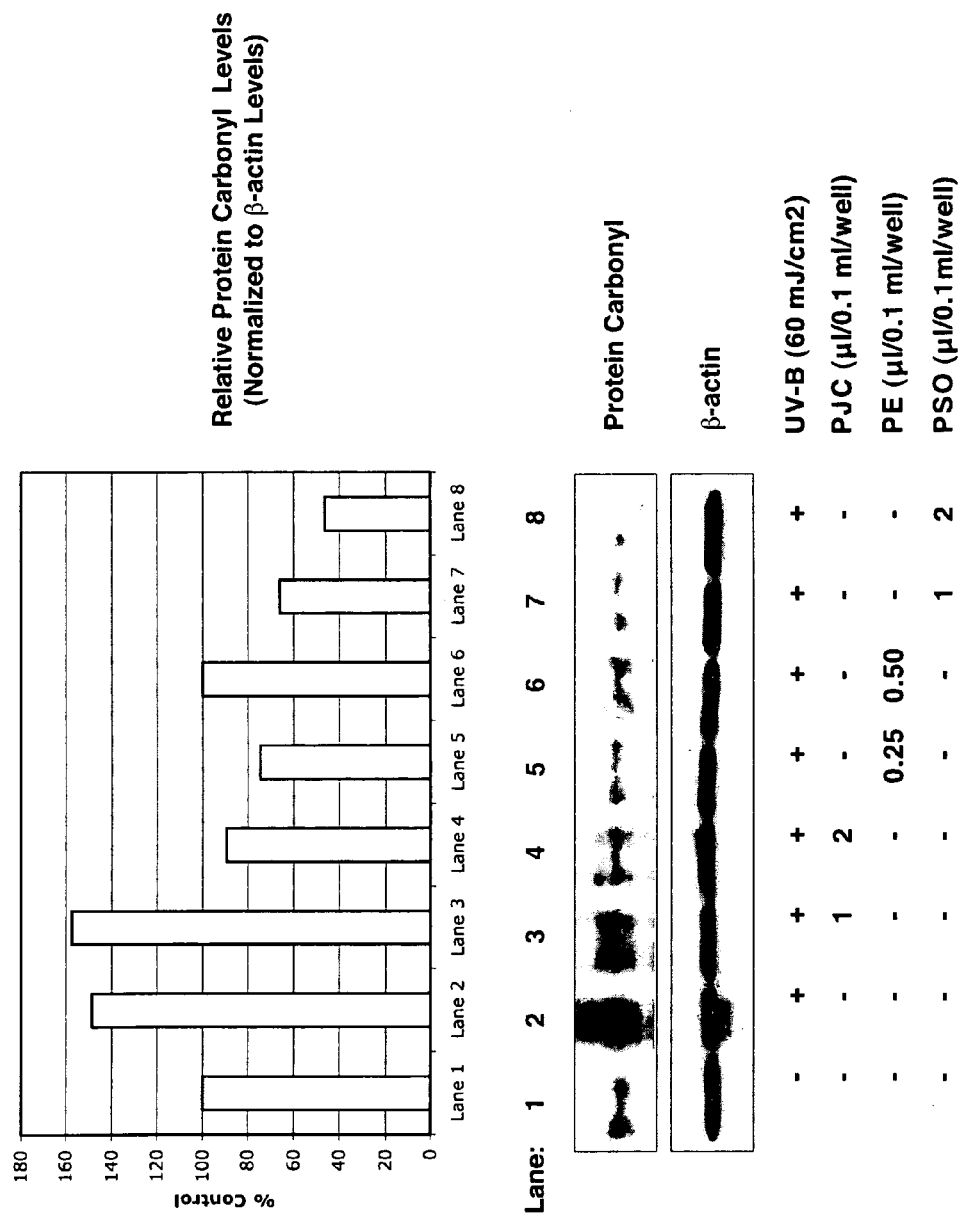
FIG. 17 is a digital composite image containing a bar graph of relative protein carbonyl levels and depicting the effects of PJC, PE, and PSO on UVB-mediated protein oxidation in skin tissue samples.

FIG. 17 illustrates the effects of pomegranate-derived compositions on UVB-mediated protein oxidation in EpiDermFT™. All UVB-irradiated tissue samples treated with different pomegranate-derived composition (except for 1 µl PJC-treated tissue sample) show a similar level of inhibition of protein carbonyl residues compared to untreated UVB-irradiated tissue sample. The differences in the inhibitory effects on protein carbonyl between 1 µl PJC- and 2 µl PJC-treated UVB-irradiated tissue samples may indicate dose dependent responses.

The results indicate that the antioxidant activities of pomegranate-derived compositions inhibits UVB-induced protein oxidation which suggest that the compositions may be effective in ameliorating disorders related to oxidatively modified proteins and aging.

Effects of PJC, PE and PO on UVB-Mediated Induction of PCNA

PCNA is an auxiliary protein of DNA polymerase-δ and its high levels of expression correlate cell proliferation, suggesting that PCNA is an excellent marker of cellular proliferation, which also serves as an effective prognostic indicator of initiated cancer cells.

Figure 18:
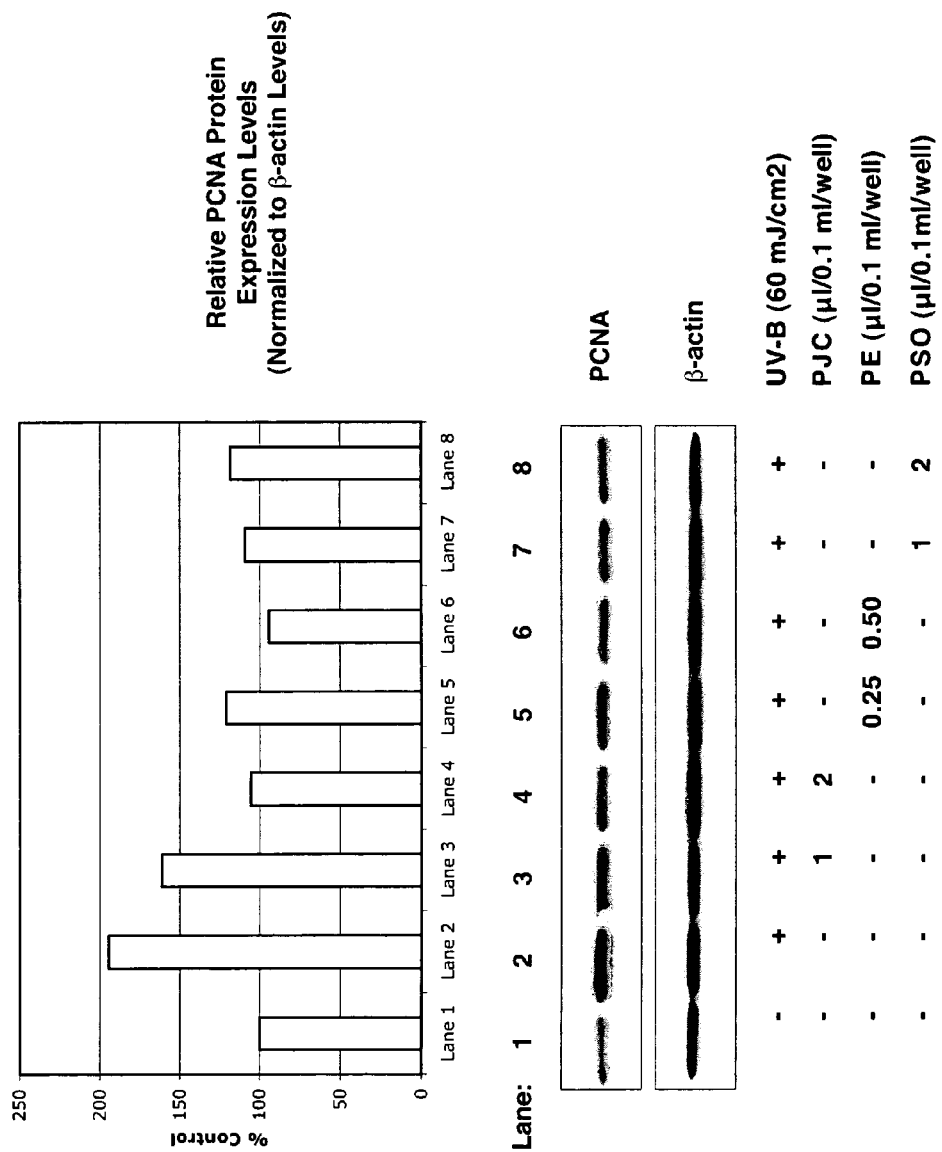
FIG. 18 is a digital composite image containing a bar graph of relative protein expression levels of proliferating cell nuclear antigen (PCNA) and depicting the effects of PJC, PE, and PSO on UVB-mediated induction of PCNA in skin tissue samples.

FIG. 18 illustrates the effects of pomegranate-derived compositions on UVB-mediated increase in PCNA protein expression in EpiDermFT™. All UVB-irradiated tissue samples treated with different pomegranate-derived composition show a similar level of inhibition of PNCA protein expression levels compared to untreated UVB-irradiated tissue sample. The differences in the inhibitory effects on protein carbonyl between 1 µl PJC- and 2 µl PJC-treated UVB-irradiated tissue samples may indicate dose dependent responses.

Figure 19:
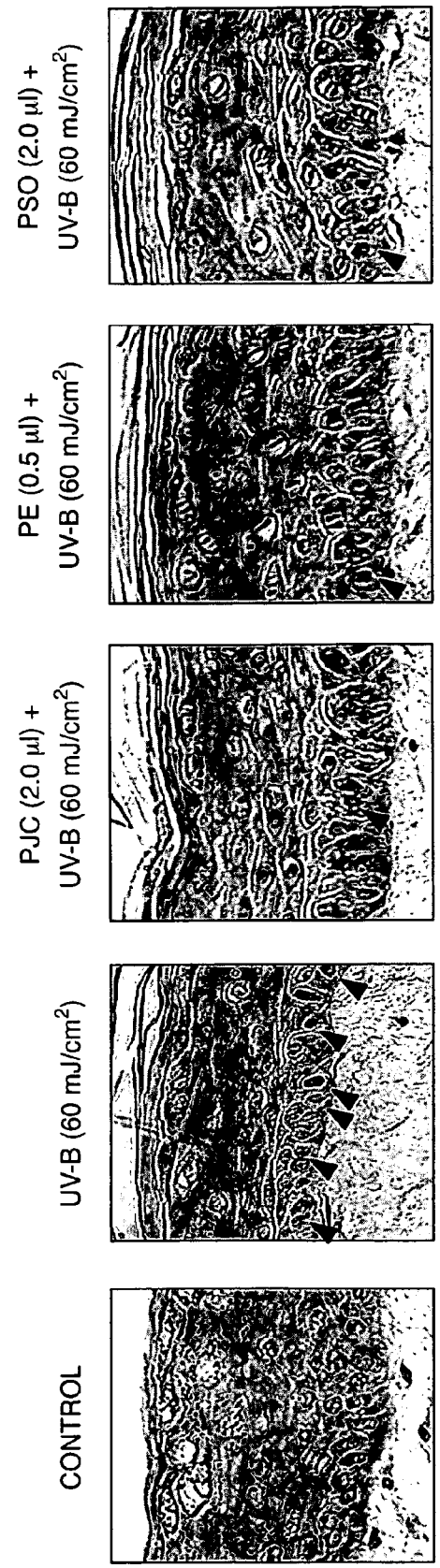
FIG. 19 depicts cross-sections of UVB irradiated skin tissue samples with immunohistochemical staining for PCNA and pre-treated either with PJC, PE, or PSO. Arrows indicate positively stained cells.

FIG. 19 illustrates immunohistochemical staining for 8-hydroxy-2'-deoxyguanosine in EpiDermTF™ tissue samples depicting the effects of PJC, PE, and PSO on UVB-mediated protein expression of PCNA. Arrows in FIG. 19. Indicate positively stained cell. The untreated UVB-irradiated tissue sample showed higher number of cells indicating the presence of PCNA than the UVB-irradiated tissue sample treated either with PJC, PE, or PSO.

The results suggest that all three pomegranate-derived compositions inhibit UVB-induced protein expression of PCNA, which suggest that pomegranate-derived compositions may be useful in inhibiting cell proliferation and initiation of cancer cells.

Effects of PJC, PE and PO on UVB-Mediated Activation of c-Jun and c-Fos

UVB irradiation results in activation of proto-oncogenes, such as c-Fos and c-Jun, that leads to cell proliferation and tumor formation. Proto-oncogene c-fos and c-jun are known to code for the transcription factor AP-1 by forming a heterodimeric complex between Fos and Jun proteins and the formation of AP1 by these two oncoproteins is necessary for DNA binding, gene activation, cell cycle progression, cell proliferation and differentiation.

Figure 20:
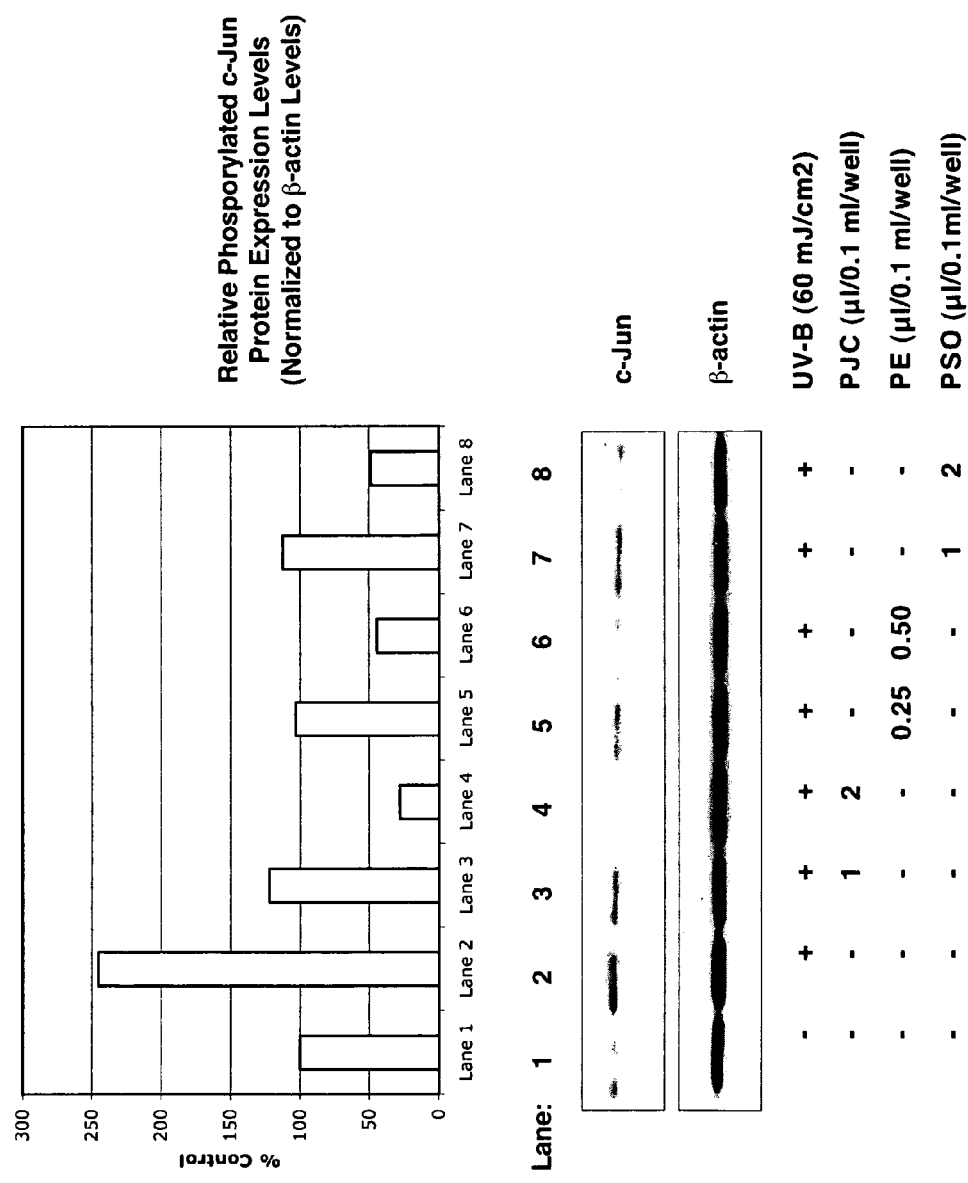
FIG. 20 is a digital composite image containing a bar graph of relative phosphorylated c-Jun protein expression levels and depicting the effects of PJC, PE, and PSO on UVB-mediated induction of c-Jun phosphorylation in EpiDermFT™ tissue samples.

FIG. 20 illustrates the effects of PJC, PE, and PSO on UVB-mediated increase in phosphorylated c-Jun protein expression levels in EpiDermFT™. All UVB-irradiated tissue samples treated with different pomegranate-derived composition show inhibition of phosphorylated c-Jun protein expression levels compared to untreated UVB-irradiated tissue sample. The pomegranate-derived compositions with strongest inhibitory effects are shown in lanes 4, 6, and 8 of FIG. 20. The differences in the inhibitory effects between different concentrations of pomegranate-derived compositions may indicate dose dependent responses.

Figure 21:
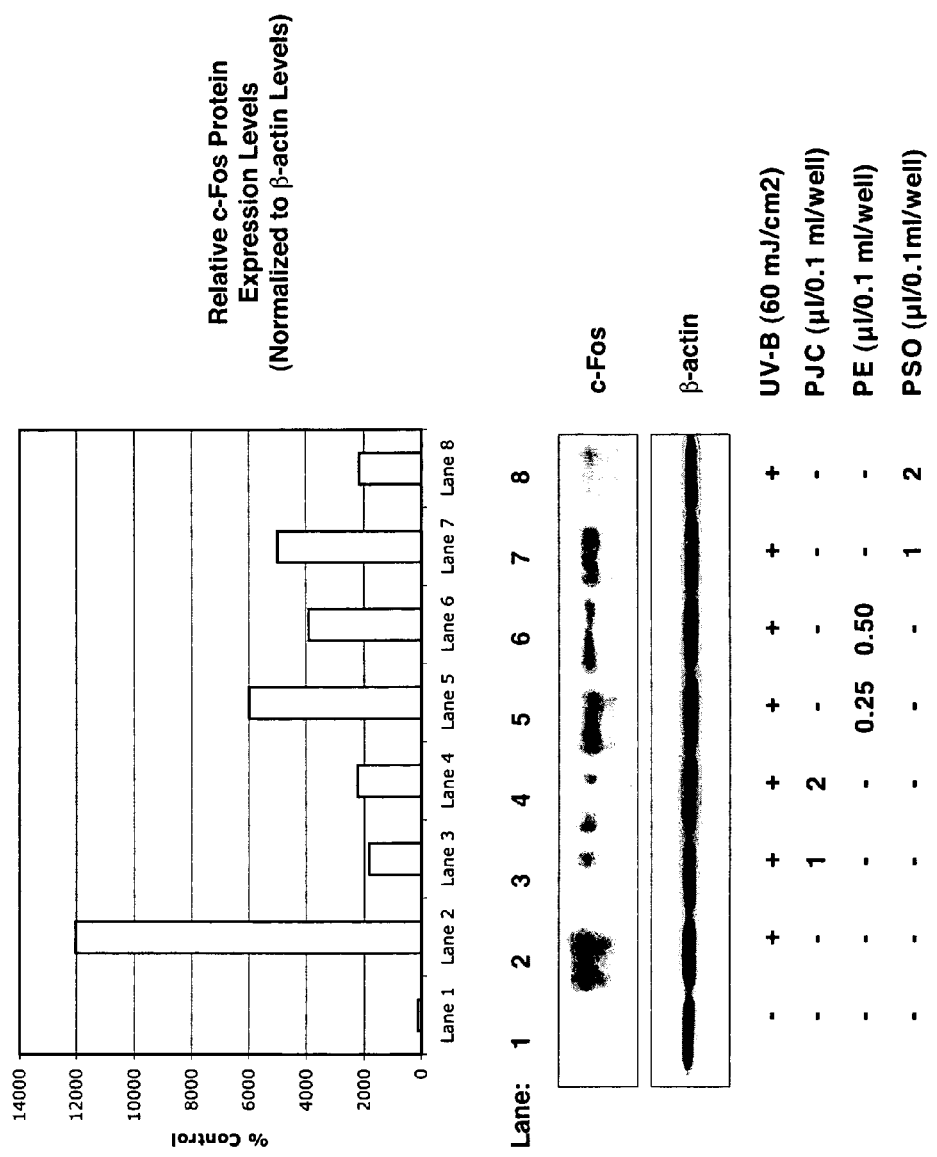
FIG. 21 is a digital composite image containing a bar graph of relative protein expression levels of c-Fos and depicting the effects of PJC, PE, and PSO on UVB-mediated induction of c-Fos in skin tissue samples.

FIG. 21 illustrates the effects of PJC, PE, and PSO on UVB-mediated increase in c-Fos protein expression levels in EpiDermFT™. All UVB-irradiated tissue samples treated with different pomegranate-derived composition show inhibition of c-Fos protein expression levels compared to untreated UVB-irradiated tissue sample.

The results suggest that each of three pomegranate-derived composition may be used as a chemopreventive agent against UV-induced skin carcinogenesis.

EXAMPLE 6

Effects of PE on UVB-Induced Aging and Damage in HaCaT Cells

The effects of PE prepared in accordance of Example 2 were assessed on UVB-irradiated cells. For stimulation of skin cells under UVB irridation, immortalized human keratinocytes HaCaT was chosen for this study. HaCaT keratinocytes are derived from adult human skin and although spontaneously immortalized in vivo, remain highly related to their normal counterparts. HaCaT cells can proliferate in serum-free medium (SFM), in contrast to normal human keratinocytes whose growth in vitro requires a feeder layer and/or the supplementation with hormones and growth factors.

Materials and Methods

The immortalized human keratinocytes, HaCaT, were cultured in Dulbecco's modified eagle's media (DMEM) containing 4.5 g/l glucose and L-glutamine supplemented with 10% fetal bovine serum (ATCC, Manassas, Va.), 100 µg/ml penicillin and 100 unit/ml streptomycin. The cells were maintained under standard cell culture conditions at 37° C. and 5% $CO_2$ in a humid environment.

For treatment, HaCaT cells were maintained in DMEM culture media (Cambrex Biosciences, Walkersville, Md.) up to a confluence of 50-60% and then pretreated with indicated concentrations of pomegranate extract (PE) from Example 2 in dimethyl sulfoxide (DMSO) (final concentration of DMSO used was 0.1% (v/v) for each treatment and control) for 24 hours in DMEM medium after which the media was removed and cells were washed with phosphate buffer saline (PBS). Fresh PBS was added and cells were irradiated with UVB using a custom designed Research Irradiation Unit system as described in Example 5. Using this system, the cells were exposed to accurate dosimetery of UVB radiation. Cells were exposed to UVB 15 mJ/cm$^2$ or 30 mJ/cm$^2$, after which PBS was removed and fresh media added. Cells were harvested one hour after UVB irridation for MAPKs, and phosho-c-jun and c-fos expression, six hours for MMPs expression, LPO and GSH contents. For trolox equivalent antioxidant capacity (TEAC), cells were harvested 24 hr after PE treatment without UVB exposure.

Cell Growth/Cell Viability Assay: viability of cells in culture was measured by quantification of mitochondrial dehydrogenase activity by 3-[4,5-dimethylthiozol-2-yl]-2,5-diphenyltetrazolium bromide (MTT) assay. Briefly HaCaT cells were plated at 2×10$^4$ cells/well in 200 µl of DMEM medium in a 96-well microtiter plate and cultured overnight followed by treatment with PE, with or without UVB treatment at a dose of 15 and 30 mJ/cm$^2$ as detailed above. After culturing for another 24 hr, cells were incubated with 100 µl of fresh media containing 0.1 mg/ml MTT for 2 hr at 37° C. The MTT solution was discarded from the wells by aspiration. Formazan crystals formed were dissolved in 100 µl of DMSO, and the absorbance was measured at 570 nm using a microplate reader (Thermolab Systems, Finland). The effect of PE on growth inhibition was assessed as percentage cell viability where vehicle-treated cells were taken as 100% viable.

Trolox Equivalent Antioxidant Capacity (TEAC): the total antioxidant activity of PE was measured by TEAC assay, which measures the combined antioxidant activity of all the constituents using antioxidant assay kit (Cayman Chemicals Company, Ann Arbor, Mich.), following the manufacture's protocol. The assay relies on the ability of antioxidants to inhibit oxidation of ABTS (2'2-Azino-di-[3-ethylbenzthiazoline sulphonate) to ABTS* by metmyoglobin. The ABTS present is measured by reading its absorbance at 750 nm. Trolox (6-hydroxy-2,5,7,8-tetramethylchroman-2-carboxylic acid), a water soluble analogue of vitamin E, was used as an antioxidant standard. Briefly cells were collected by scraping in ice cold buffer (5 mM potassium phosphate pH 7.4 containing 0.9% sodium chloride and 1% glucose), lysed by sonication and centrifuged at 13,000×g for 15 min at 4° C. The supernatant was removed and stored on ice for the assay. 10 µl of standard or sample was added to each well of 96 well plate followed by 10 µl of metmyoglobin and 150 µl of ABTS and the reaction was initiated by addition of 40 µl of 441 µM hydrogen peroxide. The plate was incubated on a shaker at room temperature for 5 min and absorbance read at 750 nm. The antioxidant capacity of samples was calculated from the standard calibration curve of trolox in terms of trolox equivalent per mg protein. Protein estimation was done by BCA method.

Reduced Glutathione Content: nonprotein sulfhydryls, mainly GSH, were measured spectrophotometrically after reacting with DTNB (5,5'-dithiobis-2-nitrobenzoic acid from Sigma Chemicals, St. Louis, Mo.). The method is based on the ability of the sulphydryl group to reduce DTNB and form a yellow-colored anionic product, OD of which is measured at 412 nm. Briefly HaCaT cells were collected in cold 50 mM MES buffer pH 6.0 containing 1 mM EDTA, sonicated on ice and centrifuged at 13,000×g for 15 min at 4° C. The supernatant was deproteinized by equal amount of 20% metaphosphoric acid, centrifuged and clear supernatant was used for the assay. Concentrations of GSH were determined from a standard plot as GSH per mg protein. Protein estimation was done by BCA method (bicinchoninic acid protein assay kit from Pierce Biotechnology, Rockford, Ill.).

Lipid Peroxidation (LPO) Assay: LPO was assayed as thiobarbituric acid reacting substances (TBARS) in terms of malondialdehyde (MDA) equivalents by OXI-TEK (TBARS) assay kit (Alexis Biochemicals, Baffalo, N.Y.) following manufacturer's protocol. Briefly, cells were collected in PBS and homogenized by sonication on ice and the whole cell homogenate was used for estimation of LPO. MDA standard or sample homogenate 100 µl was added to 100 µl of SDS solution, to it 2.5 ml of thiobarbituric acid-buffer reagent was added and incubated at 95° C. for 60 min, cooled to room temperature on ice and centrifuged at 3000×g for 15 min and the absorbance of supernatant read at 532 nm. The extent of LPO was calculated from the standard calibration curve of MDA as MDA per mg protein. Protein estimation was done by BCA method.

Whole Cell Lysate Preparation: HaCaT cell lysate for western blot analysis was prepared by keeping the cells in 0.3 ml of lysis buffer (10 mM Tris-HCl, pH 7.4, 150 mM NaCl, 1% Triton X-100, 1 mM EDTA, and 1 mM EGTA) containing 0.2 mM sodium vanadate, 2 mM PMSF, 0.5% NP-40, and 0.2 U/ml aprotinin with freshly added protease inhibitor cocktail set III (Calbiochem, La Jolla, Calif.) at 4° C. for 15 min. The cells were scraped and collected in a microfuge tube and then passed through a 22½-G needle to break up the cell aggregates. The lysates were centrifuged at 13,000×g for 25 min at 4° C. to remove cell debris. Supernatant was collected, and protein estimation was done by BCA method.

SDS-Polyacrylamide Gel Electrophoresis and Western Blot Analysis: for western blot analysis, equal amount (30-40 µg) of protein was resolved electrophoretically over 12% tris glycine gel, and transferred to a nitrocellulose membrane. The blot containing the transferred protein was blocked in blocking buffer (5% nonfat dry milk in 20 mM Tris-buffered saline, pH 7.6 containing 1% Tween 20-TBST) for 1 hr at room temperature followed by incubation with appropriate primary antibody in blocking buffer for 2 hr to overnight at 4° C. This was followed by incubation with specific anti-mouse or anti-rabbit secondary antibody horseradish peroxidase for 2 hr at room temperature and then washed 3 times, 15 min each in TBST and detected by enhanced chemiluminescence and autoradiography using Blue Lite Autorad film obtained from ISC Bioexpress (Kaysville, Utah). Phospho-ERK1/2 (Thr202/Tyr204), phospho-JNK1/2 (Thr183/Tyr185) and phospho-p38 (Thr180/Tyr182) antibodies were obtained from Cell Signalling Technology (Beverly, Mass.); phospho-c-jun (Ser73) from Upstate Cell Signaling Solutions (Charlottesville, Va.); MMP-1, MMP-2 and MMP-9 antibodies from Lab Vision Corporation (Fremount, Calif.); MMP-7 and TIMP-1 antibodies from Santa Cruz Biotechnology, Inc. (Santa Cruz, Calif.); anti-mouse or anti-rabbit secondary antibody horseradish peroxidase conjugate and ECL western blotting detection reagent was obtained from Amersham Life Science (Arlington Height, Ill.).

Statistical analysis: The results are expressed as mean plus minus standard deviation. Statistical analysis of data was performed using Student's t-test and $p<0.001$ was considered statistically significant.

UVB-Mediated Cytotoxicity

Figure 22:
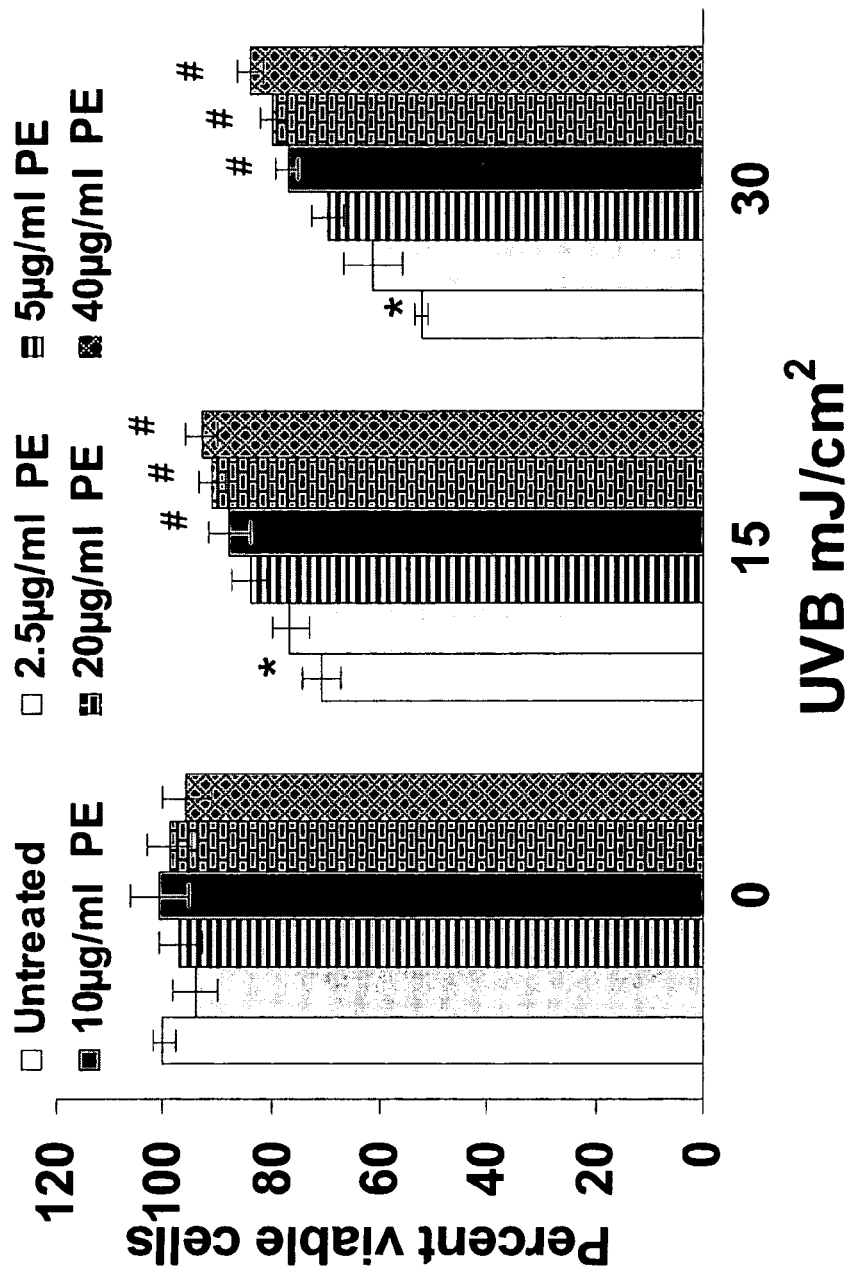
FIG. 22 is a bar graph illustrating PE treatment protecting cells from UVB-mediated decrease in cell viability. HaCaT cells were treated with different doses of PE (2.5-40 μg/ml) for 24 hours after which the media was removed and cells were washed once with PBS and then fresh PBS was added and cells were exposed to UVB (15-30 mJ/cm$^2$) radiation. After UVB exposure PBS was removed and fresh media was added. At 24 hours after UVB irradiation, percent cell viability was assessed by the MTT assay. Data shown are mean±SD of three separate experiments in which each treatment was repeated in 10 wells. *$p<0.001$ versus control, #$p<0.001$ versus respective UVB.

The effect of PE (2.5-40 µg/ml) against UVB-mediated cytotoxicity was measured by cell viability assay. Irradiation of HaCaT cells with UVB resulted in a significant decrease in cell viability. FIG. 22 shows UVB mediated cytotoxicity was significantly prevented by pretreatment of cells with PE (10-40 µg/ml) in a dose-dependent manner. PE treatment to the control cells showed no cytotoxic effects at the dose studied.

PE Exerts Strong Antioxidant Effect

Figure 23:
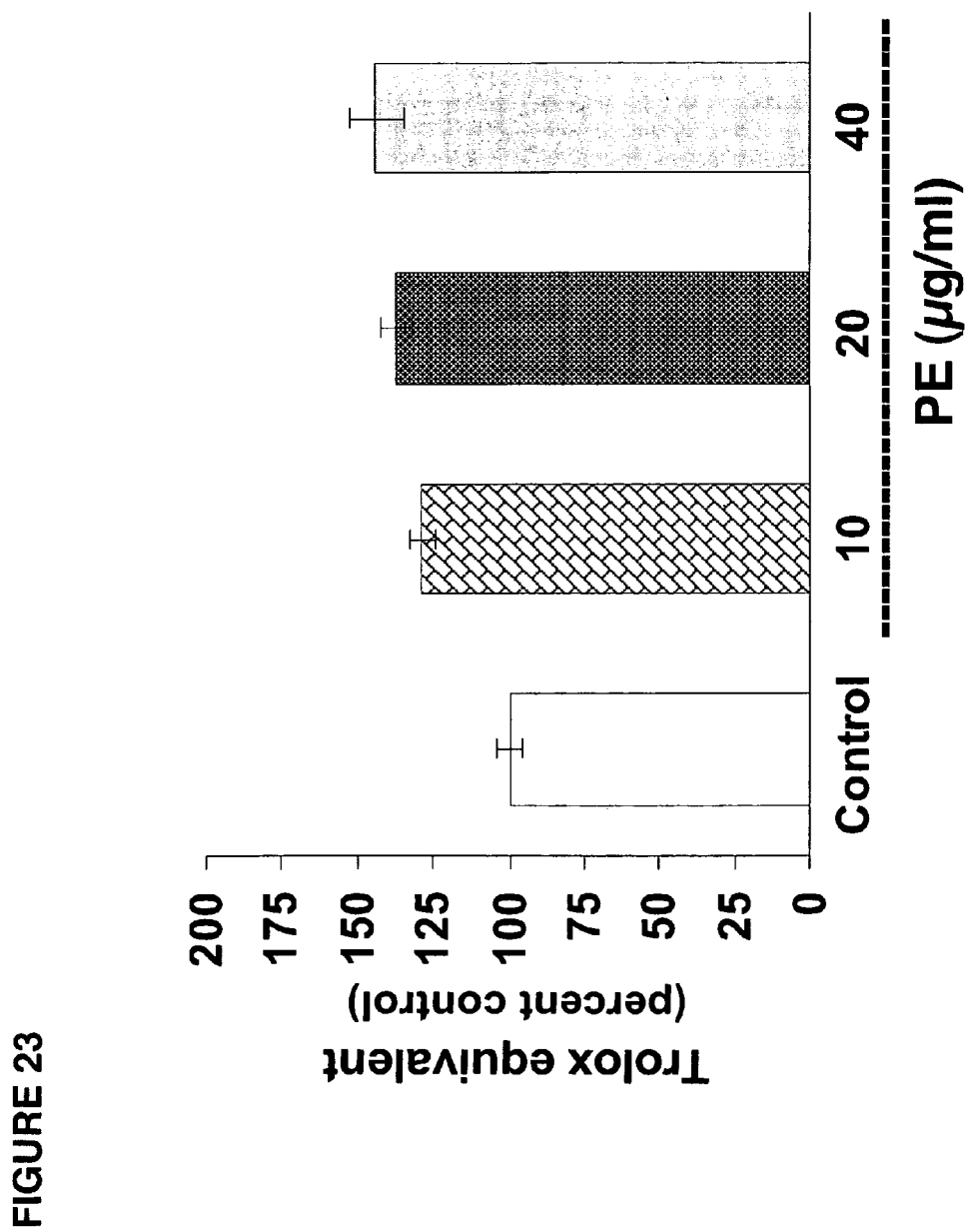
FIG. 23 is a bar graph illustrating antioxidant activity of PE. HaCaT cells were treated with different doses of doses of PE (10-40 μg/ml) for 24 hours after which the media was removed, cells were harvested and cell lysates were prepared for antioxidant activity. The cell lysate was added to the ABTS radical cation decolorization assay. Antioxidant capacity was assayed by using the antioxidant assay kit following the manufacture's protocol. Data shown are mean±SD of three separate experiments.

In order to determine whether the observed protective effect of PE against UVB-mediated decrease in cell viability is due to its antioxidant activity, TEAC assay was performed. TEAC provides a tool for monitoring total antioxidant activity. HaCaT cells were pretreated with PE (10-40 µg/ml) for 24 hr and cell lysates were prepared as described above. The doses of PE (10-40 µg/ml) selected were based on the data shown in FIG. 22, as these doses provide significant protection against UVB-mediated cytotoxicity. FIG. 23 shows that PE exerted strong antioxidant activity, as TEAC increased in cells treated with PE in a dose-dependent manner when compared to untreated cells.

The result from cell viability assay and TEAC assay show that the percentage of viable cells was markedly reduced after UVB-irradiation as compared to control cells. Cellular antioxidant mechanisms may be overwhelmed by excessive free radical generation altering the redox status of cell and affects cell viability. PE protects the cells from UVB-mediated cell death (FIG. 22) by their strong antioxidant activity (FIG. 23), and therefore plays a significant role in ameliorating or preventing photo-biological damage.

PE Inhibits UVB-Mediated Decrease in GSH Levels

Figure 24A:
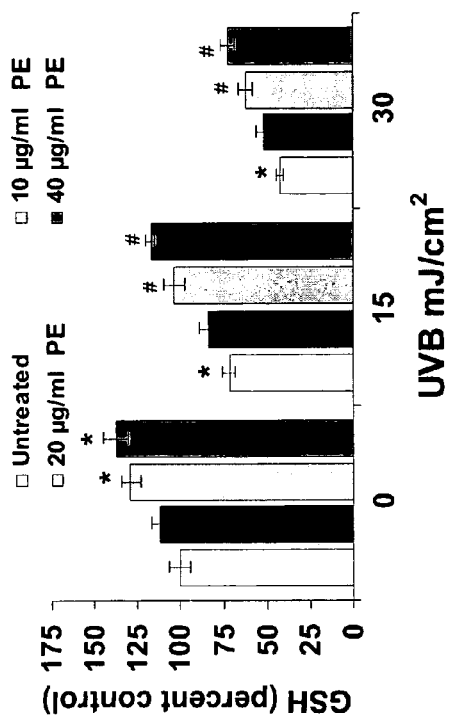
FIGS. 24A and 24B are bar graphs illustrating inhibitory effects of PE on UVB-mediated decrease in GSH levels and increase in LPO. HaCaT cells were treated with different doses of PE (10-40 μg/ml) for 24 hours after which the media was removed and cells were washed once with PBS and then fresh PBS was added and cells were exposed to UVB (15-30 mJ/cm$^2$). After UVB exposure PBS was removed and fresh media was added. Six hours post UVB, the cells were harvested and cell lysates were prepared for (24A) GSH and (24B) LPO. Data shown are mean±SD of three separate experiments. *$p<0.001$ versus control, #$p<0.001$ versus respective UVB.

Among the cutaneous antioxidants, the tripeptide glutathione (γ-glutamyl-cysteinyl-glycine) plays an important role in protecting skin cells from oxidative damage by directly scavenging ROS or acting as a coenzyme in GSH peroxidase or GSH-S-transferase catalyzed reactions. UVB-induced damage is mediated by generation of ROS resulting in oxidative stress that in turn results in depletion of endogenous antioxidants. FIG. 24A shows that treatment of cell with PE resulted in a significant increase in intracellular GSH levels. UVB (15-30 mJ/cm$^2$) irradiation resulted in a dose-dependent decrease in intracellular GSH. Pretreatment of cells with PE (10-40 µg/ml) prior to UVB exposure caused an increase in UVB-mediated decrease in GSH contents.

Gultathione is an important intracellular nonprotein sulphydryl peptide with multiple functions ranging from antioxidant defense to modulation of cell proliferation. GSH plays a central role in the maintenance of cellular redox homeostasis, regulating signaling pathways modulated by oxidative stress and protects skin cell against oxidative injury. UVB-mediated loss of cell viability is associated with a marked decrease in GSH content, indicating an impairment of the antioxidant pool, causing an increase in ROS, and may predispose the cell to a lower defense against condition of oxidative stress. GSH depletion was significantly and dose-dependently inhibited by pretreatment of cells with PE (FIG. 24A). PE protects cells from UVB-induced oxidative stress by increasing their antioxidative status.

PE Inhibits UVB-Mediated Increase in LPO

Figure 24B:
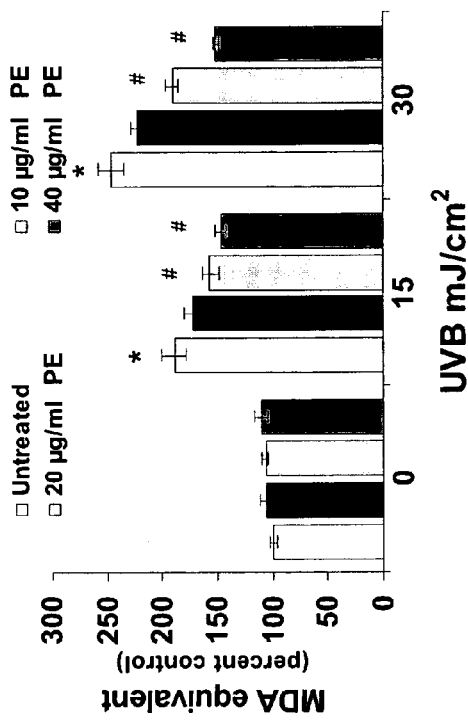

The effect of PE on UVB-mediated increase in LPO, which is a typical marker of oxidative stress, in HaCaT cells was evaluated. LPO in biological membranes is a free radical-mediated event and is regulated by the availability of substrates in the form of polyunsaturated fatty acids and pro-oxidants that promote peroxidation. LPO is highly detrimental to cell membrane structure and function, and its elevated level has been linked to damaging effects such as loss of fluidity, inactivation of membrane enzymes, increased cell membrane permeability and ultimately ruptured cell membranes leading to release of cell organelles. As shown in FIG. 24B, UVB irradiation of HaCaT cells resulted in a significant induction of LPO (measured in terms of malondialdehyde equivalent) by 89% and 146% at UVB doses of 15 and 30 mJ/cm² respectively, when compared to untreated cells. Pretreatment of cells with PE (10-40 µg/ml) was found to significantly inhibit UVB-mediated increase in LPO (FIG. 24B). Thus, inhibition of LPO by PE would result in the reduction of risk factors associated with UVB radiation.

Oxidative damage to lipid and protein, an immediate consequence of UV radiation to skin, occurs most readily in the superficial layers. Sustained oxidative insult as a result of UVB exposure causes LPO which leads to accumulation of MDA, a stable end product of LPO, indirectly suggesting the generation of reactive oxygen species (ROS). Increased LPO due to UVB irradiation may evoke immune and inflammatory responses and activate gene expression resulting from membrane-dependent oxidative damage. PE significantly reduced peroxide accumulation, suggesting that PE could scavenge ROS and inhibit the reaction of LPO (FIG. 24B).

PE Inhibits UVB-Mediated Increase in MMP Protein Expression

Figure 25:
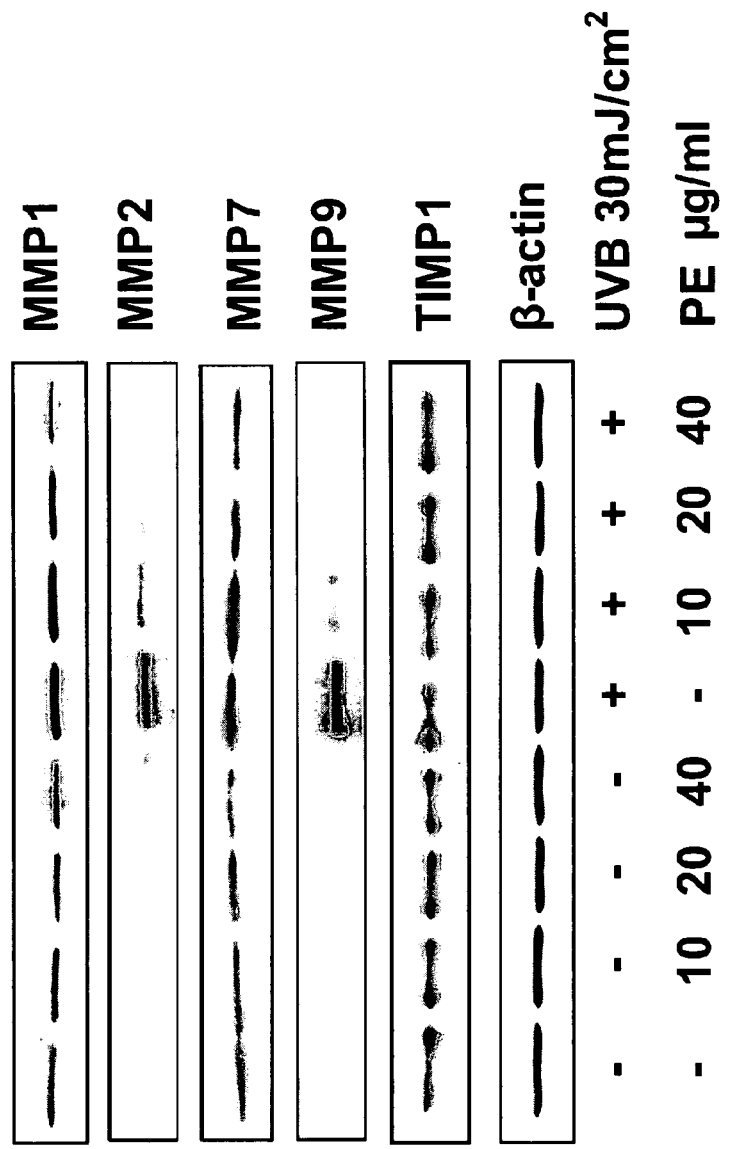
FIG. 25 is a digital composite image illustrating inhibitory effects of PE on UVB-mediated increased expression of MMPs and TIMP-1. HaCaT cells were treated with different doses of PE(10-40 μg/ml) for 24 hours after which the media was removed and cells were washed once with PBS and then fresh PBS was added and cells were exposed to UVB (30 mJ/cm$^2$). After UVB exposure PBS was removed and fresh media was added. Six hours post UVB, the cells were harvested and cell lysates were prepared for western blot analysis. Equal loading was confirmed by stripping the immunoblot and reprobing it for β-actin. The immunoblots shown here are representative of three independent experiments with similar results.

Exposure to UVB radiation is known to upregulate the synthesis of matrix degrading enzymes, MMPs. MMPs are a family of structurally related zinc-dependent endopeptidases, which are capable of degrading a wide variety of ECM components and play an important role in photoaging. The effect of PE on UVB-induced MMPs expression in HaCaT cells was evaluated. FIG. 25 shows that UVB (30 mJ/cm²) irradiation of HaCaT cells resulted in a marked increase in MMP-1, MMP-2, MMP-7 and MMP-9 proteins. This data show that pretreatment of HaCaT cells with PE (10-40 µg/ml) decreased UVB-mediated increase in MMP-1, MMP-2, MMP-7 and MMP-9 protein levels.

UVB radiation has been reported to cause induction of different MMPs that degrade collagen. MMP-mediated collagen damage has been shown to be a major contributor of photoaged human skin. Although irradiation-induced expression of MMPs gene occurs predominantly in the epidermis, MMP proteins and their enzymatic activity are abundant in both the dermis and the epidermis. UVB irradiation which induces secretion of MMPs in skin cells such as keratinocytes, fibroblasts and inflammatory cells, contribute substantially to the connective tissue damage that occurs during photoaging.

PE Inhibits UVB-Mediated Decrease in TIMP-1 Protein Expression

Extracellular matrix metabolism is tightly controlled by MMPs and their tissue inhibitors, TIMPs, and the balance between these plays an important role in the maintenance of tissue homeogenesis. The effect of PE on UVB-mediated altered TIMP-1 expression was studied. FIG. 25 show that UVB (30 mJ/cm²) caused a decrease in TIMP-1, whereas treatment of HaCaT cells with PE (10-40 µg/ml) prior to UVB exposure inhibited UVB-mediated decrease of TIMP-1 protein. These results show that PE inhibit UVB-induced matrix degrading enzymes in HaCaT cells.

Both MMPs and TIMPs are primary enzymes regulating the metabolism of collagen, but their effects are opposite. MMPs decompose ECM while TIMPs inhibit the activity of MMPs and prevent breakdown of ECM. TIMP-1 is important in ECM metabolism as it can inhibit the activity of all MMPs except MT-MMP. FIG. 25 demonstrates that UVB-irradiation induced MMP-1, MMP-2, MMP-7 and MMP-9 in HaCaT keratinocytes whereas it inhibited TIMP-1 protein expression. Pretreatment of HaCaT cells with PE abrogated this effect. Therefore, PE inhibition of the induction of MMPs can alleviate UV-induced photoaging in terms of protection from collagen destruction.

PE Inhibits UVB-Induced Phosphorylation of c-jun and MAPKs

Figure 26:
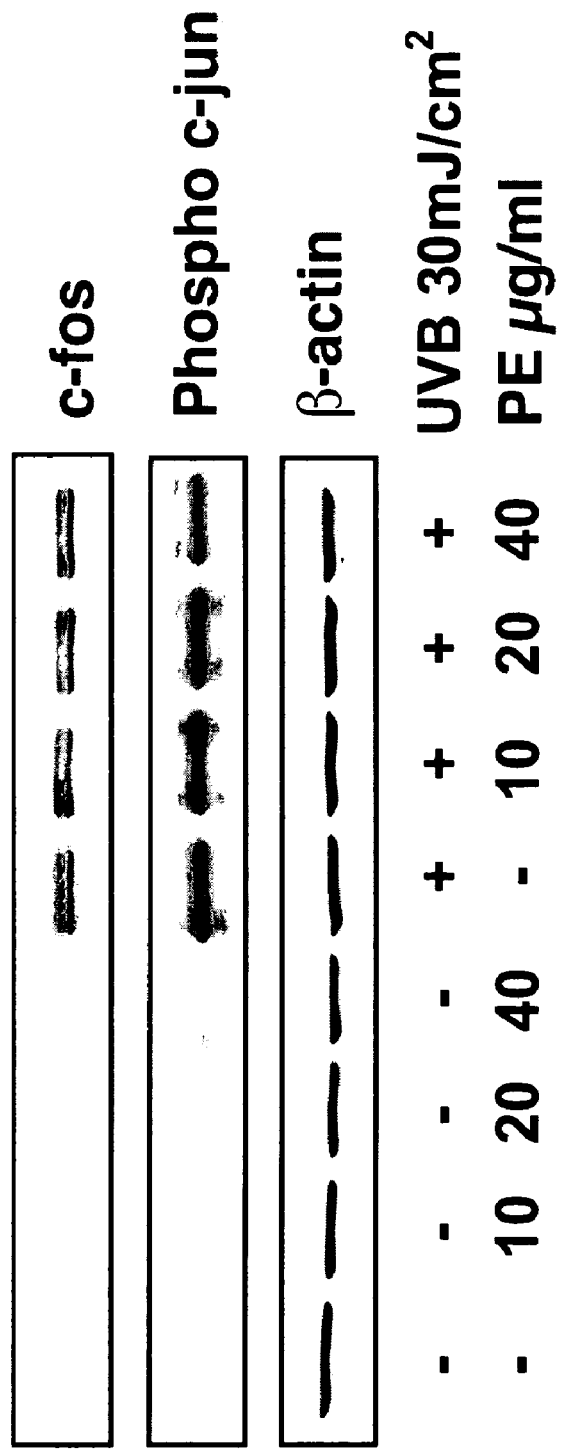
FIG. 26 is a digital composite image illustrating effects of PE on UVB-mediated phosphorylation of c-jun and expression of c-fos. HaCaT cells were treated with different doses of PE (10-40 μg/ml) for 24 hours after which the media was removed and cells were washed once with PBS and then fresh PBS was added and cells were exposed to UVB (30 mJ/cm$^2$). After UVB exposure PBS was removed and fresh media was added. Six hours post UVB, the cells were harvested and cell lysates were prepared for western blot analysis. Equal loading was confirmed by stripping the immunoblot and reprobing it for β-actin. The immunoblots shown here are representative of three independent experiments with similar results.

Activator protein-1 (AP-1) is closely related to matrix degrading enzymes that induce breakdown of collagen. Jun proteins form homodimers or heterodimers with fos proteins to form AP-1 complexes. The transcriptional activity of AP-1 is dependent on the degree of phosphorylation of c-jun and expression of c-fos. The effects of PE on UVB-induced phosphorylation of c-jun protein and expression of c-fos protein were investigated. FIG. 26 shows that UVB (30 mJ/cm²) irridation of HaCaT cells increased the level of phosphorylated c-jun and c-fos proteins. Pretreatment of HaCaT cells with PE (10-40 µg/ml) inhibited UVB-mediated phosphorylation of c-jun. PE did not cause any significant change against UVB-induced expression of c-fos protein in HaCaT cells.

Figure 27:
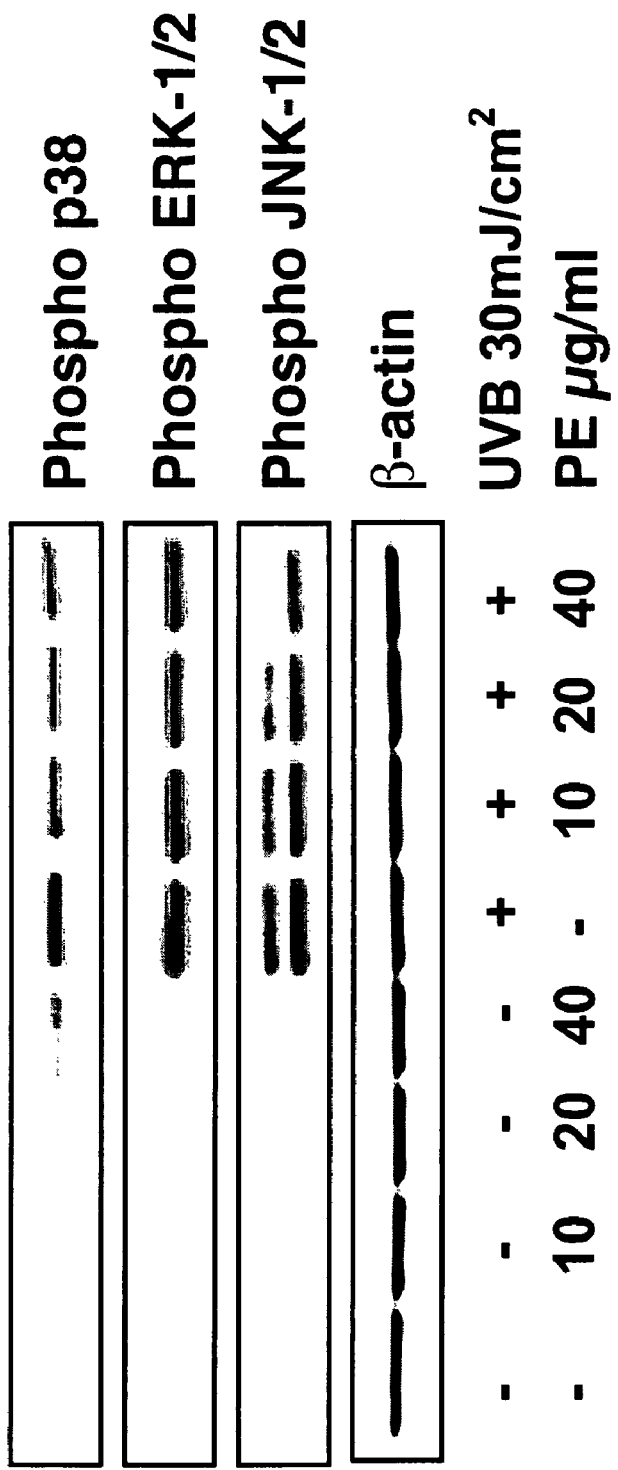
FIG. 27 is a digital composite image illustrating inhibitory effects of PE on UVB-mediated phosphorylation of ERK-1/2, JNK-1/2 and p38. HaCaT cells were treated with different doses of PE (10-40 μg/ml) for 24 hours after which the media was removed and cells were washed once with PBS and then fresh PBS was added and cells were exposed to UVB (30 mJ/cm$^2$). After UVB exposure PBS was removed and fresh media was added. One hour post UVB, the cells were harvested and cell lysates were prepared for western blot analysis. Equal loading was confirmed by stripping the immunoblot and reprobing it for β-actin. The immunoblots shown here are representative of three independent experiments with similar results.

MAPKs encompass a large number of serine/threonine kinases involved in regulating a wide array of cellular processes including proliferation, differentiation, stress adaptation, and apoptosis. The MAPKs are divided into three multimember subfamilies: extracellular signal regulated kinase (ERK-1/2), c-jun amino-terminal kinase (JNK-1/2) and p38. UVB-induced phosphorylations of MAPKs have been shown to be inhibited by the use of antioxidants, thereby suggesting that MAPKs are important targets affected by oxidative stress. The effects of PE on UVB induced MAPKs in HaCaT cells was investigated by using phospho-specific MAPKs antibodies. FIG. 27 shows that UVB (30 mJ/cm²) irradiation induced the phosphorylation of MAPKs, whereas treatment of HaCaT cells with PE (10-40 µl/ml) prior to UVB irradiation decreased UVB-mediated phosphorylation of these MAPKs.

UV radiation induced generation of ROS was suggested to contribute significantly to the signaling events, leading to gene expression. The c-jun gene which encodes the nuclear phosphoprotein c-jun, in association with constitutively expressed c-fos, binds to the AP-1 sites of DNA and acts as a regulatory factor for gene transcription. It has been proposed that activation of AP-1 participate in the UVB-driven breakdown of the dermal ECM in human skin by inducing the expression of a series of metalloproteinases responsible for collagen degradation. FIG. 26 show that UV irridation of HaCaT cells, increased the level of phosphorylated c-jun along with c-fos whereas pretreatment of HaCaT keratinocytes with PE inhibited UVB-induced phosphorylation of c-jun. These results show that inhibition of c-jun phosphorylation which is known to be closely associated with UV-induced AP-1 activation, likely contributes to the prevention of UVB-induced AP-1-regulated MMPs in human skin.

UVB-induced phosphorylation of MAPK proteins namely, ERK-1/2, JNK-1/2, and p38, has been implicated in various skin diseases, including skin cancer and photoaging. The phosphorylation of the MAPK proteins is known to be mediated through UVB-induced oxidative stress. UVB-induced phosphorylation of MAPKs has been shown to be inhibited by the use of antioxidants, thereby suggesting that these are important targets affected by ROS. Accumulating evidence indicates that UV radiation also activates cell surface growth factor and cytokine receptors which stimulate MAPK signal transduction pathways. FIG. 27 demonstrate that pretreatment of HaCaT cells with PE inhibited UVB-mediated phosphorylation of ERK-1/2, JNK-1/2 and p38. Since MAPKs are related to c-jun phosphorylation and expression, with subsequent AP-1 activation, therefore the inhibition of UVB-induced c-jun phosphorylation by PE may be mediated by inhibition of phosphorylation of MAPKs.

In conclusion, the anti-oxidative and anti-photoaging effect of PE was demonstrated in this study. Pretreatment with PE inhibited UVB-mediated decrease in cell viability, decrease in intracellular GSH content, and increase in LPO. PE attenuated UVB-induced phosphorylation of MAPKs and c-jun protein. This study further suggests that PE maintained cellular redox status and inhibited subsequent collagen degradation following UVB exposure. This study reveals the effectiveness of PE in the prevention of UVB-mediated damage and photoaging.

EXAMPLE 7

An In Vivo Evaluation for the Measurement of the Reservoir Effect of Pomegranate-Derived Skin Cream Upon exposure to UV light, photooxidative reactions are initiated which are damaging to biomolecules and affect the integrity of cells and tissues. Photooxidative damage plays a role in pathological processes and is involved in the development of disorders affecting the skin.

The protective effect of pomegranate-derived skin cream from the Example 4 was determined by assessing lipid peroxyl free radical scavenging capacity on the skin. Free radicals have been implicated in many of undesirable aspects of skin aging whether due to intrinsic cause or to exposure to UV radiation. Carotenoids like beta-carotene are efficient antioxidants scavenging singlet molecular oxygen and peroxyl radicals generated in during photooxidation. The bleaching of carotenoids has been used to evaluate the auto-oxidation activity of natural products. This technique can be used to evaluate, in vivo in non-invasive way, the ability of skin cream products to scavenge lipid peroxyl radicals. Basically, the method includes measuring the bleaching of beta-carotene applied to the skin when irradiated by UVA.

A sufficient number of male or female human subjects exhibiting skin types I-III and ranging in the age from 18 to 65 years old in general good health as determined by medical history and absence of any skin abnormalities were selected for the study. An individual skin type is determined by an Individual Topology Angle (ITA), which can be found by using the following formula: $ITA° = (arcTan((L*-50)/b*) \times 180/3.1415$.

Dr. Scholl's® Round Adhesive callus pad (Schering-Plough, Kenilworth, N.J.) were placed on the volar surface of the designated forearm (pre-cleaned with alcohol) of subjects. These callus pads were used to retain the beta-carotene solution (saturated in light mineral oil, with b* color value no less than 45 as determined by chromameter), the pomegranate-derived skin cream of Example 4 and a positive control using commercially available skin cream product, RENOVA®, containing 0.02% all-trans-retinoic acid ((all-E)-3,7-dimethyl-9-(2,6,6-trimethyl-1-cyclonexen-1-yl)-2,4,6,8-nonatetraenoic acid). A baseline chromameter reading is taken after all of the callus pads have been applied. 2 mg/cm$^2$ of test skin cream and the positive control are applied in duplicate to each of the 2 sites. This is accomplished by means of a pre-calibrated syringe or by weighing the appropriate test material amount in a weigh boat. The test product and positive control are allowed to set on the forearm at ambient temperature for 15 minutes. The chromameter is used to measure the b* parameter of the coloration of the treated skin. Measurements are taken on the treated and untreated sites. The beta-carotene solution is then applied by means of a finger cot to obtain a uniform, homogenous orange color on all sites (pre-treated and non-treated), excluding the two control sites. The chromameter is used to measure the b* component of each site, post-application of the beta-carotene. The beta-carotene painted skin is exposed to UVA radiation and b* is measured at 1.0 J/cm$^2$, 3.0 J/cm$^2$ and 6.0 J/cm$^2$ intervals. The total exposure to UVA radiation is 6.0 J/cm$^2$.

Bleaching is reported as the color index versus radiation energy (J/cm2) for a system in which the output of the UV source is constant. It can be expressed in terms of a color index, I, defined as: $I = ((bn*-bi*)/(bo*-bi*))$ where bn* is the value of b* measured after n J of irradiation of the area treated with cosmetic formulation and painted with the beta-carotene; bo* is the value of b* after the application of the beta-carotene, but before irradiation; and, bi* is the value of b* before application of the beta-carotene. This index compensates for any effects of skin type on bi* and bn*. ANOVA test was applied to determine color index differences amongst skin cream products and beta-carotene at each time interval.

Table 1 shows comparison of the ability of skin cream products to scavenge lipid peroxyl radicals by inhibiting the bleaching of beta-carotene applied to the skin when irradiated by UVA at 10 minutes.

TABLE 1

Comparison amongst Skin Cream Products and ®-carotene at 10 minutes

| | Mean of Color Index | Number of Subjects |
|---|---|---|
| Pomegranate-derived Skin Cream | 81% | 26 |
| 0.02% All-trans-retinoic acid Skin Cream | 74% | 24 |
| ®-carotene | 42% | 48 |

Overall F-test was significant (p<0.0001). There were significant differences between ®-Carotene and all test products. There was no significant difference between the 0.02% all-trans-retinoic skin cream and the pomegranate-derived skin cream.

Table 2 shows comparison of the ability of skin cream products to scavenge lipid peroxyl radicals by inhibiting the bleaching of beta-carotene applied to the skin when irradiated by UVA at 30 minutes.

TABLE 2

Comparison amongst Skin Cream Products and ®-carotene at 30 minutes

| | Mean of Color Index | Number of Subjects |
|---|---|---|
| Pomegranate-derived Skin Cream | 79% | 26 |
| 0.02% All-trans-retinoic acid Skin Cream | 62% | 24 |
| ®-carotene | 16% | 48 |

Overall F-test was significant (p<0.0001). There were significant differences between ®-carotene and all test products. There was a significant difference between the 0.02% all-trans-retinoic skin cream and the pomegranate-derived skin cream.

Table 3 shows comparison of the ability of skin cream products to scavenge lipid peroxyl radicals by inhibiting the bleaching of beta-carotene applied to the skin when irradiated by UVA at 60 minutes.

TABLE 3

Comparison amongst Skin Cream Products and ®-carotene at 60 minutes

|  | Mean of Color Index | Number of Subjects |
|---|---|---|
| Pomegranate-derived Skin Cream | 75% | 26 |
| 0.02% All-trans-retinoic acid Skin Cream | 46% | 24 |
| ®-carotene | 0% | 48 |

Overall F-test was significant (p<0.0001). There were significant differences between ®-carotene and all test products. There was also significant difference between the 0.02% all-trans-retinoic skin cream and the pomegranate-derived skin cream.

The results suggest that the topical application on human skin of the pomegranate-derived skin cream from the Example 4 effectively acts as a protective agent against UVA-induced oxidative damage.

EXAMPLE 8

Case Histories of Treatment with a Pomegranate-Derived Skin Care Composition

Each of the following subjects was treated with the pomegranate-derived skin care composition prepared according to the method of Example 4.

Case History I

A fifty-two year old female subject complained of wrinkled facial skin. After two weeks of applying the skin cream prepared according to the method of Example 4, the subject reported that her skin bad greater elasticity and turgor and that her skin was less wrinkled. The patient also reported that the cream had a pleasant feel.

Case History II

A seventy-two year old female subject applied the skin cream, prepared according to the method of Example 4, to the skin on her face and on the backs of her hands. After one week, the patient felt that the skin of her hands and face "looked younger".

EXAMPLE 9

Antimicrobial Activity of PJC and PE

The following assay was used to determine the efficacy of PJC and PE against common bacteria (gram-positive *Staphylococcus aureus* ATCC 6538 and anaerobic gram-positive *Propionibacterium acnes* ATCC 11827). PJC was prepared in accordance of Example 1 and PE was prepared in accordance of Example 2. Serial dilutions of compounds were prepared in microdilution plates. Mueller Hinton broth cultures of strain were grown or adjusted to match the turbidity of a 0.5 McFarland standard. 1:200 dilutions were made in appropriate broth (for example, cation supplemented Mueller Hinton broth for *S. aureus*) to allow a final innoculum of $1 \times 10^5$ cfu. The plates were incubated at 35° C. in ambient air for 18-24 hours, read spectrophotometrically, and checked manually for evidence of bacterial growth.

Serial dilutions of PJC and PE were also added to *Brucella agar* supplemented with laked sheep blood for *P. acnes* tests. A standard inoculum was transferred to the plate using a stainless steel replicator. After 48 hours of anaerobic incubation at 35° C. plates were examined.

The Minimum Inhibitory Concentration (MIC) was defined as the lowest concentration of the pomegranate-derived compositions against bacteria. Table 4 gives the MIC of selected pomegranate-derived composition against a variety of bacteria. Growth is indicated by positive symbol (+) and inhibition of growth is indicated by negative symbol (−). PJC shows growth inhibition of *P. acnes* at 2% concentration and 9% concentration for *S. aureus*. PE shows growth inhibition at 1% concentration for both *P. acnes* and *S. aureus*.

Both PJC and PE have antimicrobial activity in vitro. These data demonstrate the utility of the pomegranate-derived compositions of this invention as antibacterials. The skin care formulation with one or more pomegranate-derived compositions may be used for treating and preventing skin disorder resulting from microbial infection.

TABLE 4

Minimum Inhibitory concentration

| Microorganisms | 1.0 | 2.0 | 3.0 | 4.0 | 5.0 | 6.0 | 7.0 | 8.0 | 9.0 | 10.0 | MIC (%) |
|---|---|---|---|---|---|---|---|---|---|---|---|
| | \multicolumn{10}{c}{Product Concentration (%) for PJC} | |
| *P. acnes* | + | − | − | − | − | − | − | − | − | − | 2.0 |
| *S. aureus* | + | + | + | + | + | + | + | + | − | − | 9.0 |
| | \multicolumn{10}{c}{Product Concentration (%) for PE} | |
| *P. acnes* | − | − | − | − | − | − | − | − | − | − | 1.0 |
| *S. aureus* | − | − | − | − | − | − | − | − | − | − | 1.0 |

EXAMPLE 10

An example of ingredients that may be used to formulate an embodiment of cleanser or gel serum manufactured by a general procedure is illustrated in Table 6.

TABLE 6

Ingredients

| % w/w | Tradename | INCI Name |
|---|---|---|
| | Deionized Water | Water |
| | Amigel | Sclerotium Gum |
| | Hydrolite-5 | Pentylene Glycol |
| | Citric acid | Citric acid |
| | Potassium Citrate | Potassium Citrate |
| | Sodium Citrate | Sodium Citrate |
| | Jojoba Pro HP | Hydrolyzed Jojoba Protein |
| | Oristar DMAEB | DMAE DL-Bitartrate |
| | PE | Punica Granatum Fruit Extract |
| | Olivem 1000 | Cetearyl Olivate (and) Sorbitan Olivate |

EXAMPLE 11

An example of ingredients that may be used to formulate an embodiment of toner manufactured by a general procedure is illustrated in Table 7.

TABLE 7

Ingredients

| % w/w | Tradename | INCI Name |
|---|---|---|
| | Deionized Water | Water |
| | Hydrolite-5 | Pentylene Glycol |
| | Viscarin PC 389 | *Chondrus Crispus* (Carrageenan) |
| | Potassium Citrate | Potassium Citrate |

TABLE 7-continued

| | Ingredients | |
|---|---|---|
| % w/w | Tradename | INCI Name |
| | Monohydrate | |
| | Sodium Citrate Dihydrate | Sodium Citrate |
| | Salicylic Acid, USP | Salicylic Acid |
| | PE | *Punica Granatum* Fruit Extract |

EXAMPLE 12

An example of ingredients that may be used to formulate an embodiment of skin cream or night cream manufactured by a general procedure is illustrated in Table 8.

TABLE 8

| | Ingredients | |
|---|---|---|
| % w/w | Tradename | INCI Name |
| | Deionized Water | Water |
| | Amigel | Sclerotium Gum |
| | Olivem 1000 | Cetearyl Olivate (and) Sorbitan Olivate |
| | Captex 300 | Caprylic/Capric Triglyceride |
| | Jarplex SB35 | *Butyrospermum Parkii* (shea butter) |
| | Eurol BT | *Olea Europaea* (Olive) Leaf Extract, water |
| | Hydrolite-5 | Pentylene Glycol |
| | Oristar DMAEB | DMAE DL-Bitartrate |
| | PSO | *Punica Granatum* Seed Oil |

EXAMPLE 13

A subject applied the skin cream of Example 12 once daily as part of an open label, pharmacokinetic clinical study. This patient had a number of particular non-inflammatory lesions (closed comedones) at baseline. The number of non-inflammatory lesions decreased after four weeks of treatment with the skin cream of Example 12 applied once daily. After four weeks of treatment, the subject reported that the skin cream was gentle and soothing to skin, helped reduce redness, and helped to re-texture skin resulting in a smooth, even appearance and skin tone. Subject also reported that the skin looked more radiant and luminous.

EXAMPLE 14

Subjects, males and females, 12-55 years of age, participated in the evaluator blinded, randomized human clinical study, 25 in each treatment group. Subjects were Fitzpatrick skin type I-IV and having mild to moderate facial acne (at least four inflammatory blemishes on the face at the baseline evaluation). The number of non-inflammatory lesions (open and closed comedones) and inflammatory lesions (papules and pustules) of the face of each subject were counted at baseline and week 2 and week 4 of skin care treatment using one of the following regimens:

Regimen A—Pomegranate-derived Skin Care Regimen. Apply the foaming cleanser of Example 10 twice daily and then rinse off well with water; apply the clarifying toner of Example 11 with cotton ball twice daily; and, apply the skin cream of Example 12 to affected area sparingly twice daily.

Regimen B—PROACTIVE® Solution System. Apply Renewing Cleanser twice daily. Follow with Revitalizing Toner. Revitalizing Toner: apply to cleansed skin with cotton ball or pad, morning and night as needed. Allow Toner to dry and follow with Repairing Lotion. Repairing Lotion: use morning and night. If going outside, use a sunscreen.

The Regimen C—Retin-A Micro Regimen. Apply Neutrogena Liquid Neutrogena, Facial Cleansing Formula, Fragrance Free, twice daily. Apply Retin-A Cream once each night. Apply Olay Refreshing Toner twice daily.

The efficacy of skin care therapy was assessed by means of VISIA-CR™ photo-imaging equipment (Canfield Scientific, Fairfield, N.J.). Subjects were photographed using standard light, UV, cross-polarization and parallel-polarization techniques for high quality, reproducible facial images. Photographs were taken by reproducibly positioning the head of the subject, using stationary chin and forehead supports, reproduction ratios and flash type at each study visit. One full-faced and two side-view images of each subject were captured at the baseline (e.g., week 0), week 2 and week 4 visits.

A subjective assessment of the effects of a test material were determined by questioning the treated subject with regard to the efficacy of the product following use (see Table 10). Questionnaire were administered with the eListen 4.7 Electronic Survey and Data Collection Tool which allows for an efficient and accurate method of determining subject response proportions to assess the consensus opinion of a clinical study population.

Every subject was observed at baseline, week 2 and week 4 for signs of irritation or inflammation by an evaluator. The evaluator examines sign of skin reaction on each skin care application site. Skin irritancy or inflammation (e.g., erythema, edema, dryness and peeling) was rated according to the following commonly used 5-point scale:

1=No sign of irritation or inflammation; 2=Slight perceptible irritation or inflammation; 3=Mild sign of irritation or inflammation; 4=Moderate sign of irritation or inflammation; and, 5=Severe sign of irritation or inflammation.

Other signs of skin reaction to the tested skin care products were noted as adverse events and recorded. A total of nine readings were performed during the study.

Efficacy assessments were thus based on blinded evaluator assessment of amelioration of acne, including by assessing one or more of the signs and symptoms of acne and including where the amelioration is indicated by one or more of the following: reduction in inflammatory lesion count (e.g., facial), reduction in non-inflammatory lesion count (e.g., facial), reduction in total lesion count (e.g., facial) or an increased proportion of clear or almost clear skin (e.g., facial). A reduction in lesion count (e.g., inflammatory, non-inflammatory and/or total) may be analyzed as final lesion counts, changes from baseline (e.g., baseline counts−end of study counts) or percent change (e.g., change/baseline counts×100%). An increased proportion of clear or almost clear skin was analyzed in a variety of ways by a trained evaluator (e.g., physician, investigator or dermatologist), typically a physician global evaluation, including using a Global Static Physician Score, Static Physician Global Assessment, Investigator Global Evaluation, Evaluator's Global Severity Scale, or other known scale (e.g., Cook's Scale, Leeds Scale, etc.). A primary measure of efficacy variables percent change from baseline as week 2 and week 4 in (a) inflammatory lesion counts, (b) non-inflammatory lesion counts, and (c) total lesion counts, including, for example, where the counts are facial.

The efficacy of skin care treatment is indicated by amelioration of acne, including where the amelioration is indicated by a reduction in the number and/or severity of one or more signs of symptoms of acne, including, for example, a reduction (e.g., decrease) in lesion counts assessed after treatment.

The number of inflammatory lesions (sum of papules and pustules), non-inflammatory lesions (sum of open and closed comedones), and the total lesion count (sum of the inflammatory lesions and non-inflammatory lesions) are derived for each subject and each study visit (baseline, week 2 and week 4). Within each regimen, ANOVA test was applied to determine the differences between baseline, week 2 and week 4. If overall F-test was significant, Tukey's multiple comparison was further applied to determine where the differences exist. Comparisons among the four regimens were based on percentage change from baseline or change from baseline at Week 2 and Week 4. ANOVA test was applied. If overall F-test was significant, Tukey's multiple comparison was further applied to determine where the differences exist.

TABLE 8

Comparison of Lesion Counts Between Baseline, Week 2 and Week 4 of Skin Clarifying Treatment.

| Treatment | Parameter | Mean of Lesion Count | | | P-Value | Significant Pair |
|---|---|---|---|---|---|---|
| | | Baseline | Week 2 | Week 4 | | |
| A | Open and Closed Comedones | 41 | 37 | 24 | <0.0001 | Baseline vs. W4 W2 vs. W4 |
| | Papules and Pustules | 8 | 7 | 6 | 0.0408 | Baseline vs. W4 |
| | Total Lesion Count | 49 | 44 | 30 | <0.0001 | Baseline vs. W4 W2 vs. W4 |
| B | Open and Closed Comedones | 33 | 30 | 23 | <0.0001 | Baseline vs. W4 W2 vs. W4 |
| | Papules and Pustules | 7 | 5 | 4 | <0.0001 | Baseline vs. W2 Baseline vs. W4 |
| | Total Lesion Count | 40 | 34 | 27 | <0.0001 | Baseline vs. W2 Baseline vs. W4 W2 s. W4 |
| C | Open and Closed Comedones | 41 | 35 | 26 | <0.0001 | Baseline vs. W2 W2 vs. W4 |
| | Papules and Pustules | 10 | 7 | 7 | 0.0219 | Baseline vs. W2 Baseline vs. W4 |
| | Total Lesion Count | 50 | 42 | 33 | <0.0001 | Baseline vs. W2 Baseline vs. W4 W2 vs. W4 |

TABLE 9

Comparison of Each Parameter Change from Baseline at Week 2 and Week 4 amongst three treatments.

| Parameter | Time Point | Mean of % Change from Baseline | | | P-Value | Significant Comparison |
|---|---|---|---|---|---|---|
| | | A | B | C | | |
| Open and Closed Comedones | Week 2 | −9% | −9% | −11% | >0.05 | N/A |
| | Week 4 | −37% | −27% | −31% | >0.05 | N/A |
| Papules and Pustules | Week 2 | −28% | −40% | −30% | >0.05 | N/A |
| | Week 4 | −24% | −47% | −22% | >0.05 | N/A |
| Total Lesion Count | Week 2 | −12% | −15% | −15% | >0.05 | N/A |
| | Week 4 | −36% | −33% | −30% | >0.05 | N/A |

Skin care regimen with pomegranate-derived formulations was statistically generally similar to Proactiv regimen and Retin-A Micro regimen (see Tables 8 and 9). All products were well accepted by subjects without any significant irritation with daily treatment.

TABLE 10

Subject Efficacy Assessment, Percentage of Subjects Responding Positively.

| Efficacy Questionnaire | Regimen A (Pomegranate) | Regimen B (PROACTIV) | Regimen C (Retin-A Micro) |
|---|---|---|---|
| The product was gentle to my skin: | 88.5 | 96.3 | 65.4 |
| The product helped to soothe my skin: | 84.6 | 87 | 67.3 |
| The product helped to calm my skin by reducing redness: | 75 | 72.2 | 80.8 |
| The product can be used on sensitive skin: | 84.6 | 79.6 | 63.5 |
| The product helped to re-texture my skin resulting in a smooth, even appearance: | 76.9 | 72.2 | 76.9 |
| The product left my skin looking radiant and luminous: | 73.1 | 66.7 | 61.5 |
| The product helped to even out my skin tone: | 65.4 | 77.8 | 67.3 |

The skin care regimen with pomegranate-derived formulations generally met or exceeded PROACTIV and Retin-A Micro on subjective acceptance scores (see Table 10).

There was insignificant peeling, dryness, edema, and erythema with the products tested. The regimen with pomegranate-derived skin care products is acceptable for daily use as skin clarifying regimen.

EXAMPLE 11

Effects of PJC, PE, and PSO on Aquaporins in EpiDermFT™ Cells

The effects of PJC of Example 1, PE of Example 2, and PSO of Example 3 on the expression of aquaporins (AQPs) at the protein and gene expression levels in EpiDermFT™ were assessed EpiDermFT™ consists of normal, human-derived epidermal keratinocytes (NHEK) and normal, human-derived dermal fibroblasts (NHFB) which have been cultured to form a multilayered, highly differentiated model of the human dermis and epidermis.

In human skin, for example, absence of AQP3 is associated with intercellular edema (spongiosis) and down regulation of AQP3 occurs in eczema. The expression of elastin, fibulin-5 and fibrillin-1 were determined in human reconstituted skin (e.g., EpiDerm-FT™). The choice of these molecules is based on that they are widely used as markers of skin elasticity. AQPs have recently been implicated in various diseases such as cancer, edema, eczema, cataract, brain oedema, gallstone disease and nephrogenic diabetes insipidus, as well as in the development of obesity and polycystic kidney disease.

Materials and Methods

EpiDermFT™ tissue samples were transferred onto a six-well plate containing 5 ml of EFT-200-ASY/MM medium (Matek Corp., Ashland, Mass.) overnight under standard cell culture conditions at 37° C. incubator and 5% $CO_2$ in a humid environment. The six-well plate containing tissue samples were topically treated for one hour prior to UVB irradiation in duplicate via gentle pipetting 100 µl of fresh EFT-200-ASY/MM medium containing either PJC (1 or 2 µl/0.1% DMSO/well), PE (0.25 or 0.5 µl/0.1% DMSO/well) or PO (1 or 2 µl/0.1% DMSO/well). After topical treatment, samples were carefully rinsed with PBS, via gentle pipetting of the apical tissue surface to remove any non-absorbed PJC, PE and PSO before UVB irradiation at 60 mJ/$cm^2$ using a custom designed Research Irradiation Unit (Daavlin, Bryan, Ohio) that consists of a fixture mounted on fixed legs. Mounted within the exposure unit are four UVB lamps and the exposure system is controlled by Daavlin Flex Control Integrating Dosimeter.

Tissue samples were harvested 12 hours post-UVB and fixed in 10% neutral buffered formalin for paraffin embedding. 5 mm serial sections of paraffin-embedded tissue sample were mounted on poly-1-lysine coated glass slides (Sigma Chemicals, St Louis, Mo.) for hematoxylin-eosin staining and immunohistochemical evaluation.

For western blot analysis, tissue sample lysate was prepared by keeping the cell in 0.3 ml of lysis buffer (10 mM Tris-HCl, pH 7.4, 150 mM NaCl, 1% Triton X-100, 1 mM EDTA, and 1 mM EGTA) containing 0.2 mM sodium vanadate, 2 mM PMSF, 0.5% NP-40, and 0.2 U/ml aprotinin with freshly added protease inhibitor cocktail at 4° C. for 15 minutes. The cells were scrapped and collected in a microfuge tube and then passed through a 22½-G needle to break up the cell aggregates. The lysates were centrifuged at 13,000×g for 25 min at 4° C. to remove cell debris. Supernatant were collected, and protein estimation was done by BCA method. Equal amount (30-40 µg) of protein was resolved electrophoretically over 12% tris glycine gel, and transferred to a nitrocellulose membrane. The blot containing transferred protein was blocked in blocking buffer (5% nonfat dry milk in 20 mM Tris-buffered saline, pH 7.6 containing 1% Tween20-TBST) for 1 hour at room temperature followed by incubation with appropriate primary antibody in blocking buffer for 2 hours to overnight at 4° C. This was followed by incubation with specific anti-mouse or anti-rabbit secondary antibody conjugated with horseradish peroxidase for 2 hours at room temperature and then washed 3 times, 15 min each in TBST and detected by enhanced chemiluminescence and autoradiography using Blue Lite Autorad film (ISC Bioexpress, Kaysville, Utah).

The bands in western blots were quantitated using densitometry and the results are expressed as relative intensity versus the intensity of normalized untreated and non-UVB-irradiated EpiDermFT™ control tissue sample in the blot.

After treatment with pomegranate-derived composition, AQP3 expression measured at the protein level in human reconstructed epidermis was significantly increased. Water transport through both aquaporins and aquaglyceroporins and glycerol transport through aquaglyceroporins alone are important to skin hydration. The distribution and the variability of aquaporins in human skin cells suggest that these channels may have important roles in skin physiology. AQPs appear to be key protein targets to improve the resistance and quality of the skin surface as well as to improve aging and sun exposure-induced dryness as shown by their roles in 1) hydrating the living layers of the epidermis where the keratinocyte differentiation takes place and 2) barrier formation and recovery.

While the invention herein disclosed has been described by means of specific embodiments and applications thereof, numerous modifications and variations could be made thereto by those skilled in the art without departing from the scope of the invention set forth in the claims.

What is claimed is:

1. A skin care product comprising:
   a skin care composition comprising between about 0.001% to about 20% of an encapsulated, deodorized and stabilized pomegranate seed oil obtained by isohexane extraction of flaked pomegranate seed oil mixed with 50 to 1,000 ppm of at least one of mixed tocopherols, tert-Butylhydroquinone and acrobyl palmitate, wherein said pomegranate seed oil comprises less than about 0.5% free fatty acid; and
   an airless dispensing container containing said skin care composition and configured to dispense said skin care composition while minimizing contact of a remaining portion of said skin care composition to air.

* * * * *